US012685446B2

(12) United States Patent
Buchan et al.

(10) Patent No.: US 12,685,446 B2
(45) Date of Patent: Jul. 21, 2026

(54) SEMI-COMPACT PHOTOACOUSTIC DEVICES AND SYSTEMS

(71) Applicant: QUALCOMM Incorporated, San Diego, CA (US)

(72) Inventors: Nicholas Buchan, San Jose, CA (US); Stephen Michael Gojevic, Lockport, NY (US); Hrishikesh Vijaykumar Panchawagh, Cupertino, CA (US); Yipeng Lu, Moraga, CA (US); Htet Naing, San Diego, CA (US); John Keith Schneider, Williamsville, NY (US); Kostadin Dimitrov Djordjev, Los Gatos, CA (US); Camilo Perez Saaibi, Dublin, CA (US); Sherman Sebastian Antao, San Diego, CA (US); Ye Zhan, Buffalo, NY (US)

(73) Assignee: QUALCOMM Incorporated, San Diego, CA (US)

( * ) Notice: Subject to any disclaimer, the term of this patent is extended or adjusted under 35 U.S.C. 154(b) by 119 days.

(21) Appl. No.: 18/069,877

(22) Filed: Dec. 21, 2022

(65) Prior Publication Data

US 2024/0206737 A1     Jun. 27, 2024

(51) Int. Cl.
*A61B 5/00* (2006.01)
*A61B 5/021* (2006.01)
(Continued)

(52) U.S. Cl.
CPC ........ *A61B 5/0095* (2013.01); *A61B 5/02133* (2013.01); *A61B 5/6898* (2013.01);
(Continued)

(58) Field of Classification Search
CPC . A61B 5/0095; A61B 5/02133; A61B 5/6898; A61B 5/7203; A61B 2562/0204;
(Continued)

(56) References Cited

U.S. PATENT DOCUMENTS

| | | | |
|---|---|---|---|
| 5,348,002 A | 9/1994 | Caro | |
| 6,070,093 A | 5/2000 | Oosta et al. | |

(Continued)

FOREIGN PATENT DOCUMENTS

| | | |
|---|---|---|
| CN | 109363644 B | 4/2021 |
| EP | 2933633 A1 | 10/2015 |

(Continued)

OTHER PUBLICATIONS

M. Naumovska et al., "Mapping the architecture of the temporal artery with photoacoustic imaging for diagnosing giant cell arteritis," Photoacoustics, vol. 27, pp. 100384-100384, Sep. 2022 (Year: 2022).*

(Continued)

*Primary Examiner* — Christopher Koharski
*Assistant Examiner* — Steven Maldonado
(74) *Attorney, Agent, or Firm* — Weaver Austin Villeneuve & Sampson LLP

(57) ABSTRACT

An apparatus may include a platen, a light source system and an ultrasonic receiver system. The platen may be configured to separate one or more received arterial ultrasonic waves generated by blood in an artery, by an arterial wall, or by a combination thereof, from one or more other types of received ultrasonic waves. The platen may have an outer surface with an acoustic impedance that is configured to approximate the acoustic impedance of human skin. The outer surface of the platen may be configured to conform to a surface of the human skin. The apparatus may include a noise reduction system. The light source system may include at least one multi-junction laser diode. The apparatus may include a mirror layer residing between the ultrasonic receiver system and the platen.

27 Claims, 26 Drawing Sheets

(51) Int. Cl.
    *G06F 3/0354*          (2013.01)
    *G10K 11/30*          (2006.01)

(52) U.S. Cl.
    CPC ........ *A61B 5/7203* (2013.01); *G06F 3/03545*
                (2013.01); *G10K 11/30* (2013.01)

(58) Field of Classification Search
    CPC ... A61B 5/489; A61B 5/6826; G06F 3/03545;
                               G10K 11/30
    See application file for complete search history.

(56)              References Cited

U.S. PATENT DOCUMENTS

| | | |
|---|---|---|
| 6,394,960 B1 | 5/2002 | Shinogi et al. |
| 11,872,018 B2 | 1/2024 | Abreu |
| 2001/0033275 A1 | 10/2001 | Kent et al. |
| 2006/0161992 A1 | 7/2006 | Kempf |
| 2006/0184042 A1 | 8/2006 | Wang et al. |
| 2006/0258939 A1 | 11/2006 | Pesach et al. |
| 2007/0197886 A1* | 8/2007 | Naganuma ......... A61B 5/14532 |
| | | 600/322 |
| 2010/0268042 A1* | 10/2010 | Wang ................. A61B 5/14546 |
| | | 600/322 |
| 2013/0109947 A1 | 5/2013 | Wood |
| 2014/0039293 A1* | 2/2014 | Oraevsky ............. A61B 5/0095 |
| | | 600/407 |
| 2014/0058245 A1 | 2/2014 | Oishi et al. |
| 2014/0275941 A1 | 9/2014 | Kang et al. |
| 2014/0275943 A1 | 9/2014 | Kang et al. |
| 2015/0051473 A1 | 2/2015 | Huang et al. |
| 2015/0133765 A1* | 5/2015 | Ichihara ............... A61B 5/0073 |
| | | 600/407 |
| 2015/0261323 A1* | 9/2015 | Cui ........................ G06F 3/042 |
| | | 345/175 |
| 2015/0297091 A1 | 10/2015 | Nakatsuka |
| 2017/0108429 A1 | 4/2017 | Schmid |
| 2017/0150890 A1 | 6/2017 | Herzog et al. |
| 2017/0231503 A1* | 8/2017 | Nakatsuka ............... A61B 8/13 |
| | | 600/407 |
| 2017/0231598 A1* | 8/2017 | Baek ........................ A61B 8/54 |
| | | 600/454 |
| 2017/0323132 A1* | 11/2017 | Lu ........................ A61B 5/0095 |
| 2017/0363742 A1 | 12/2017 | Price et al. |
| 2018/0055369 A1* | 3/2018 | Burns .................. A61B 5/6898 |
| 2018/0164432 A1 | 6/2018 | Lal et al. |
| 2018/0286379 A1 | 10/2018 | Norris et al. |
| 2018/0360416 A1* | 12/2018 | Nakai ..................... G10K 11/30 |
| 2019/0377962 A1* | 12/2019 | Kitchens .............. A61B 5/0095 |
| 2020/0380232 A1* | 12/2020 | Yoon ....................... G06F 21/32 |
| 2021/0052164 A1 | 2/2021 | Shnaiderman et al. |
| 2021/0158002 A1* | 5/2021 | Kitchens ............ G06V 40/1371 |
| 2021/0270780 A1* | 9/2021 | Wu .................... G01N 29/2418 |
| 2022/0039699 A1 | 2/2022 | Esenaliev |
| 2022/0175258 A1 | 6/2022 | Kitchens et al. |
| 2023/0042741 A1 | 2/2023 | Rohling et al. |
| 2023/0397819 A1 | 12/2023 | Khang |

| | | |
|---|---|---|
| 2024/0206736 A1 | 6/2024 | Lu et al. |
| 2024/0206738 A1 | 6/2024 | Buchan et al. |
| 2024/0206739 A1 | 6/2024 | Buchan et al. |
| 2024/0210308 A1 | 6/2024 | Buchan et al. |
| 2024/0210309 A1 | 6/2024 | Buchan et al. |

FOREIGN PATENT DOCUMENTS

| | | | | |
|---|---|---|---|---|
| EP | 2203733 B1 | 5/2017 | | |
| EP | 3136952 B1 | 7/2019 | | |
| JP | H09145683 A | 6/1997 | | |
| JP | 6826732 B2 | 2/2021 | | |
| KR | 20140004058 A | 1/2014 | | |
| WO | 2011162000 A1 | 12/2011 | | |
| WO | WO-2018044393 A1 | 3/2018 | | |
| WO | WO 2023107246 A1 * | 6/2023 | ............... | A61B 8/13 |

OTHER PUBLICATIONS

M. Wu, A. F. van der Steen, E. Regar, and G. van Soest, "Emerging Technology Update Intravascular Photoacoustic Imaging of Vulnerable Atherosclerotic Plaque," Interventional Cardiology Review, vol. 11, No. 2, p. 120, 2016 (Year: 2016).*

Intravascular Photoacoustic Imaging of Vulnerable Atherosclerotic Plaque (Year: 2016).*

Mapping the architecture of the temporal artery with photoacoustic imaging for diagnosing giant cell arteritis (Year: 2022).*

S. Gratt, K. Passler, R. Nuster, and G. Paltauf, "Photoacoustic imaging using a conical axicon detector," SPIE Proceedings, vol. 7371, Jul. 2009 (Year: 2009).*

International Search Report and Written Opinion—PCT/US2023/078699—ISA/EPO—Mar. 15, 2024.

Montilla L.G., et al., "Note: Real-time Photoacoustic and Ultrasound Imaging: A Simple Solution for Clinical Ultrasound Systems with Linear Arrays", Physics in Medicine and Biology, Institute of Physics Publishing, Bristol GB, vol. 58, No. 1, Dec. 6, 2012, pp. N1-N12, XP020236232, para [0004], [0054], figure 2.

Dangi A., et al., "Ring Ultrasound Transducer Based Miniaturized Photoacoustic Imaging System", HHS Public Access, Proceedings of IEEE Sensors, Oct. 2018, pp. 1-12.

Fuchs U., et al., "Various Beam Shaping Applications Utilizing Axicons", vol. 9581: Laser Beam Shaping XVI, Sep. 2015, 3 Pages.

Li H., et al., "Monte Carlo Simulation of Light Scattering in Tissue for the Design of Skin-like Optical Devices", Biomedical Optics Express, vol. 10, No. 2, Feb. 1, 2019, pp. 868-878.

Xia J., et al., "Calibration-Free Quantification of Absolute Oxygen Saturation Based on the Dynamics of Photoacoustic Signals", Optics Letters, vol. 38, No. 15, Aug. 1, 2013, pp. 2800-2803.

Zhang X., et al., "Photoacoustic Identification of Blood Vessel Deformation Under Pressure", AIP Advances, American Institute Of Physics, 2 Huntington Quadrangle, Melville, NY 11747, vol. 9, No. 7, Jul. 24, 2019, XP012239341, 8 Pages, p. 3, right-hand column, line 12.

Boucher J-F., et al., "Ultra High Efficiency 1550nm Multi-junction Pulsed Laser Diodes", Proceedings of the SPIE, vol. 7480, Sep. 17, 2009, US, pp. 74800K-74800K-1, 12 Pages, XP055837104.

\* cited by examiner

LIGHT SOURCE

PIEZO Rx

OPTICAL

ACOUSTIC

Finger 115

300

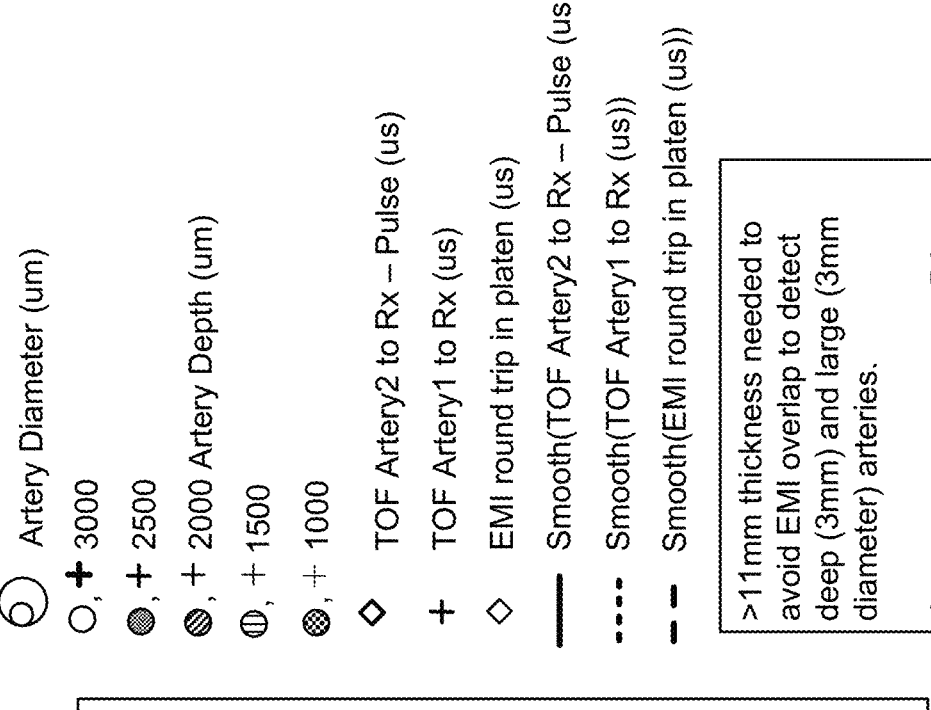
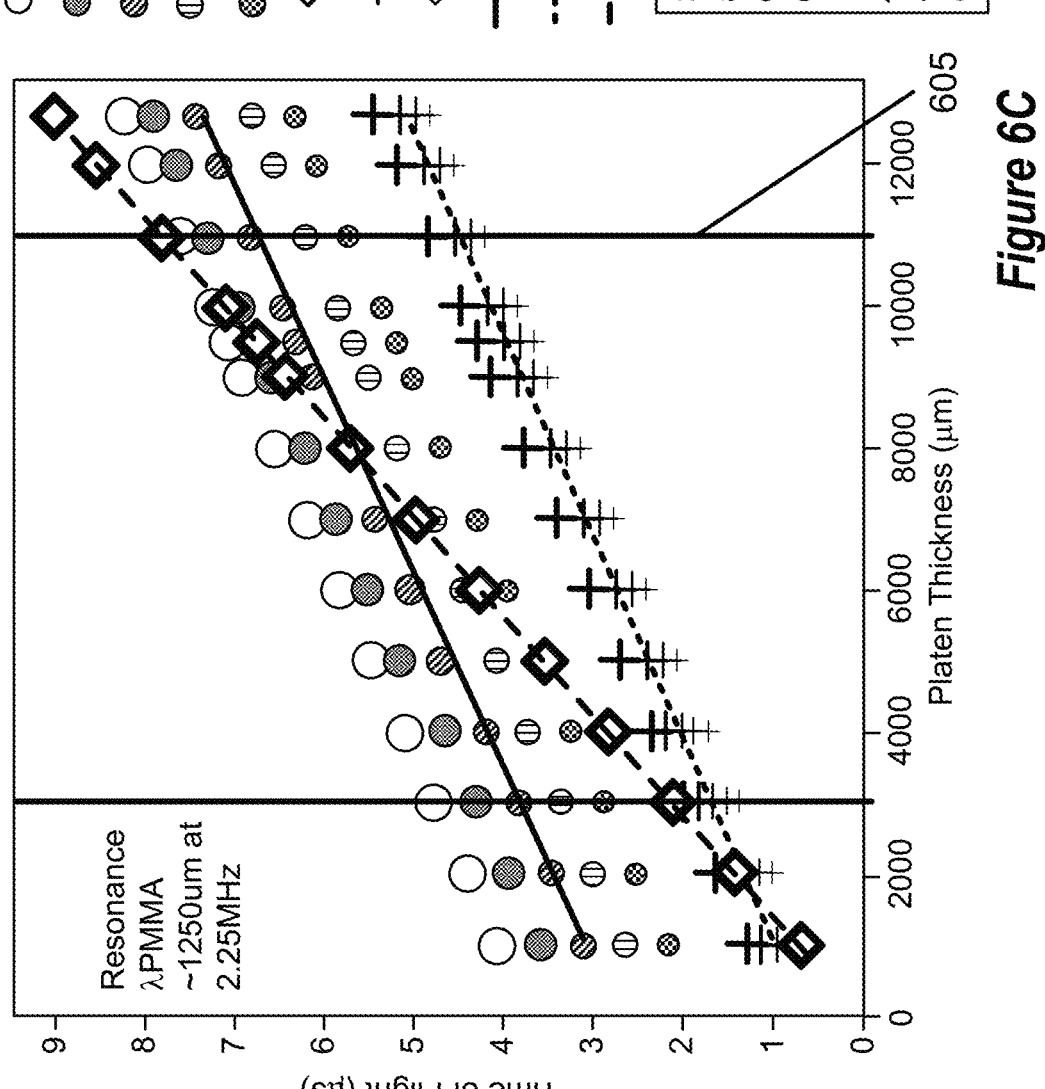
*Figure 6C*

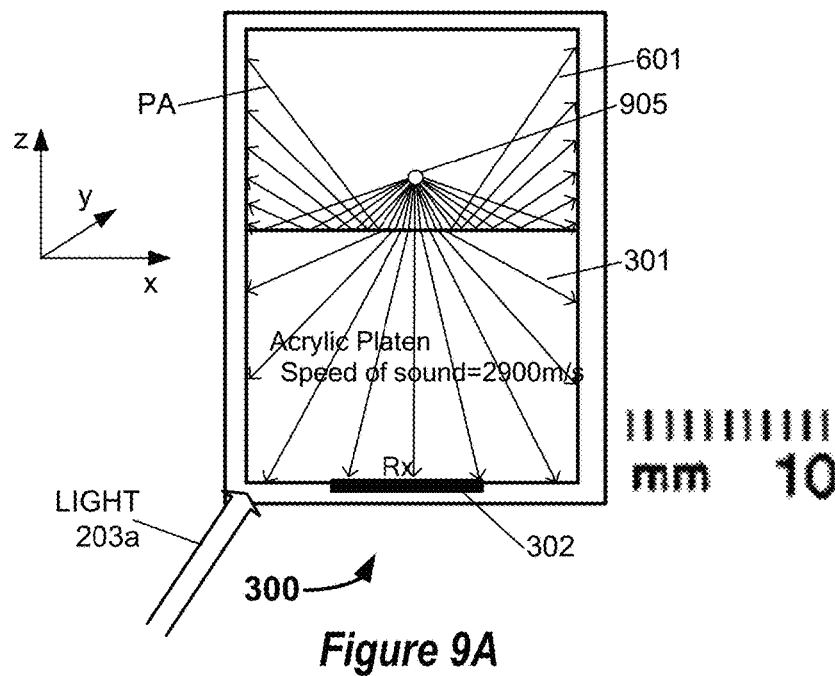
Figure 9A
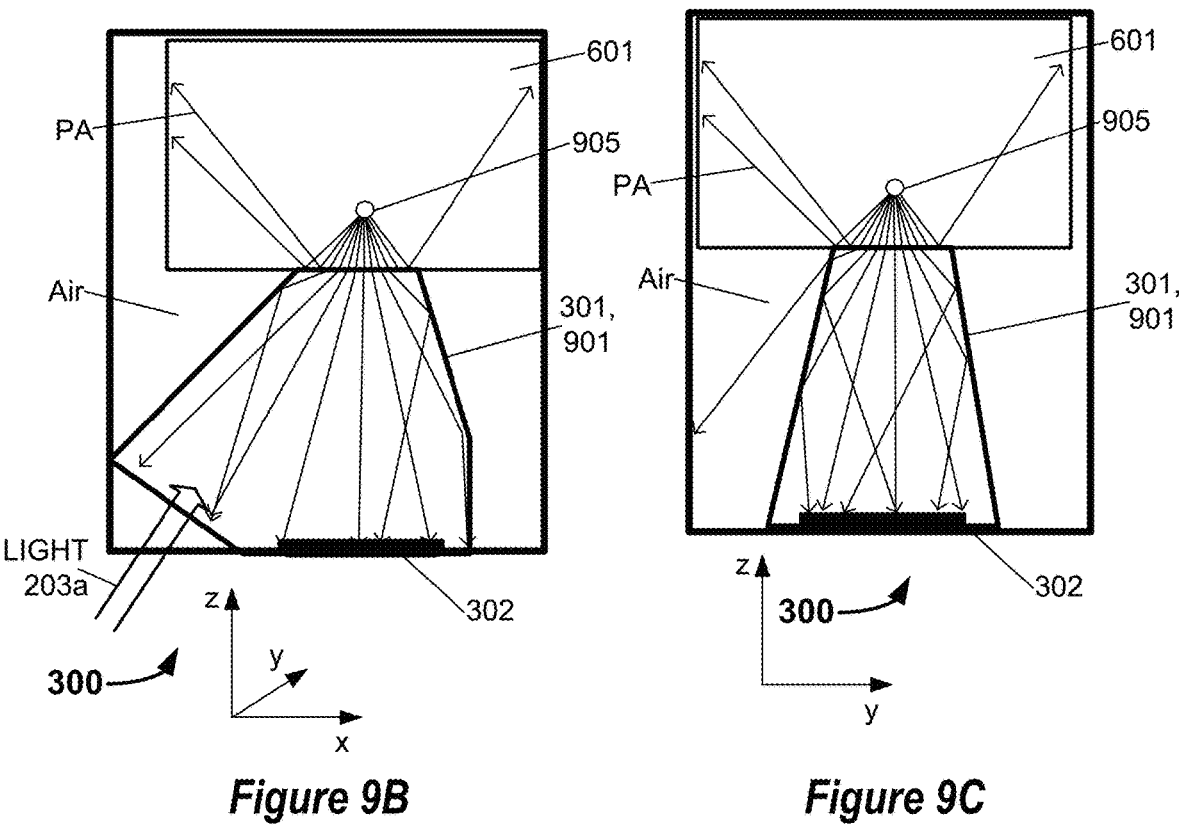
Figure 9B             Figure 9C

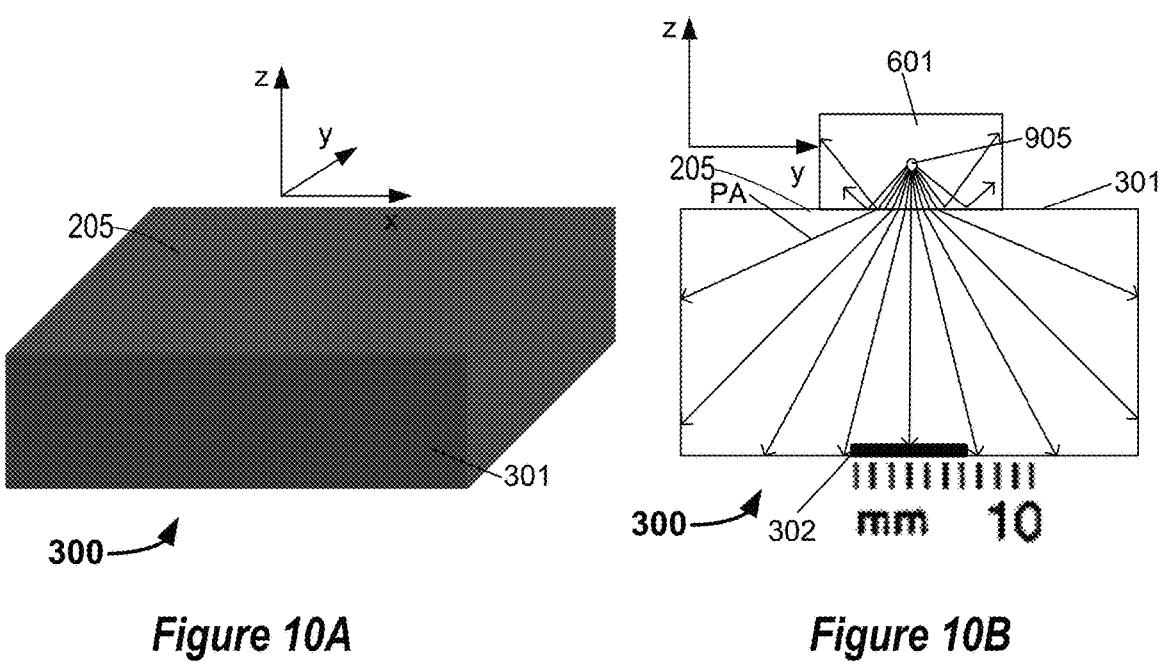
Figure 10A    Figure 10B
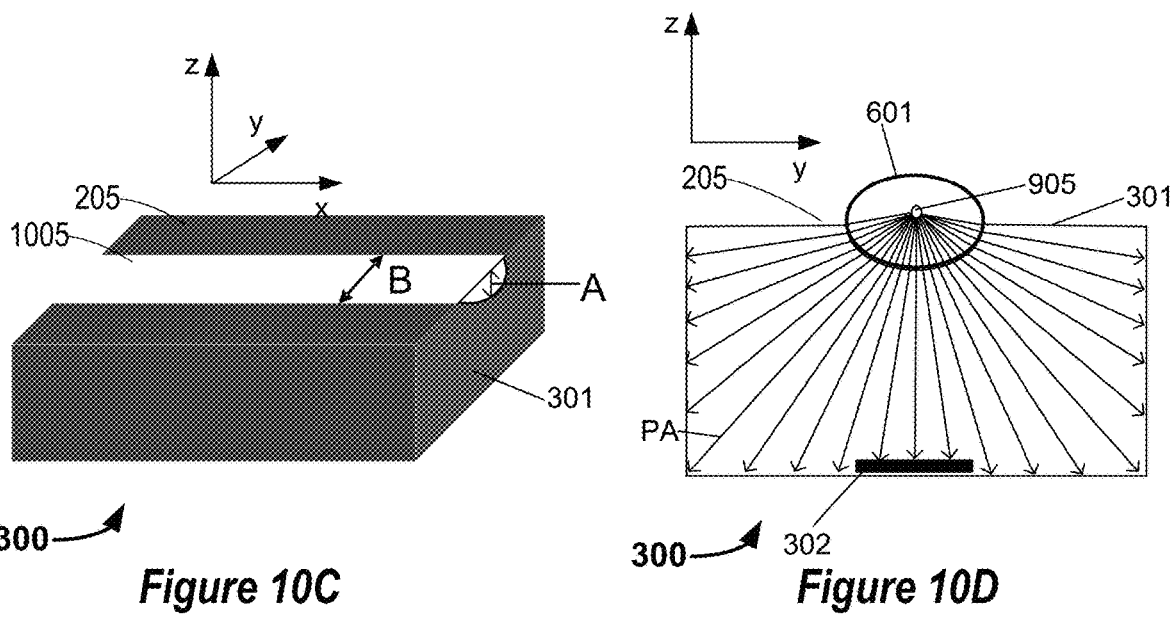
Figure 10C    Figure 10D

Blood Optical Absorption Coefficient vs Wavelength

| Wavelength (nm) | Metric | Maximum Permissible Exposure (MPE) |
|---|---|---|
| 808 | Fluence per Pulse | 0.38 J/cm^2/Pulse |
| | Average Power Density | 0.32 W/cm^2 |
| 940 | Fluence per Pulse | 0.070 J/cm^2/Pulse |
| | Average Power Density | 0.60 W/cm^2 |

1701

1800

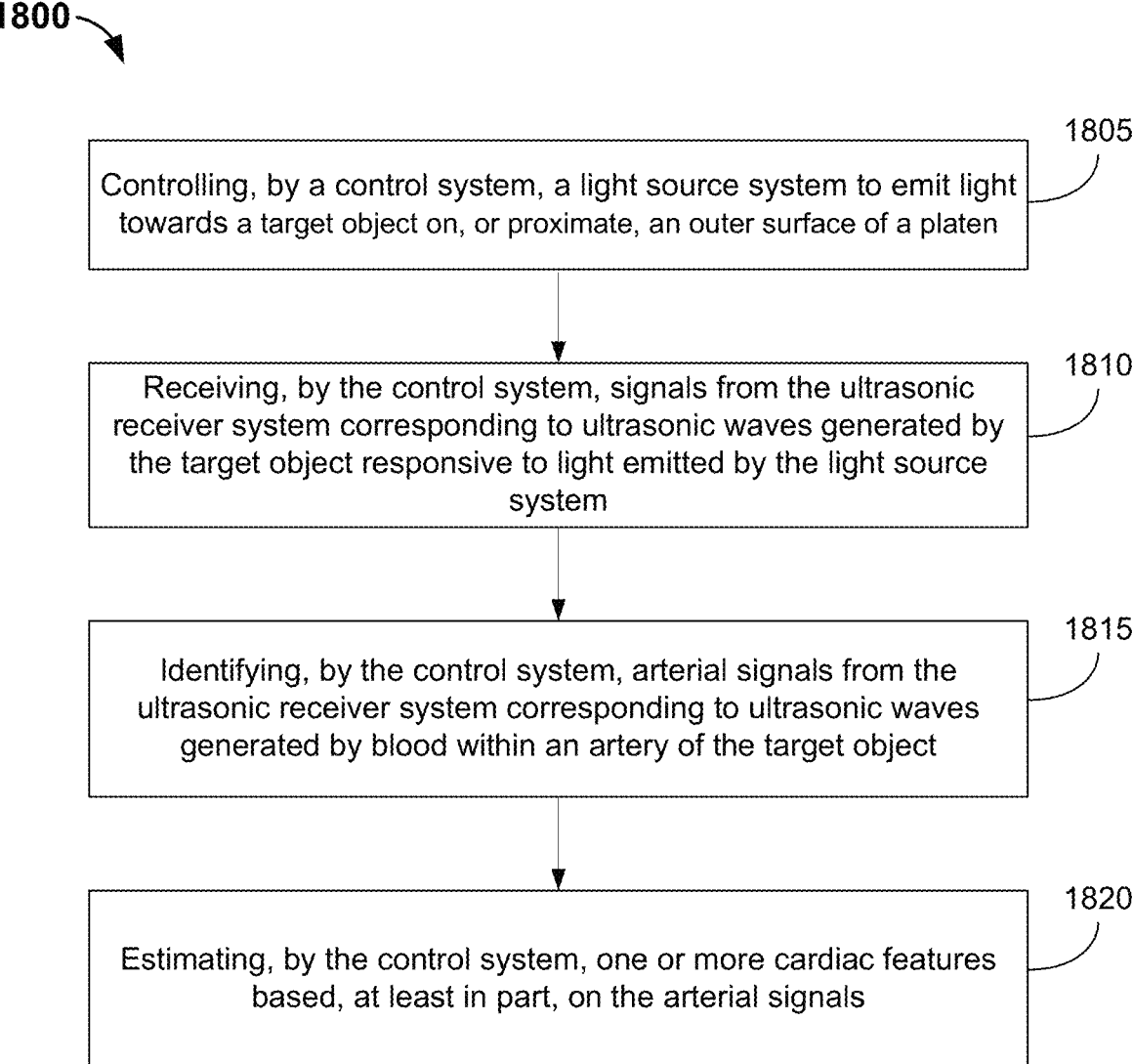

1805

Controlling, by a control system, a light source system to emit light towards a target object on, or proximate, an outer surface of a platen

1810

Receiving, by the control system, signals from the ultrasonic receiver system corresponding to ultrasonic waves generated by the target object responsive to light emitted by the light source system

1815

Identifying, by the control system, arterial signals from the ultrasonic receiver system corresponding to ultrasonic waves generated by blood within an artery of the target object

1820

Estimating, by the control system, one or more cardiac features based, at least in part, on the arterial signals

*Figure 18*

SEMI-COMPACT PHOTOACOUSTIC DEVICES AND SYSTEMS

CROSS-REFERENCE TO RELATED APPLICATIONS

This application is related to U.S. patent application Ser. No. 18/069,859, entitled "PHOTOACOUSTIC DEVICES AND SYSTEMS," to U.S. patent application Ser. No. 18/069,901, entitled "PHOTOACOUSTIC DEVICES AND SYSTEMS INCLUDING ONE OR MORE LIGHT GUIDE COMPONENTS," to U.S. patent application Ser. No. 18/069,882, entitled "SEMI-COMPACT PHOTOACOUS-TIC DEVICES AND SYSTEMS," to U.S. patent application Ser. No. 18/069,885, entitled "SEMI-COMPACT PHO-TOACOUSTIC DEVICES AND SYSTEMS," to U.S. pat-ent application Ser. No. 18/069,888, entitled "SEMI-COM-PACT PHOTOACOUSTIC DEVICES AND SYSTEMS" and to U.S. patent application Ser. No. 18/069,893, entitled "SEMI-COMPACT PHOTOACOUSTIC DEVICES AND SYSTEMS," all of which are hereby incorporated by refer-ence in their entireties and for all purposes.

TECHNICAL FIELD

This disclosure relates generally to photoacoustic devices and systems.

DESCRIPTION OF RELATED TECHNOLOGY

A variety of different sensing technologies and algorithms are being implemented in devices for various biometric and biomedical applications, including health and wellness monitoring. This push is partly a result of the limitations in the usability of traditional measuring devices for continuous, noninvasive and ambulatory monitoring. Some such devices are, or include, photoacoustic devices. Although some pre-viously-deployed photoacoustic devices and systems can provide acceptable results, improved photoacoustic devices and systems would be desirable.

SUMMARY

The systems, methods and devices of this disclosure each have several aspects, no single one of which is solely responsible for the desirable attributes disclosed herein.

One innovative aspect of the subject matter described in this disclosure can be implemented in an apparatus. The apparatus may include a platen, a light source system and an ultrasonic receiver system. In some implementations, a mobile device (such as a wearable device, a cellular tele-phone, etc.) may be, or may include, at least part of the apparatus.

In some examples, the light source system may be con-figured for providing light to a target object on an outer surface of the platen. According to some examples, the ultrasonic receiver system may be configured to receive ultrasonic waves generated by the target object, responsive to the light from the light source system. In some examples, a mirror layer may reside between the ultrasonic receiver system and the platen. The mirror layer may be configured to reflect light from the light source system.

According to some examples, the platen may be config-ured to increase an intensity of ultrasonic energy received by at least a portion of the ultrasonic receiver system. In some examples, the platen may include an acoustic waveguide. According to some examples, the platen may include an acoustic waveguide.

In some examples, the platen may include an acoustic lens. According to some examples, the acoustic lens may reside on, or proximate, the outer surface of the platen. In some examples, the acoustic lens may be a spherical lens or a cylindrical lens.

According to some examples, the platen, the light source system, or a combination thereof, may be configured for transmitting light from the light source system to the outer surface of the platen along a first axis, or substantially along the first axis. In some examples, the platen may be config-ured for transmitting the ultrasonic waves generated by the target object along a second axis, or substantially along the second axis. The second axis may be different from the first axis. According to some examples, the platen may be configured for transmitting the ultrasonic waves generated by the target object along a second axis, or substantially along the second axis. The second axis may be parallel to the first axis.

In some examples, at least one surface of the platen may include an anti-reflective layer. According to some examples, the ultrasonic receiver system may include two or more receiver elements adjacent to a region of the platen through which light from the light source is transmitted towards the target object. In some examples, the platen, the light source system, or a combination thereof, may be configured for transmitting light in the near infrared range.

According to some examples, the apparatus may be, or may include, a mobile device. In some such examples, the outer surface of the platen may correspond with, or may be proximate, an outer surface of the mobile device. In some examples, the mobile device may be, or may include, a cellular telephone. According to some examples, the mobile device may be, or may include, a pen or a stylus. In some examples, the pen or the stylus may include a force sensor, a motion sensor, a spring, or combinations thereof.

In some examples, a thickness of the platen, an acoustic velocity of the platen, or a combination thereof, may be configured to separate ultrasonic waves generated by blood in an artery from other ultrasonic waves. According to some examples, the platen may provide an acoustic attenuation of the ultrasonic waves in a range from 0.3-3.0 decibels per centimeter per megahertz. In some examples, at least an outer surface of the platen has an acoustic impedance that is configured to approximate an acoustic impedance of human skin. According to some examples, at least an outer surface of the platen may be configured to conform to a surface of human skin. In some examples, a speed of sound in the platen may be in a range from 800-3000 meters per second.

According to some examples, the apparatus may include one or more optical waveguides. In some examples, at least a portion of one of the one or more optical waveguides may reside in a portion of the platen.

According to some examples, an apparatus may include a platen and a light source system configured for providing light to a target object on an outer surface of the platen. The light source system may include one or more laser diodes and a drive circuit. In some examples, the apparatus may include an ultrasonic receiver system configured to receive ultrasonic waves generated by the target object, responsive to the light from the light source system. In some examples, the apparatus may include a noise reduction system includ-ing one or more noise reduction elements configured to at least partially decouple acoustic energy produced by the light source system, electrical energy produced by the light source system, light produced by the light source system, or combinations thereof, from the ultrasonic receiver system.

In some examples, the noise reduction system may include one or more electromagnetically shielded transmission wires of the light source system. According to some examples, the one or more electromagnetically shielded transmission wires may be configured to reduce electromagnetic interference from the light source system that is received by the ultrasonic receiver system. According to some examples, the noise reduction system may include one or more air gaps between the light source system and the ultrasonic receiver system. In some examples, the noise reduction system may include one or more sound-absorbing layers configured to reduce the acoustic energy produced by the light source system that is received by the ultrasonic receiver system. According to some examples, at least one of the one or more sound-absorbing layers may reside in, or proximate, the ultrasonic receiver system. In some examples, at least one of the one or more sound-absorbing layers may reside in, or proximate, the light source system. According to some examples, the noise reduction system may include one or more light-absorbing layers configured to reduce an amount of light produced by the light source system that is received by the ultrasonic receiver system. In some such examples, at least one of the one or more light-absorbing layers may reside in, or proximate, the ultrasonic receiver system.

According to some examples, the noise reduction system may include one or more reflective layers configured to reduce an amount of light produced by the light source system that is received by the ultrasonic receiver system. In some examples, at least one of the one or more reflective layers may reside between the platen and at least a portion of the ultrasonic receiver system.

In some examples, the light source system may include at least one multi-junction laser diode. According to some examples, the light source system may include a lens configured to collimate light produced by the light source system.

In some examples, the platen, the light source system, or a combination thereof, may be configured for transmitting light from the light source system to the outer surface of the platen along a first axis, or substantially along the first axis. According to some examples, the platen may be configured for transmitting the ultrasonic waves generated by the target object along a second axis, or substantially along the second axis, the second axis may be different from the first axis. In some examples, the platen may be configured for transmitting the ultrasonic waves generated by the target object along a second axis, or substantially along the second axis, the second axis may be parallel to the first axis. According to some examples, the ultrasonic receiver system may include two or more receiver elements adjacent to a region of the platen through which light from the light source system is transmitted towards the target object.

According to some examples, the light source system may be configured for transmitting light in a wavelength range of 500 to 1000 nanometers. In some such examples, the light source system may be configured for transmitting light in a wavelength range of 500 to 600 nanometers, a wavelength range of 800 to 950 nanometers, or both. In some examples, the light source system may include one or more light-emitting diodes, one or more vertical cavity surface-emitting lasers, one or more edge emitting lasers, or combinations thereof. According to some examples, the drive circuit may be configured to cause the light source system to emit pulses of light at pulse widths in a range from 3 nanoseconds to 1000 nanoseconds. In some examples, the drive circuit may be configured to cause the light source system to emit pulses of light at pulse repetition frequencies in a range from 1 kilohertz to 100 kilohertz.

In some examples, the apparatus may be, or may include, a mobile device. In some examples, the outer surface of the platen may correspond with, or may be proximate, an outer surface of the mobile device. In some examples, the mobile device may be, or may include, a cellular telephone. According to some examples, the mobile device may be, or may include, a pen or a stylus. In some examples, the pen or the stylus may include a force sensor, a motion sensor, a spring, or combinations thereof.

According to some examples, the apparatus may include one or more optical waveguides. According to some examples, at least a portion of one of the one or more optical waveguides may reside in a portion of the platen.

In some examples, an apparatus may include a platen and a light source system configured for providing light to a target object on an outer surface of the platen. The light source system may include one or more laser diodes and a drive circuit. The one or more laser diodes may include at least one multi-junction laser diode. In some examples, the apparatus may include an ultrasonic receiver system configured to receive ultrasonic waves generated by the target object, responsive to the light from the light source system.

According to some examples, the apparatus also may include a noise reduction system including one or more noise reduction elements configured to at least partially decouple acoustic energy produced by the light source system, electrical energy produced by the light source system, light produced by the light source system, or combinations thereof, from the ultrasonic receiver system. In some examples, the one or more electromagnetically shielded transmission wires may be configured to reduce electromagnetic interference from the light source system that is received by the ultrasonic receiver system. According to some examples, the noise reduction system may include one or more air gaps between the light source system and the ultrasonic receiver system.

In some examples, the noise reduction system may include one or more sound-absorbing layers configured to reduce the acoustic energy produced by the light source system that is received by the ultrasonic receiver system. According to some examples, at least one of the one or more sound-absorbing layers may reside in, or proximate, the ultrasonic receiver system. In some examples, at least one of the one or more sound-absorbing layers may reside in, or proximate, the light source system.

According to some examples, the noise reduction system may include one or more light-absorbing layers configured to reduce an amount of light produced by the light source system that is received by the ultrasonic receiver system. In some examples, at least one of the one or more light-absorbing layers may reside in, or proximate, the ultrasonic receiver system. According to some examples, the noise reduction system may include one or more reflective layers configured to reduce an amount of light produced by the light source system that is received by the ultrasonic receiver system. At least one of the one or more reflective layers may reside between the platen and at least a portion of the ultrasonic receiver system.

In some examples, the light source system may include a lens configured to collimate light produced by the light source system. According to some examples, the platen, the light source system, or a combination thereof, may be configured for transmitting light from the light source system to the outer surface of the platen along a first axis, or substantially along the first axis. In some examples, the platen may be configured for transmitting the ultrasonic waves generated by the target object along a second axis, or substantially along the second axis. The second axis may be different from the first axis. According to some examples, the platen may be configured for transmitting the ultrasonic waves generated by the target object along a second axis, or substantially along the second axis. The second axis may be parallel to the first axis.

In some examples, the ultrasonic receiver system may include two or more receiver elements adjacent to a region of the platen through which light from the light source system is transmitted towards the target object.

According to some examples, the light source system may be configured for transmitting light in a wavelength range of 500 to 1000 nanometers. In some such examples, the light source system may be configured for transmitting light in a wavelength range of 500 to 600 nanometers, a wavelength range of 800 to 950 nanometers, or both. In some examples, the light source system may include one or more light-emitting diodes, one or more vertical cavity surface-emitting lasers, one or more edge emitting lasers, or combinations thereof. According to some examples, the drive circuit may be configured to cause the light source system to emit pulses of light at pulse widths in a range from 3 nanoseconds to 1000 nanoseconds. In some examples, the drive circuit may be configured to cause the light source system to emit pulses of light at pulse repetition frequencies in a range from 1 kilohertz to 100 kilohertz.

According to some examples, the mobile device may be, or may include, a cellular telephone. In some examples, the mobile device may be, or may include, a pen or a stylus. According to some examples, the pen or the stylus may include a force sensor, a motion sensor, a spring, or combinations thereof.

In some examples, the apparatus may include one or more optical waveguides. According to some examples, at least a portion of one of the one or more optical waveguides may reside in a portion of the platen.

In some examples, the apparatus may include a platen, a light source system configured for providing light to a target object on an outer surface of the platen, and an ultrasonic receiver configured to receive ultrasonic waves generated by the target object, responsive to the light from the light source system. According to some examples, one or more platen characteristics that include a thickness of the platen, an acoustic velocity of the platen, or a combination thereof, may be configured to separate received one or more arterial ultrasonic waves generated by blood in an artery, by an arterial wall, or by a combination thereof, from one or more other types of received ultrasonic waves.

In some examples, the one or more other types of received ultrasonic waves include reflected ultrasonic waves emitted by the ultrasonic receiver that have reflected from the target object. According to some examples, the one or more platen characteristics cause the reflected ultrasonic waves emitted by the ultrasonic receiver to be received by the ultrasonic receiver after the one or more arterial ultrasonic waves.

In some examples, a speed of sound in the platen may be in a range from 800-3000 meters per second. According to some examples, the thickness of the platen may be in a range from 5-40 millimeters. In some examples, the platen may be configured to increase an intensity of ultrasonic energy received by at least a portion of the ultrasonic receiver. According to some examples, the platen may include an acoustic waveguide. In some examples, the platen may include an acoustic lens. The acoustic lens may reside on, or proximate, the outer surface of the platen. According to some examples, the acoustic lens may be a spherical lens or a cylindrical lens.

According to some examples, the platen, the light source system, or a combination thereof, may be configured for transmitting light from the light source system to the outer surface of the platen along a first axis, or substantially along the first axis. In some examples, the platen may be configured for transmitting the ultrasonic waves generated by the target object along a second axis, or substantially along the second axis, the second axis may be different from the first axis. According to some examples, the platen may be configured for transmitting the ultrasonic waves generated by the target object along a second axis, or substantially along the second axis, the second axis may be parallel to the first axis.

In some examples, the ultrasonic receiver may include two or more receiver elements adjacent to a region of the platen through which light from the light source is transmitted towards the target object. According to some examples, the platen, the light source system, or a combination thereof, may be configured for transmitting light in the near infrared range.

According to some examples, the apparatus may be, or may include, a mobile device and wherein the outer surface of the platen may correspond with, or may be proximate, an outer surface of the mobile device. According to some examples, the mobile device may be, or may include, a cellular telephone. In some examples, the mobile device may be, or may include, a pen or a stylus. According to some examples, the pen or the stylus may include a force sensor, a motion sensor, a spring, or combinations thereof.

In some examples, the platen may provide an acoustic attenuation of the ultrasonic waves in a range from 0.3-6.0 decibels per centimeter per megahertz. In some examples, the ultrasonic waves received by the ultrasonic receiver may be in a range from 0.5 MHz to 1.5 MHz and wherein the platen may provide an acoustic attenuation of the ultrasonic waves in a range from 0.3-12.0 decibels per centimeter per megahertz. In some examples, a portion of the platen may reside between the outer surface and the ultrasonic receiver has a thickness in a range from 0.25 cm to 0.75 cm. According to some examples, the ultrasonic waves received by the ultrasonic receiver may be in a range from 1.5 MHz to 3.0 MHz and wherein the platen may provide an acoustic attenuation of the ultrasonic waves in a range from 0.3-3.0 decibels per centimeter per megahertz. In some examples, a portion of the platen residing between the outer surface and the ultrasonic receiver may have a thickness in a range from 0.5 cm to 2.0 cm. According to some examples, the ultrasonic waves received by the ultrasonic receiver may be in a range from 3.0 MHz to 7.0 MHz. In some such examples, the platen may provide an acoustic attenuation of the ultrasonic waves in a range from 0.3-3.0 decibels per centimeter per megahertz. In some examples, a portion of the platen residing between the outer surface and the ultrasonic receiver may have a thickness in a range from 2.0 cm to 6.0 cm.

According to some examples, the ultrasonic waves received by the ultrasonic receiver may be in a range from 7.0 MHz to 13.0 MHz. In some such examples, the platen may provide an acoustic attenuation of the ultrasonic waves of less than 0.15 decibels per centimeter per megahertz. In some examples, a portion of the platen residing between the outer surface and the ultrasonic receiver may have a thickness in a range from 2.0 cm to 6.0 cm.

According to some examples, at least an outer surface of the platen has an acoustic impedance that may be configured to approximate an acoustic impedance of human skin. In some examples, at least an outer surface of the platen may be configured to conform to a surface of human skin.

In some examples, at least one surface of the platen may include an anti-reflective layer or have an anti-reflective layer proximate the at least one surface.

According to some examples, the apparatus may include one or more optical waveguides. In some such examples, at least a portion of one of the one or more optical waveguides may reside in a portion of the platen.

In some examples, an apparatus may include a platen having an outer surface with an acoustic impedance that is configured to approximate the acoustic impedance of human skin. According to some examples, the outer surface may be configured to conform to a surface of the human skin. In some examples, the apparatus may include a light source system configured for providing light to a target object on, or proximate, an outer surface of the platen. In some examples, the apparatus may include an ultrasonic receiver configured to receive ultrasonic waves generated by the target object, responsive to the light from the light source system.

According to some examples, the acoustic impedance of the outer surface may be within a range of plus or minus 5% of the acoustic impedance of human skin. In some examples, the acoustic impedance of the outer surface may be within a range of plus or minus 10% of the acoustic impedance of human skin. According to some examples, the acoustic impedance of the outer surface may be within a range of 1.4 MRayl-1.7 MRayl.

In some examples, the outer surface may be configured to conform to ridges and valleys of a finger pad. According to some examples, the outer surface may be configured to releasably adhere to the surface of the human skin.

According to some examples, the platen may be configured to increase an intensity of ultrasonic energy received by at least a portion of the ultrasonic receiver. In some examples, the platen may include an acoustic waveguide. According to some examples, the platen may include an acoustic lens. In some examples, the acoustic lens may reside on, or proximate, the outer surface of the platen. According to some examples, the acoustic lens may be a spherical lens or a cylindrical lens.

In some examples, the platen, the light source system, or a combination thereof, may be configured for transmitting light from the light source system to the outer surface of the platen along a first axis, or substantially along the first axis. According to some examples, the platen may be configured for transmitting the ultrasonic waves generated by the target object along a second axis, or substantially along the second axis. The second axis may be different from the first axis. According to some examples, the platen may be configured for transmitting the ultrasonic waves generated by the target object along a second axis, or substantially along the second axis. The second axis may be parallel to the first axis.

In some examples, the ultrasonic receiver may include two or more receiver elements adjacent to a region of the platen through which light from the light source is transmitted towards the target object.

According to some examples, the light source system may be configured for transmitting light in a wavelength range of 500 to 1000 nanometers. In some such examples, the light source system may be configured for transmitting light in a wavelength range of 500 to 600 nanometers, a wavelength range of 800 to 950 nanometers, or both. In some examples, the light source system may include one or more light-emitting diodes, one or more vertical cavity surface-emitting lasers, one or more edge emitting lasers, or combinations thereof. According to some examples, the drive circuit may be configured to cause the light source system to emit pulses of light at pulse widths in a range from 3 nanoseconds to 1000 nanoseconds. In some examples, the drive circuit may be configured to cause the light source system to emit pulses of light at pulse repetition frequencies in a range from 1 kilohertz to 100 kilohertz. In some examples, the platen, the light source system, or a combination thereof, may be configured for transmitting light in the near infrared range.

In some examples, the apparatus may be, or may include, a mobile device. In some such examples, the outer surface of the platen may correspond with, or may be proximate, an outer surface of the mobile device. According to some examples, the mobile device may be, or may include, a cellular telephone. In some examples, the mobile device may be, or may include, a pen or a stylus. The pen or the stylus may include a force sensor, a motion sensor, a spring, or combinations thereof.

According to some examples, a thickness of the platen, an acoustic velocity of the platen, or a combination thereof, may be configured to separate ultrasonic waves generated by blood in an artery from other ultrasonic waves. In some examples, the platen may provide an acoustic attenuation of the ultrasonic waves in a range from 0.3-3.0 decibels per centimeter per megahertz. According to some examples, a speed of sound in the platen may be in a range from 800-3000 meters per second. In some examples, at least one surface of the platen may include an anti-reflective layer.

In some examples, the apparatus may include one or more optical waveguides. According to some examples, at least a portion of one of the one or more optical waveguides may reside in a portion of the platen.

In some implementations, the apparatus may include a control system. The control system may include one or more general purpose single- or multi-chip processors, digital signal processors (DSPs), application specific integrated circuits (ASICs), field programmable gate arrays (FPGAs) or other programmable logic devices, discrete gates or transistor logic, discrete hardware components, or combinations thereof.

In some examples, the control system may be configured to control the light source system to emit light. According to some examples, the control system may be configured to receive signals from the ultrasonic receiver system corresponding to the ultrasonic waves generated by the target object. According to some examples, the control system may be configured to identify one or more arterial wall signals from the ultrasonic receiver system corresponding to ultrasonic waves generated by one or more arterial walls of the target object. According to some examples, the control system may be configured to estimate one or more cardiac features based, at least in part, on the one or more arterial wall signals.

According to some examples, the control system may be configured to receive signals from the ultrasonic receiver system corresponding to the ultrasonic waves generated by the target object. According to some examples, the control system may be configured to identify one or more arterial blood signals from the ultrasonic receiver system corresponding to ultrasonic waves generated by blood within an artery of the target object. According to some examples, the control system may be configured to estimate one or more cardiac features based, at least in part, on the one or more arterial blood signals.

In some examples, the control system may be configured to control the light source system to emit light. In some examples, the control system may be configured to receive signals from the ultrasonic receiver system corresponding to the ultrasonic waves generated by the target object. In some examples, the control system may be configured to identify one or more arterial signals from the ultrasonic receiver system corresponding to ultrasonic waves generated by blood within an artery of the target object, generated by one or more arterial walls, or combinations thereof. In some examples, the control system may be configured to In some examples, the control system may be configured to estimate one or more cardiac features based, at least in part, on the one or more arterial signals.

Other innovative aspects of the subject matter described in this disclosure can be implemented in a method. In some examples, the method may involve controlling, by a control system, a light source system to emit light to a target object on an outer surface of a platen. In some examples, the method may involve receiving, by the control system, signals from an ultrasonic receiver system corresponding to the ultrasonic waves generated by a target object. In some examples, the method may involve identifying, by the control system, arterial signals from the ultrasonic receiver system corresponding to ultrasonic waves generated by blood within an artery of the target object, generated by one or more arterial walls of the target object, or a combination thereof. In some examples, the method may involve In some examples, the method may involve estimating, by the control system, one or more cardiac features based, at least in part, on the arterial blood signals. According to some examples, controlling the light source system to emit light may involve controlling the light source system to emit laser pulses.

Some or all of the methods described herein may be performed by one or more devices according to instructions (e.g., software) stored on non-transitory media. Such non-transitory media may include memory devices such as those described herein, including but not limited to random access memory (RAM) devices, read-only memory (ROM) devices, etc. Accordingly, some innovative aspects of the subject matter described in this disclosure can be implemented in one or more non-transitory media having software stored thereon. The software may include instructions for controlling one or more devices to perform one or more disclosed methods.

In some examples, the method may involve controlling, by a control system, a light source system to emit light to a target object on an outer surface of a platen. In some examples, the method may involve receiving, by the control system, signals from an ultrasonic receiver system corresponding to the ultrasonic waves generated by a target object. In some examples, the method may involve identifying, by the control system, arterial signals from the ultrasonic receiver system corresponding to ultrasonic waves generated by blood within an artery of the target object, generated by one or more arterial walls of the target object, or a combination thereof. In some examples, the method may involve In some examples, the method may involve estimating, by the control system, one or more cardiac features based, at least in part, on the arterial blood signals. According to some examples, controlling the light source system to emit light may involve controlling the light source system to emit laser pulses.

Details of one or more implementations of the subject matter described in this disclosure are set forth in the accompanying drawings and the description below. Other features, aspects, and advantages will become apparent from the description, the drawings and the claims. Note that the relative dimensions of the following figures may not be drawn to scale.

BRIEF DESCRIPTION OF THE DRAWINGS

FIG. 6C is a graph that shows examples of times of flight for acoustic waves corresponding to each of the artery sizes and depths shown in FIG. 6B, for a range of platen thicknesses.

FIGS. 9A, 9B and 9C show examples of ray tracing inside a target object and two different types of platen.

FIGS. 10A, 10B, 10C and 10D show examples of two additional types of platen and corresponding ray tracing diagrams.

FIG. 18 is a flow diagram that shows examples of some disclosed operations.

Like reference numbers and designations in the various drawings indicate like elements.

DETAILED DESCRIPTION

Figure 1A:
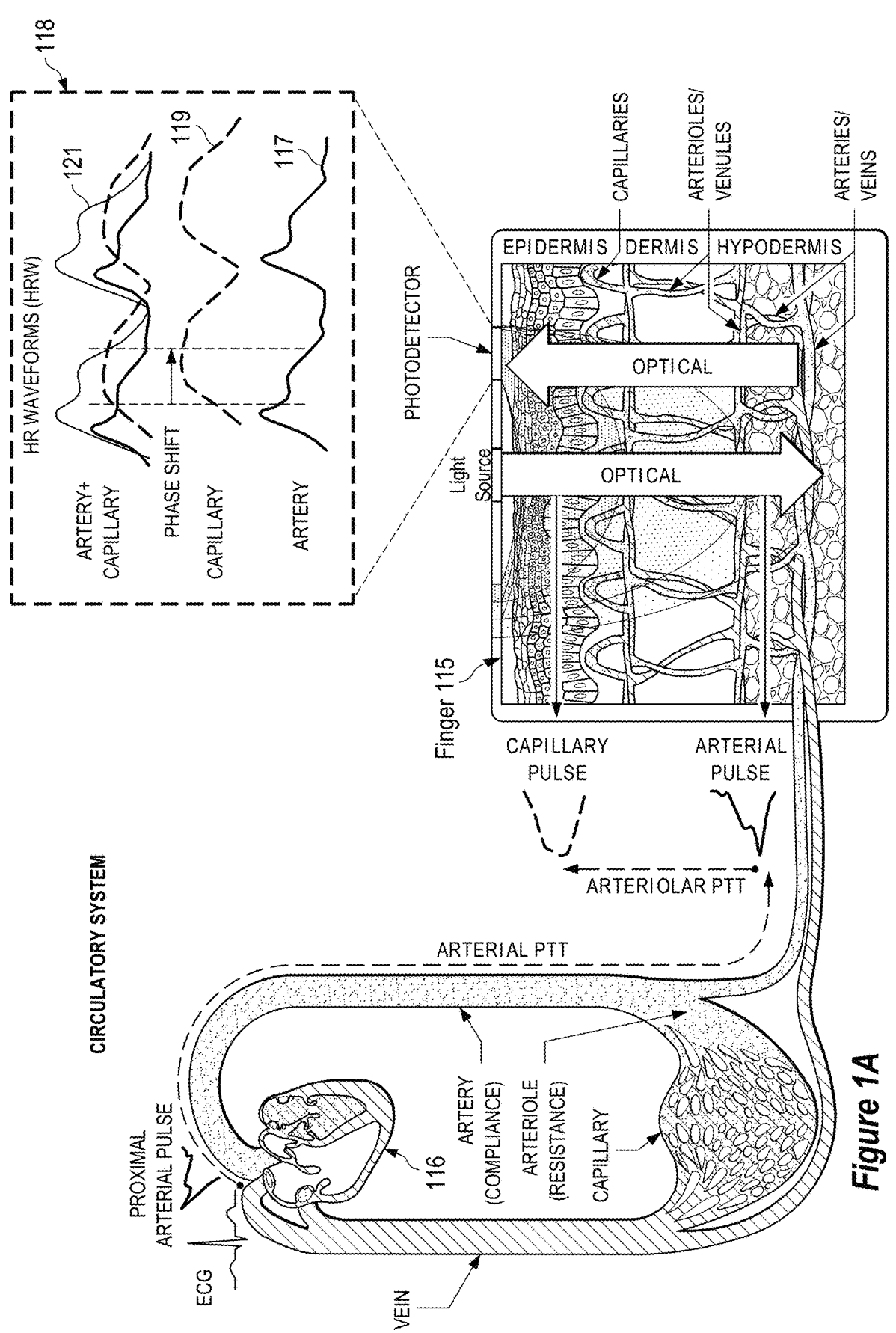
FIG. 1A shows an example of a blood pressure monitoring device based on photoplethysmography (PPG).

The following description is directed to certain implementations for the purposes of describing various aspects of this disclosure. However, a person having ordinary skill in the art will readily recognize that the teachings herein can be applied in a multitude of different ways. Some of the concepts and examples provided in this disclosure are especially applicable to blood pressure monitoring applications. However, some implementations also may be applicable to other types of biological sensing applications, as well as to other fluid flow systems. The described implementations may be implemented in any device, apparatus, or system that includes an apparatus as disclosed herein. In addition, it is contemplated that the described implementations may be included in or associated with a variety of electronic devices such as, but not limited to: mobile telephones, multimedia Internet enabled cellular telephones, mobile television receivers, wireless devices, smartphones, smart cards, wearable devices such as bracelets, armbands, wristbands, rings, headbands, patches, etc., Bluetooth® devices, personal data assistants (PDAs), wireless electronic mail receivers, handheld or portable computers, netbooks, notebooks, smartbooks, tablets, printers, copiers, scanners, facsimile devices, global positioning system (GPS) receivers/navigators, cameras, digital media players, game consoles, wrist watches, clocks, calculators, television monitors, flat panel displays, electronic reading devices (e.g., e-readers), mobile health devices, computer monitors, auto displays (including odometer and speedometer displays, etc.), cockpit controls and/or displays, camera view displays (such as the display of a rear view camera in a vehicle), architectural structures, microwaves, refrigerators, stereo systems, cassette recorders or players, DVD players, CD players, VCRs, radios, portable memory chips, washers, dryers, washer/dryers, parking meters, automobile doors, autonomous or semi-autonomous vehicles, drones, Internet of Things (IOT) devices, etc. Thus, the teachings are not intended to be limited to the specific implementations depicted and described with reference to the drawings; rather, the teachings have wide applicability as will be readily apparent to persons having ordinary skill in the art.

In recent years, a variety of different devices for biometric and biomedical applications, including health and wellness monitoring, biometric authentication, etc., have appeared on the marketplace. Some such devices include light sources, such as light sources that include one or more lasers. For example, some health monitoring systems and some biometric authentication systems may be configured to illuminate a target with high-intensity light for liveness detection, such as for cardiac pulse detection. Some devices may be configured to illuminate a target with high-intensity light for blood oxygen estimation, heart rate monitoring, blood pressure monitoring, etc. Some such devices may illuminate a target with high-intensity light for blood pressure monitoring based on photoplethysmography (PPG) or photoacoustic plethysmography (PAPG).

Non-invasive health monitoring devices, such as PAPG-based devices, have various potential advantages over more invasive health monitoring devices such as cuff-based or catheter-based blood pressure measurement devices. However, it has proven to be difficult to design satisfactory compact, or semi-compact, PAPG-based devices. (Some "semi-compact" devices may have a length in the range of 5.0 mm to 40 mm. Some semi-compact devices may have a cross-sectional area in the range of 6.0 mm² to 50 mm². A "compact" device is a device that is smaller than a semi-compact device.) For example, some previously-deployed PAPG-based devices have produced various types of artifact signals, including but not limited to electromagnetic interference (EMI) signals, signals from reflected light and signals from reflected acoustic waves. Such artifact signals can obscure desired signals, such as signals corresponding to a blood vessel or to blood within a blood vessel.

Some disclosed devices include a platen, a light source system and an ultrasonic receiver system. In some implementations, the platen may be configured to separate one or more received arterial ultrasonic waves generated by blood in an artery, by an arterial wall, or by a combination thereof, from one or more other types of received ultrasonic waves. According to some implementations, the platen may have an outer surface with an acoustic impedance that is configured to approximate the acoustic impedance of human skin. In some such implementations, the outer surface of the platen may be configured to conform to a surface of the human skin.

Some disclosed implementations may include a noise reduction system. According to some implementations, the light source system may include at least one multi-junction laser diode. Some disclosed implementations may include a mirror layer residing between the ultrasonic receiver system and the platen.

Particular implementations of the subject matter described in this disclosure can be implemented to realize one or more of the following potential advantages. In some implementations, a noise reduction system may be configured to at least partially decouple acoustic energy produced by the light source system, electrical energy produced by the light source system, light produced by the light source system, or combinations thereof, from the ultrasonic receiver system. Such implementations may increase the signal-to-noise ratio of desired signals. Implementations in which the light source system includes at least one multi-junction laser diode may also reduce noise and increase the signal-to-noise ratio of desired signals. According to some implementations, arterial ultrasonic waves may be more readily detectible, because the platen may be configured to separate received arterial ultrasonic waves from one or more other types of received ultrasonic waves. In some implementations that include a mirror layer, the mirror layer may be configured to reflect light from the light source system away from the ultrasonic receiver system, thereby mitigating another type of noise.

FIG. 1A shows an example of a blood pressure monitoring device based on photoplethysmography (PPG). FIG. 1A shows examples of arteries, veins, arterioles, venules and capillaries of a circulatory system, including those inside a finger 115. In the example shown in FIG. 1A, an electrocardiogram (ECG) sensor has detected a proximal arterial pulse near the heart 116. Some examples are described below of measurement of the arterial pulse transit time (PTT) according to arterial pulses measured by two sensors, one of which may be an electrocardiogram sensor in some implementations.

According to the example shown in FIG. 1A, a light source that includes one or more lasers or light-emitting diodes (LEDs) has transmitted light (in some examples, green, red, and/or near-infrared (NIR) light) that has penetrated the tissues of the finger 115 in an illuminated zone. Reflections from these tissues, detected by the photodetector, may be used to detect volumetric changes in the blood of the illuminated zone of the finger 115 that correspond to heart rate waveforms.

As shown in the heart rate waveform graphs 118 of FIG. 1A, the capillary heart rate waveform 119 is differently-shaped and phase-shifted relative to the artery heart rate waveform 117. In this simple example, the detected heart rate waveform 121 is a combination of the capillary heart rate waveform 119 and the artery heart rate waveform 117. In some instances, the responses of one or more other blood vessels may also be part of the heart rate waveform 121 detected by a PPG-based blood pressure monitoring device. PPG-based blood pressure monitoring devices are not optimal because PPG superimposes data corresponding to the blood volume of all illuminated blood vessels, each of which exhibit different and time-shifted blood volume changes. Nonetheless, there are many deployed PPG-based blood pressure monitoring devices.

Figure 1B:
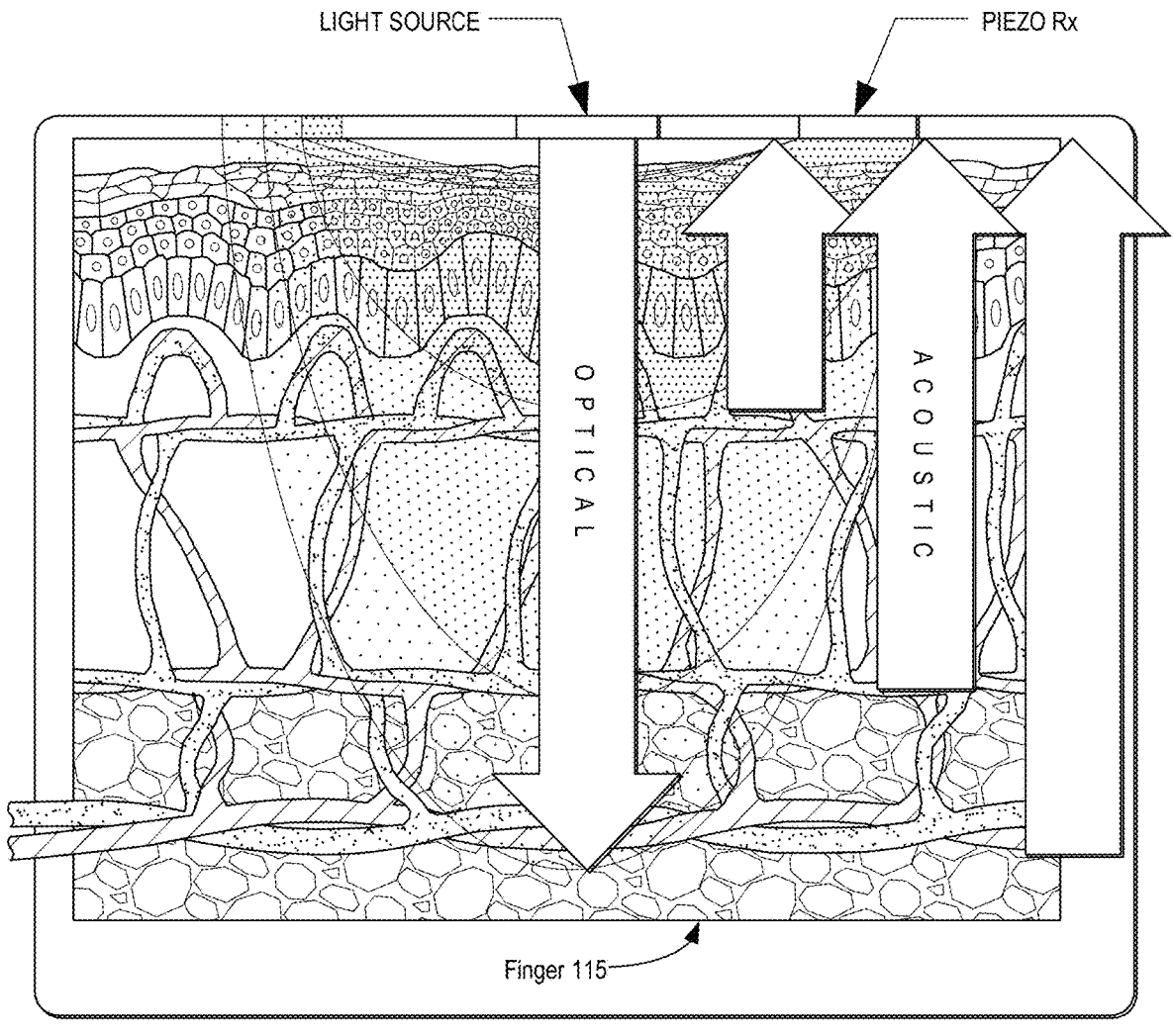
FIG. 1B shows an example of a blood pressure monitoring device based on photoacoustic plethysmography, which may be referred to herein as PAPG.

FIG. 1B shows an example of a blood pressure monitoring device based on photoacoustic plethysmography, which may be referred to herein as PAPG. FIG. 1B shows the same examples of arteries, veins, arterioles, venules and capillaries inside the finger 115 that are shown in FIG. 1A. In some examples, the light source shown in FIG. 1B may be, or may include, one or more LEDs, one or more laser diodes, etc. In this example, as in FIG. 1A, the light source has transmitted light (in some examples, green, red, and/or near-infrared (NIR) light) that has penetrated the tissues of the finger 115 in an illuminated zone.

In the example shown in FIG. 1B, blood vessels (and components of the blood itself) are heated by the incident light from the light source and are emitting acoustic waves. In this example, the emitted acoustic waves include ultrasonic waves. According to this implementation, the acoustic wave emissions are being detected by an ultrasonic receiver, which is a piezoelectric receiver in this example. Photoacoustic emissions from the illuminated tissues, detected by the piezoelectric receiver, may be used to detect volumetric changes in the blood of the illuminated zone of the finger 115 that correspond to heart rate waveforms. Although some of the tissue areas shown to be illuminated are offset from those shown to be producing photoacoustic emissions, this is merely for illustrative convenience. It will be appreciated that that the illuminated tissues will actually be those producing photoacoustic emissions. Moreover, it will be appreciated that the maximum levels of photoacoustic emissions will often be produced along the same axis as the maximum levels of illumination. In some examples, the ultrasonic receiver may be an instance of the receiver system 202 that is described below with reference to FIG. 2.

One important difference between the PPG-based system of FIG. 1A and the PAPG-based method of FIG. 1B is that the acoustic waves shown in FIG. 1B travel much more slowly than the reflected light waves shown in FIG. 1A. Accordingly, depth discrimination based on the arrival times of the acoustic waves shown in FIG. 1B is possible, whereas depth discrimination based on the arrival times of the light waves shown in FIG. 1A may not be possible. This depth discrimination allows some disclosed implementations to isolate acoustic waves received from the different blood vessels.

According to some such examples, such depth discrimination allows artery heart rate waveforms to be distinguished from vein heart rate waveforms and other heart rate waveforms. Therefore, blood pressure estimation based on depth-discriminated PAPG methods can be substantially more accurate than blood pressure estimation based on PPG-based methods.

Figure 2A:
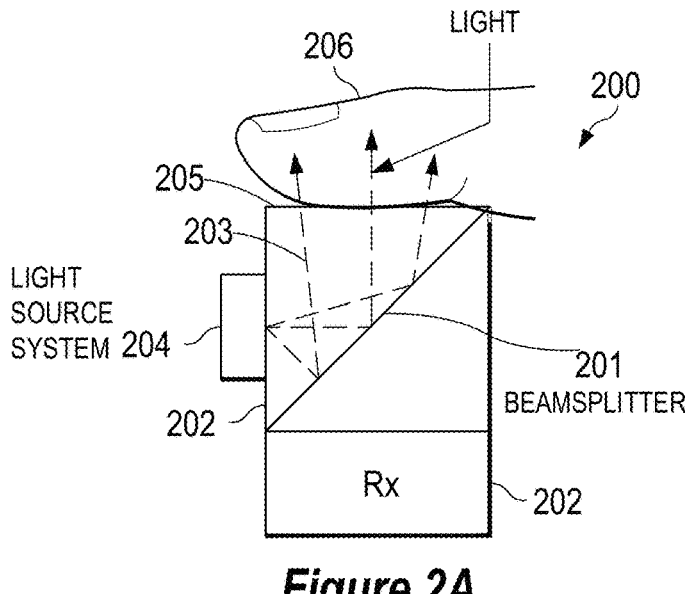
FIGS. 2A, 2B and 2C show examples of devices configured to receive acoustic waves emitted from different depths.
Figure 2B:
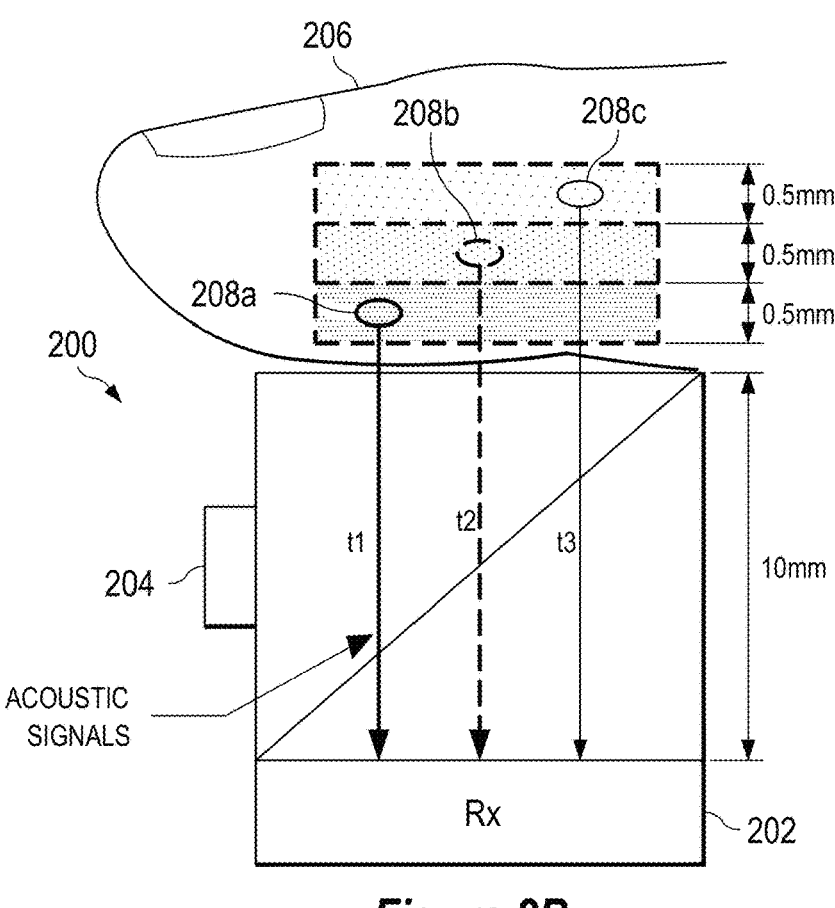
Figure 2C:
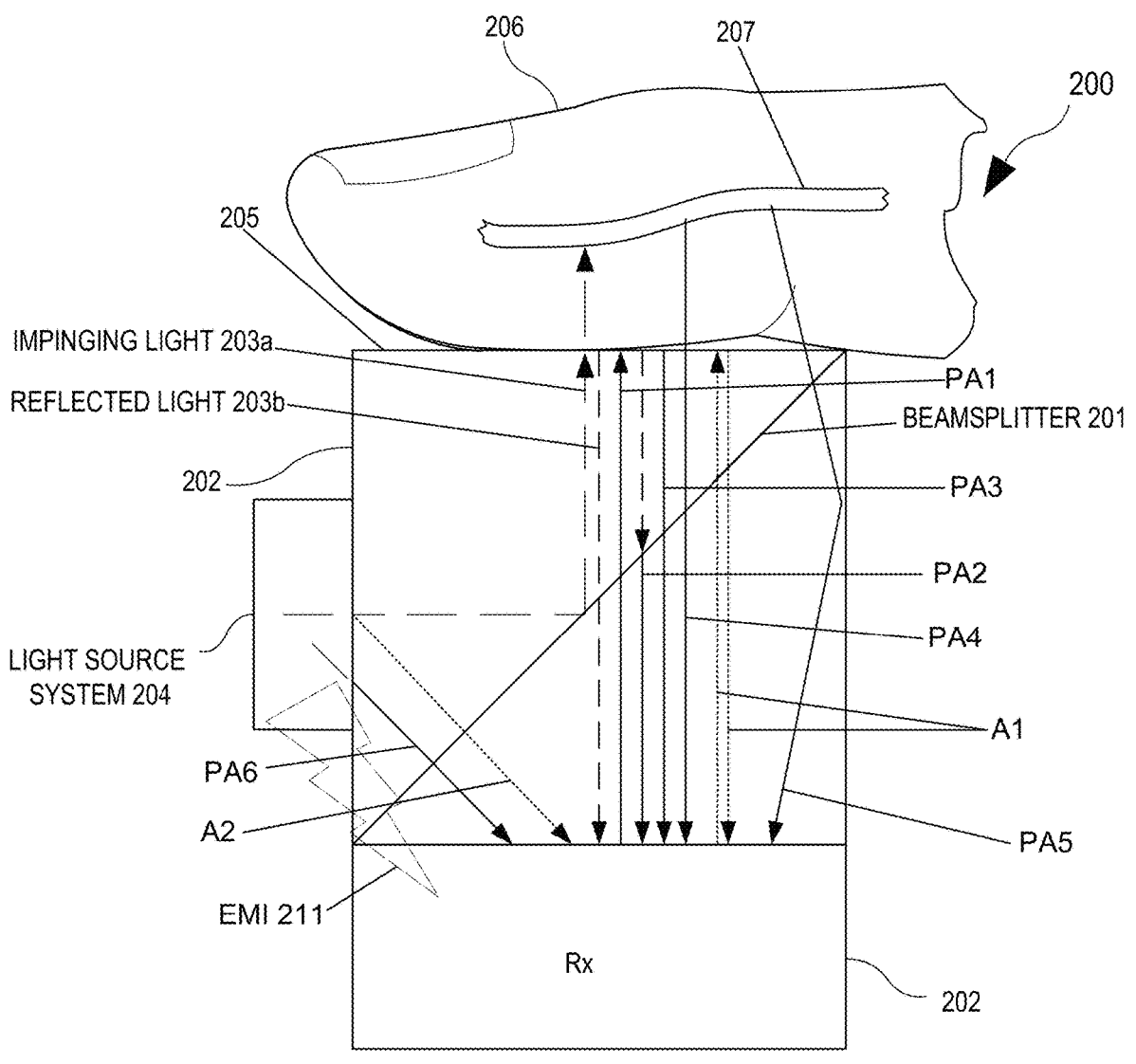

FIGS. 2A, 2B and 2C show examples of devices configured to receive acoustic waves emitted from different depths. As with the other implementations shown and described herein, the types of elements, the arrangement of the elements and the dimensions of the elements illustrated in FIGS. 2A-2C are merely shown by way of example.

According to these examples, the apparatus 200 includes an ultrasonic receiver 202, a light source system 204 (which includes an LED in this example) and a control system (which is not shown in FIGS. 2A-2C). According to these examples, the apparatus 200 includes a beamsplitter 201 inside of a platen 202 to which the light source system 204 is mounted. In this instance, a finger 206 rests upon an outer surface 205 of the apparatus 200.

FIG. 2A shows light 203 emitted from the light source system 204. Part of the light 203 is reflected by the beamsplitter 201 and enters the finger 206. The range gate delay (RGD) for this implementation and other implementations may, for example, be selected to correspond with the time required for photoacoustic emissions from a shallowest target of interest to reach a receiver. For example, in one configuration of the apparatus 200 which uses a 12.7 mm beamsplitter between the finger 206 and the ultrasonic receiver 202 (RX in FIG. 2A), the finger surface signal will arrive at the time it takes the acoustic waves to travel through the entire beamsplitter. Using the speed of sound of borosilicate glass of 5500 m/s as an approximate speed of sound for the beamsplitter and with the beamsplitter size of 12.7 mm, this time becomes 12.7 mm/5500 m/s or 2.3 μs. Therefore, a range gate delay of 2.3 us corresponds to the surface of the finger 206. To travel 1 mm into the finger 206, for example, using the speed of sound for tissue now of 1.5 mm/μs, this time becomes 1 mm/1.5 mm/μs or ~0.67 μs. Therefore, a range gate delay of ~2.97 μs (2.3 μs+0.67 μs) would cause the ultrasonic receiver 202 to begin sampling acoustic waves reflected from a depth of approximately 1 mm below the outer surface of the finger 206.

FIG. 2B shows acoustic signals corresponding to photoacoustic emissions from tissues (e.g., blood and blood vessels) inside the finger 206, caused by the light that entered the finger 206. In the example shown in FIG. 2B, the acoustic signals originate from different depths (depths 208a, 208b and 208c) within the finger 206. Accordingly, the travel times t1, t2 and t3, from the depths 208a, 208b and 208c, respectively, to the ultrasonic receiver 202, are also different: in this instance, t3>t2>t1. Therefore, multiple acquisition time delays may be selected to receive acoustic waves emitted from the depths 208a, 208b and 208c.

FIG. 2C shows various types of signals and noise that may be produced by devices such as those shown in FIGS. 2A and 2B. In this example, the only desired signals produced by the receiver system 202 are those caused by PA4, which are arterial photoacoustic waves produced by the artery 207, by blood within the artery 207, or a combination thereof, responsive to impinging light 203a. However, undesired signals also may be produced by the receiver system 202 responsive to various other phenomena, including signals responsive to the electromagnetic interference (EMI) 211 produced by drive circuitry of the light source system 204, signals responsive to the reflected light 203*b*, which is reflected from an outer surface of the apparatus 200 or from the finger 206, signals responsive to photoacoustic waves PA1, PA2, PA3, PA5 and PA6, as well as to acoustic waves A1 and A2. In these examples, photoacoustic waves PA1 are produced by the receiver system 202 responsive to light reflected from the finger 206, photoacoustic waves PA2 are produced by the beamsplitter 201, photoacoustic waves PA3 are produced by the surface of the finger 206, photoacoustic waves PA5 are arterial photoacoustic signals that have a different trajectory from those of photoacoustic waves PA4, and photoacoustic waves PA6 are produced by the structure of the light source system 204. According to these examples, acoustic waves A1 are produced by reverberations of EMI, PA1, PA2, PA3, PA4, PA5 and PA6 within the platen 202. Here, acoustic waves A2 are produced by mechanical vibrations of the light source system 204, such as mechanical vibrations of, or produced by, drive circuitry of the light source system 204.

Various disclosed implementations have been designed by the present inventors in view of the foregoing issues. In some implementations, an apparatus may include a platen that is configured to separate one or more received arterial ultrasonic waves (such as the arterial photoacoustic waves PA4 of FIG. 2C) from one or more other types of received acoustic and photoacoustic waves (such as one or more of the photoacoustic waves PA1, PA2, PA3, PA5 and PA6 of FIG. 2C, the acoustic waves A1 and A2 of FIG. 2C, or combinations thereof). Some disclosed implementations may include a noise reduction system configured to at least partially decouple acoustic energy produced by the light source system 204 (such as the acoustic waves A2 of FIG. 2C), EMI produced by the light source system 204 (such as the EMI 211 of FIG. 2C), light produced by the light source system 204, or combinations thereof, from the ultrasonic receiver system 202. Some disclosed implementations may include a mirror system that is configured to reflect light away from the ultrasonic receiver system 202. In some disclosed implementations, the light source system may include at least one multi-junction laser diode, which may produce less noise than single-junction laser diodes.

Figure 3:
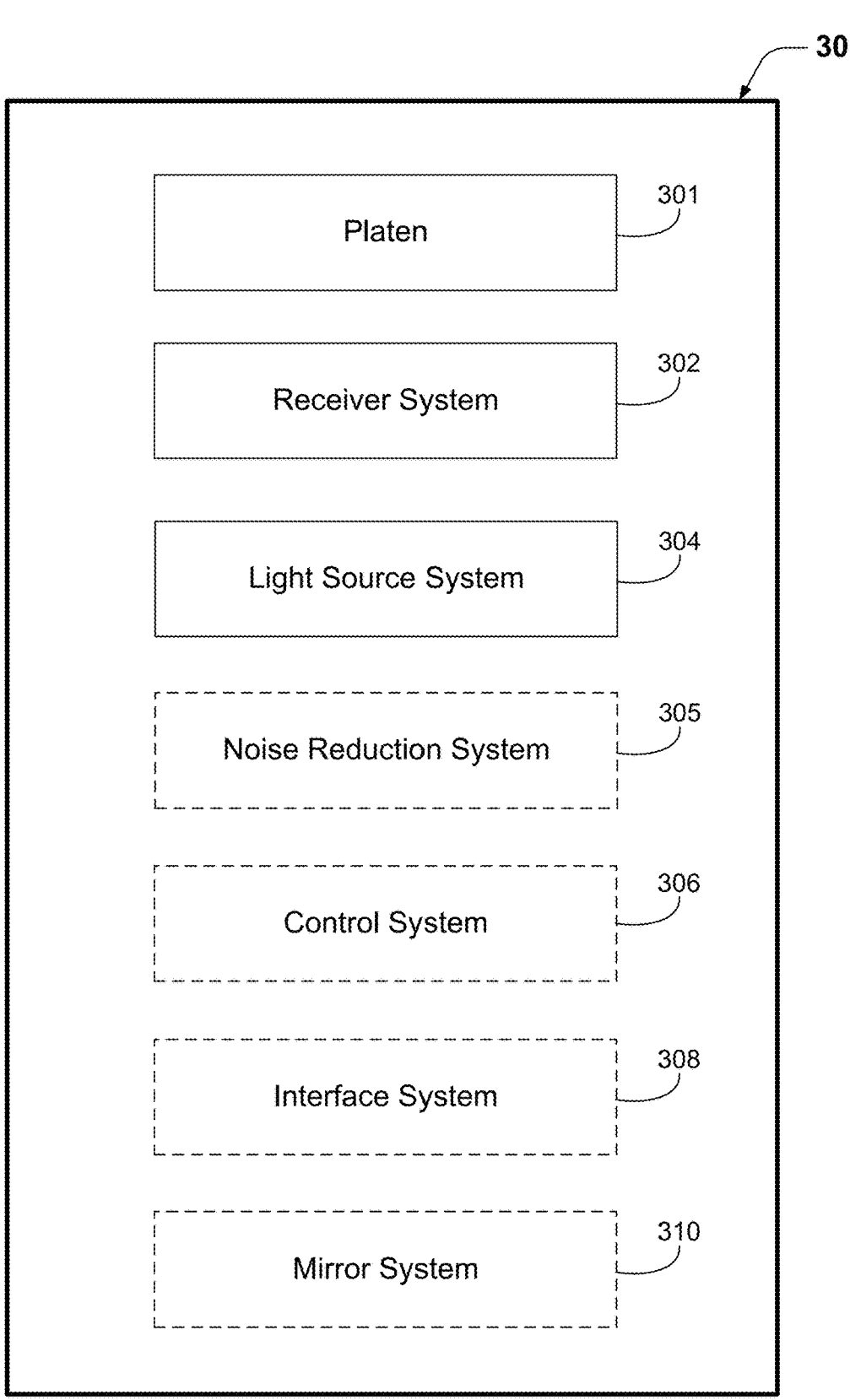
FIG. 3 is a block diagram that shows example components of an apparatus according to some disclosed implementations.

FIG. 3 is a block diagram that shows example components of an apparatus according to some disclosed implementations. In this example, the apparatus 300 includes a platen 301, a receiver system 302 and a light source system 304. Some implementations of the apparatus 300 may include a noise reduction system 305, a control system 306, an interface system 308, a mirror system 310, or combinations thereof.

Various examples of platens 301 are disclosed herein. Some examples are illustrated in FIGS. 4A-5, 7, 8 and 10A-11B, and are described in more detail below with reference to these drawings.

In some implementations in which the receiver system 302 includes an ultrasonic receiver system, the platen 301 may be configured to increase an intensity of ultrasonic energy received by at least a portion of the ultrasonic receiver system. In some such implementations, the platen 301 may include an acoustic waveguide. According to some implementations, the platen 301 may include an acoustic lens system. The acoustic lens system may, for example, reside on, or proximate, an outer surface of the platen 301. The acoustic lens system may, for example, include a spherical lens or a cylindrical lens.

According to some examples, the platen 301, the light source system 304, or a combination thereof, may be configured for transmitting light from the light source system to an outer surface of the platen (or to a target object on, or proximate, the outer surface) along a first axis, or substantially along the first axis. In this context, "substantially along the first axis" may mean within an angle range of plus or minus 10 degrees of the first axis, within an angle range of plus or minus 15 degrees of the first axis, within an angle range of plus or minus 20 degrees of the first axis, within an angle range of plus or minus 25 degrees of the first axis, within an angle range of plus or minus 30 degrees of the first axis, or within another such angle range.

In some examples, the platen 301 may be configured for transmitting the ultrasonic waves generated by the target object along a second axis, or substantially along the second axis. In this context, "substantially along the second axis" may mean within an angle range of plus or minus 10 degrees of the second axis, within an angle range of plus or minus 15 degrees of the second axis, within an angle range of plus or minus 20 degrees of the second axis, within an angle range of plus or minus 25 degrees of the second axis, within an angle range of plus or minus 30 degrees of the second axis, or within another such angle range. According to some examples, the second axis may be parallel to the first axis. However, in some examples, the second axis may be different from the first axis.

According to some examples, the platen 301 may include one or more anti-reflective layers, which are configured to suppress optical reflections. As used herein, the term "anti-reflective" refers to light reflection. In other words, an "anti-reflective" layer is one configured to reduce light reflection. In some such examples, the platen 301 may include one or more anti-reflective layers that reside between the platen 301 and the receiver 302. In some examples, a thickness of the platen 301, an acoustic velocity of the platen 301, or a combination thereof, may be configured to separate ultrasonic waves generated by blood in an artery from other ultrasonic waves.

In some examples, at least a portion of the outer surface of the platen 301 may have an acoustic impedance that is configured to approximate an acoustic impedance of human skin. The portion of the outer surface of the platen 301 may, for example, be a portion that is configured to receive a target object, such as a human digit. (As used herein, the terms "finger" and "digit" may be used interchangeably, such that a thumb is one example of a finger.) A typical range of acoustic impedances for human skin is 1.53-1.680 MRayls. In some examples, at least an outer surface of the platen 301 may have an acoustic impedance that is in the range of 1.4-1.8 MRayls, or in the range of 1.5-1.7 MRayls.

Alternatively, or additionally, in some examples at least an outer surface of the platen 301 may be configured to conform to a surface of human skin. In some such examples, at least an outer surface of the platen 301 may have material properties like those of putty or chewing gum.

Various examples of receiver systems 302 are disclosed herein, some of which may include ultrasonic receiver systems, optical receiver systems, or combinations thereof. In some implementations that include an ultrasonic receiver system, the ultrasonic receiver and an ultrasonic transmitter may be combined in an ultrasonic transceiver. In some examples, the receiver system 302 may include a piezoelectric receiver layer, such as a layer of PVDF polymer or a layer of PVDF-TrFE copolymer. In some examples, the receiver system 302 may include a composite piezoelectric material, such as a 0-3 composite, a 1-3 composite, a 2-2 composite, a 3-3 composite, etc. In some implementations, a single piezoelectric layer may serve as an ultrasonic receiver. In some implementations, other piezoelectric materials may be used in the piezoelectric layer, such as aluminum nitride (AlN) or lead zirconate titanate (PZT). The receiver system 302 may, in some examples, include an array of ultrasonic transducer elements, such as an array of piezoelectric micromachined ultrasonic transducers (PMUTs), an array of capacitive micromachined ultrasonic transducers (CMUTs), etc. In some such examples, a piezoelectric receiver layer, PMUT elements in a single-layer array of PMUTs, or CMUT elements in a single-layer array of CMUTs, may be used as ultrasonic transmitters as well as ultrasonic receivers. According to some examples, the receiver system 302 may be, or may include, an ultrasonic receiver array. In some examples, the apparatus 300 may include one or more separate ultrasonic transmitter elements. In some such examples, the ultrasonic transmitter(s) may include an ultrasonic plane-wave generator.

The light source system 304 may, in some examples, include one or more light-emitting diodes (LEDs). In some implementations, the light source system 304 may include one or more laser diodes. According to some implementations, the light source system 304 may include one or more vertical-cavity surface-emitting lasers (VCSELs). In some implementations, the light source system 304 may include one or more edge-emitting lasers. In some implementations, the light source system may include one or more neodymium-doped yttrium aluminum garnet (Nd:YAG) lasers.

The light source system 304 may, in some examples, be configured to transmit light in one or more wavelength ranges. In some examples, the light source system 304 may configured for transmitting light in a wavelength range of 500 to 600 nanometers (nm). In some examples, the light source system 304 may configured for transmitting light in a wavelength range of 700 to 800 nm. According to some examples, the light source system 304 may configured for transmitting light in a wavelength range of 800 to 950 nm.

The light source system 304 may include various types of drive circuitry, depending on the particular implementation. In some disclosed implementations, the light source system 304 may include at least one multi-junction laser diode, which may produce less noise than single-junction laser diodes. In some examples, the light source system 304 may include a drive circuit (also referred to herein as drive circuitry) configured to cause the light source system to emit pulses of light at pulse widths in a range from 3 nanoseconds to 1000 nanoseconds. According to some examples, the light source system 304 may include a drive circuit configured to cause the light source system to emit pulses of light at pulse repetition frequencies in a range from 1 kilohertz to 100 kilohertz.

In some implementations, the platen 301, the receiver system 302, the light source system 304, or combinations thereof may include one or more sound-absorbing layers. In some examples, the light source system 304 may include one or more electromagnetically shielded transmission wires. In some such examples, the one or more electromagnetically shielded transmission wires may be configured to reduce electromagnetic interference from the light source system 304 that is received by the receiver system 302. Such sound-absorbing layers, electromagnetically shielded transmission wires, or combinations thereof also may be considered to be part of the noise reduction system 305.

In some implementations, the light source system 304 may be configured for emitting various wavelengths of light, which may be selectable to trigger acoustic wave emissions primarily from a particular type of material. For example, because the hemoglobin in blood absorbs near-infrared light quite strongly, in some implementations the light source system 304 may be configured for emitting one or more wavelengths of light in the near-infrared range, in order to trigger acoustic wave emissions from hemoglobin. In view of factors such as skin reflectance, fluence, the absorption coefficients of blood and various tissues, and skin safety limits, particular wavelength ranges may be relatively more suitable or relatively less suitable for various use cases. For example, the wavelength ranges of 500 nm to 600 nm and of 800 to 950 nm may both be suitable for obtaining photoacoustic responses from relatively smaller, shallower blood vessels, such as blood vessels having diameters of approximately 0.5 mm and depths in the range of 0.5 mm to 1.5 mm, such as may be found in a finger. The wavelength range of 800 to 950 nm may, for example, be suitable for obtaining photoacoustic responses from relatively larger, deeper blood vessels, such as blood vessels having diameters of approximately 2.0 mm and depths in the range of 2 mm to 3 mm, such as may be found in an adult wrist. However, in some examples the control system 306 may control the wavelength(s) of light emitted by the light source system 304 to preferentially induce acoustic waves in blood vessels, other soft tissue, and/or bones. For example, an infrared (IR) light-emitting diode LED may be selected and a short pulse of IR light emitted to illuminate a portion of a target object and generate acoustic wave emissions that are then detected by the receiver system 302. In another example, an IR LED and a red LED or other color such as green, blue, white or ultraviolet (UV) may be selected and a short pulse of light emitted from each light source in turn with ultrasonic images obtained after light has been emitted from each light source. In other implementations, one or more light sources of different wavelengths may be fired in turn or simultaneously to generate acoustic emissions that may be detected by the ultrasonic receiver. Image data from the ultrasonic receiver that is obtained with light sources of different wavelengths and at different depths (e.g., varying RGDs) into the target object may be combined to determine the location and type of material in the target object. Image contrast may occur as materials in the body generally absorb light at different wavelengths differently. As materials in the body absorb light at a specific wavelength, they may heat differentially and generate acoustic wave emissions with sufficiently short pulses of light having sufficient intensities. Depth contrast may be obtained with light of different wavelengths and/or intensities at each selected wavelength. That is, successive images may be obtained at a fixed RGD (which may correspond with a fixed depth into the target object) with varying light intensities and wavelengths to detect materials and their locations within a target object. For example, hemoglobin, blood glucose or blood oxygen within a blood vessel inside a target object such as a finger may be detected photoacoustically.

According to some implementations, the light source system 304 may be configured for emitting a light pulse with a pulse width less than about 100 nanoseconds. In some implementations, the light pulse may have a pulse width between about 10 nanoseconds and about 500 nanoseconds or more. According to some examples, the light source system may be configured for emitting a plurality of light pulses at a pulse repetition frequency between 10 Hz and 100 kHz. Alternatively, or additionally, in some implementations the light source system 304 may be configured for emitting a plurality of light pulses at a pulse repetition frequency between about 1 MHz and about 100 MHZ.

Alternatively, or additionally, in some implementations the light source system 304 may be configured for emitting a plurality of light pulses at a pulse repetition frequency between about 10 Hz and about 1 MHZ. In some examples, the pulse repetition frequency of the light pulses may correspond to an acoustic resonant frequency of the ultrasonic receiver and the substrate. For example, a set of four or more light pulses may be emitted from the light source system 304 at a frequency that corresponds with the resonant frequency of a resonant acoustic cavity in the sensor stack, allowing a build-up of the received ultrasonic waves and a higher resultant signal strength. In some implementations, filtered light or light sources with specific wavelengths for detecting selected materials may be included with the light source system 304. In some implementations, the light source system may contain light sources such as red, green and blue LEDs of a display that may be augmented with light sources of other wavelengths (such as IR and/or UV) and with light sources of higher optical power. For example, high-power laser diodes or electronic flash units (e.g., an LED or xenon flash unit) with or without filters may be used for short-term illumination of the target object.

In some examples, the apparatus 300 includes a noise reduction system 305. The specific component or components of the noise reduction system 305 may vary according to the particular implementation. Some examples of the noise reduction system 305 are described in more detail below with reference to FIGS. 12-14.

According to some examples, the noise reduction system 305 may include one or more noise reduction elements configured to at least partially decouple acoustic energy produced by the light source system 304, electrical energy produced by the light source system 304, light produced by the light source system 304, or combinations thereof, from the receiver system 302.

In some examples, the noise reduction system 305 may include one or more electromagnetically shielded transmission wires, which may in some examples be electromagnetically shielded transmission wires of the light source system 304. In some such examples, the one or more electromagnetically shielded transmission wires may be configured to reduce electromagnetic interference from the light source system 304 that is received by the receiver system 302.

According to some examples, the noise reduction system 305 may include one or more air gaps between the light source system 304 and the receiver system 302. Alternatively, or additionally, in some examples the noise reduction system 305 may include one or more sound-absorbing layers configured to reduce the acoustic energy produced by the light source system 304 that is received by the receiver system 302. In some examples, at least one of the one or more sound-absorbing layers may reside in, or proximate, the receiver system 302. In some examples, at least one of the one or more sound-absorbing layers may reside in, or proximate, the light source system 304.

In some examples, the noise reduction system 305 may include one or more light-absorbing layers configured to reduce the amount of light produced by the light source system 304 that is received by the receiver system 302. Preferably, the one or more light-absorbing layers have a relatively low Grüneisen parameter and do not produce a large photoacoustic signal. According to some examples, at least one light-absorbing layer may reside in, or proximate, the receiver system 302.

According to some examples, the noise reduction system 305 may include one or more reflective layers configured to reduce the amount of light produced by the light source system 304 that is received by the receiver system 302. Such reflective layers also may be considered to be part of the mirror system 310. In some examples, at least one reflective layer may reside between the platen 301 and at least a portion of the receiver system 302.

The control system 306 may include one or more general purpose single- or multi-chip processors, digital signal processors (DSPs), application specific integrated circuits (ASICs), field programmable gate arrays (FPGAs) or other programmable logic devices, discrete gates or transistor logic, discrete hardware components, or combinations thereof. The control system 306 also may include (and/or be configured for communication with) one or more memory devices, such as one or more random access memory (RAM) devices, read-only memory (ROM) devices, etc. Accordingly, the apparatus 300 may have a memory system that includes one or more memory devices, though the memory system is not shown in FIG. 3. The control system 306 may be configured for receiving and processing data from the receiver system 302, e.g., as described below. If the apparatus 300 includes an ultrasonic transmitter, the control system 306 may be configured for controlling the ultrasonic transmitter. In some implementations, functionality of the control system 306 may be partitioned between one or more controllers or processors, such as a dedicated sensor controller and an applications processor of a mobile device.

In some examples, the control system 306 may be configured to control the light source system 304 to emit light towards a target object on an outer surface of the platen 301. In some such examples, the control system 306 may be configured to receive signals from the ultrasonic receiver system 302 corresponding to the ultrasonic waves generated by the target object responsive to the light from the light source system 304. In some examples, the control system 306 may be configured to identify one or more arterial signals from the ultrasonic receiver system. In some such examples, the one or more arterial signals may be, or may include, one or more arterial wall signals corresponding to ultrasonic waves generated by one or more arterial walls of the target object. In some such examples, the one or more arterial signals may be, or may include, one or more arterial blood signals corresponding to ultrasonic waves generated by blood within an artery of the target object. In some examples, the control system 306 may be configured to estimate one or more cardiac features based, at least in part, on the one or more arterial signals. According to some examples, the cardiac features may be, or may include, blood pressure.

Some implementations of the apparatus 300 may include the interface system 308. In some examples, the interface system 308 may include a wireless interface system. In some implementations, the interface system 308 may include a user interface system, one or more network interfaces, one or more interfaces between the control system 306 and a memory system and/or one or more interfaces between the control system 306 and one or more external device interfaces (e.g., ports or applications processors), or combinations thereof. According to some examples in which the interface system 308 is present and includes a user interface system, the user interface system may include a microphone system, a loudspeaker system, a haptic feedback system, a voice command system, one or more displays, or combinations thereof. According to some examples, the interface system 308 may include a touch sensor system, a gesture sensor system, or a combination thereof. The touch sensor system (if present) may be, or may include, a resistive touch sensor system, a surface capacitive touch sensor system, a projected capacitive touch sensor system, a surface acoustic wave touch sensor system, an infrared touch sensor system, any other suitable type of touch sensor system, or combinations thereof.

In some examples, the interface system 308 may include, a force sensor system. The force sensor system (if present) may be, or may include, a piezo-resistive sensor, a capacitive sensor, a thin film sensor (for example, a polymer-based thin film sensor), another type of suitable force sensor, or combinations thereof. If the force sensor system includes a piezo-resistive sensor, the piezo-resistive sensor may include silicon, metal, polysilicon, glass, or combinations thereof. An ultrasonic fingerprint sensor and a force sensor system may, in some implementations, be mechanically coupled. In some such examples, the force sensor system may be integrated into circuitry of the ultrasonic fingerprint sensor. In some examples, the interface system 308 may include an optical sensor system, one or more cameras, or a combination thereof.

According to some examples, the apparatus 300 may include a mirror system 310 that includes one or more mirrors. For example, the mirror system 310 may include one or more mirrors that are configured to reflect light from the light source system 304 away from the receiver system 302.

The apparatus 300 may be used in a variety of different contexts, many examples of which are disclosed herein. For example, in some implementations a mobile device may include the apparatus 300. In some such examples, the mobile device may be a smart phone. According to some examples, the mobile device may be a pen-type device. Some relevant examples are described below with reference to FIGS. 7 and 8. In some implementations, a wearable device may include the apparatus 300. The wearable device may, for example, be a bracelet, an armband, a wristband, a watch, a ring, a headband or a patch.

Figure 4A:
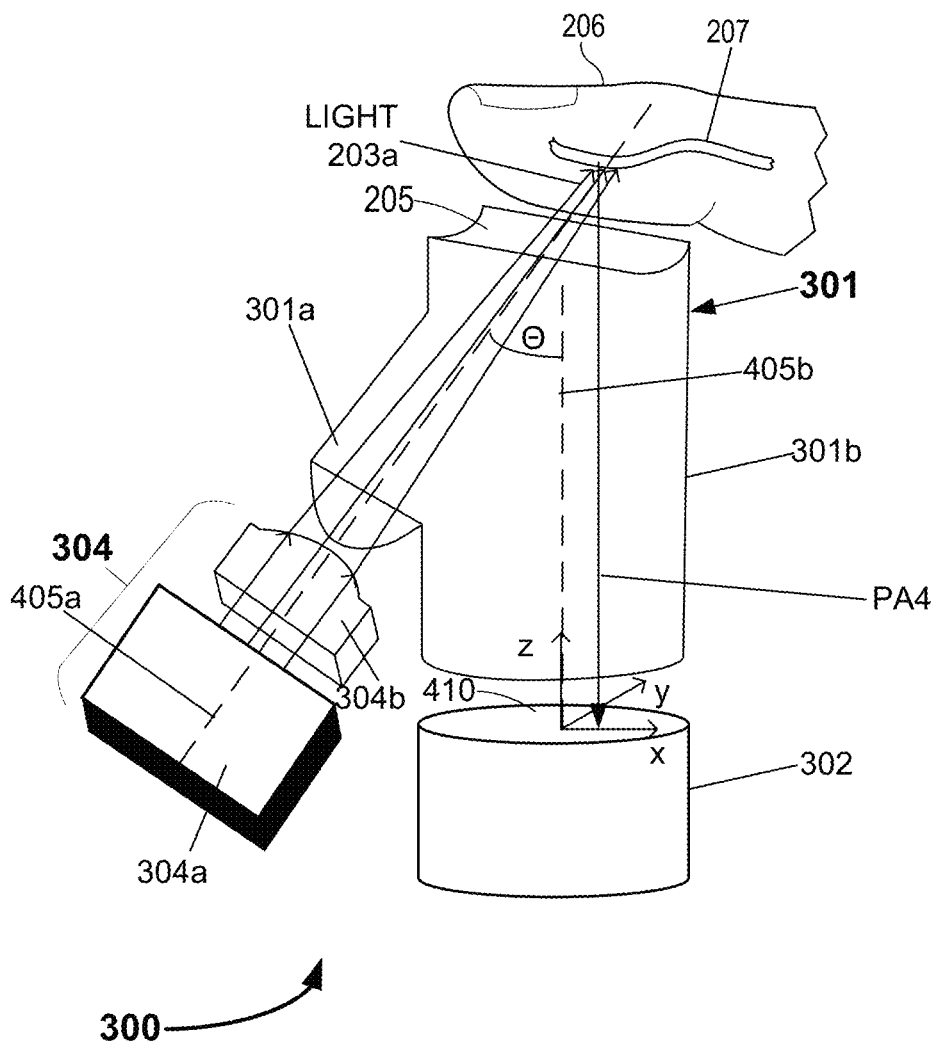
FIG. 4A shows example components of an apparatus according to some disclosed implementations.

FIG. 4A shows example components of an apparatus according to some disclosed implementations. As with other figures provided herein, the numbers, types and arrangements of elements shown in FIG. 4A are merely presented by way of example. In this example, the apparatus 300 is an instance of the apparatus 300 shown in FIG. 3. According to this example, the apparatus 300 includes a platen 301, a receiver system 302 and a light source system 304.

In this example, an outer surface 205 of the platen 301 is configured to receive a target object, such as the finger 206. Although the finger 206 is shown to be positioned above the outer surface 205 in FIG. 4A, this is merely to show the outer surface 205 more clearly. In this example, the outer surface 205 of the platen 301 is configured as an acoustic lens: the cylindrical shape of the outer surface 205 is configured to focus photoacoustic waves, including ultrasonic waves, produced within the finger 206 by the light 203*a* from the light source system 304. Accordingly, the outer surface 205 of the platen 301 is configured as a cylindrical acoustic lens, which can increase the intensity of ultrasonic energy received by at least a portion of the receiver system 302. This effect is described in more detail below with reference to FIGS. 10A-10D.

In some alternative examples, the platen 301 may include another type of acoustic lens. For example, at least a portion of the outer surface 205 of the platen 301 may be configured as a spherical acoustic lens. In some such examples, a recess in at least a portion of the outer surface 205 may have a shape that corresponds to a portion of a sphere.

According to this example, the light source system 304 includes a light-emitting portion 304*a* and a lens 304*b*. The light-emitting portion 304*a* may, for example, include one or more light-emitting diodes, one or more laser diodes, one or more VCSELs, one or more edge-emitting lasers, one or more neodymium-doped yttrium aluminum garnet (Nd: YAG) lasers, or combinations thereof. In this example, the lens 304*b* is configured to focus the light 203*a* emitted by the light-emitting portion 304*a* into a relatively smaller cross-sectional area, which increases the intensity of the light 203*a* received by a target object (such as the finger 206) on the outer surface 205.

In this example, the platen 301 includes platen portion 301*a* and platen portion 301*b*. According to this example, the platen portion 301*a* is configured to direct the light 203*a* from the light source system 304 towards the outer surface 205. In this example, the platen portion 301*b* is configured to direct acoustic waves, including photoacoustic waves, emitted by a target object on the outer surface 205 towards the receiver system 302.

According to this example, the platen 301 (more specifically, the platen portion 301*a*) and the light source system 304 are configured for transmitting light 203*a* from the light source system 304 to the outer surface 205 of the platen 301 along a first axis, or substantially along the first axis. In FIG. 4A, the axis 405*a* is an example of the first axis. In this context, "substantially along the first axis" may mean within an angle range of plus or minus 10 degrees of the first axis, within an angle range of plus or minus 15 degrees of the first axis, within an angle range of plus or minus 20 degrees of the first axis, within an angle range of plus or minus 25 degrees of the first axis, within an angle range of plus or minus 30 degrees of the first axis, or within another such angle range.

In this example, the platen 301 (more specifically, the platen portion 301*b*) is configured for transmitting acoustic waves, including but not limited to ultrasonic waves, generated by a target object on the outer surface 205 towards the receiver system 302 along a second axis, or substantially along the second axis. In FIG. 4A, the axis 405*b* is an example of the second axis. In this context, "substantially along the second axis" may mean within an angle range of plus or minus 10 degrees of the second axis, within an angle range of plus or minus 15 degrees of the second axis, within an angle range of plus or minus 20 degrees of the second axis, within an angle range of plus or minus 25 degrees of the second axis, within an angle range of plus or minus 30 degrees of the second axis, or within another such angle range. According to this example, the platen portion 301*b* is shown to be transmitting arterial photoacoustic waves PA4 substantially along the axis 405*b*.

In this example, the second axis is not parallel to the first axis, but instead is separated from the first axis by an angle Θ. Such examples have the potential advantage of allowing the platen portion(s) configured for light transmission be designed and optimized independently from the platen portion(s) configured for ultrasonic wave transmission. According to some alternative examples, the second axis may be parallel to the first axis. However, in some alternative examples, the first axis may be parallel to, or substantially parallel to (such as within +/−5 degrees, within +/−10 degrees, within +/−15 degrees, within +/−20 degrees, etc.) the second axis. The first axis and the second axis may, for example, be defined by a coordinate system that is relative to the apparatus 300 or a portion thereof. In the example shown in FIG. 4A, a Cartesian coordinate system is shown to be defined relative to a surface 410 of the receiver system 302. In some implementations, a mirror, a light-absorbing layer, or a combination thereof, may reside on, or proximate, the surface 410.

In some implementations, the platen 301 (for example, the platen portion 301b) may include an acoustic waveguide. In some such implementations, the platen portion 301b may be configured for transmitting ultrasonic waves generated by a target object on the outer surface 205 towards the receiver system 302, via the acoustic waveguide.

According to some examples, the platen 301 may include one or more anti-reflective layers. As used herein, the term "anti-reflective" refers to light reflection. In other words, an "anti-reflective" layer is one configured to reduce light reflection. In some examples, one or more anti-reflective layers may reside on the platen 301, or proximate the platen 301, for example on or proximate the outer surface 205.

Figure 4B:
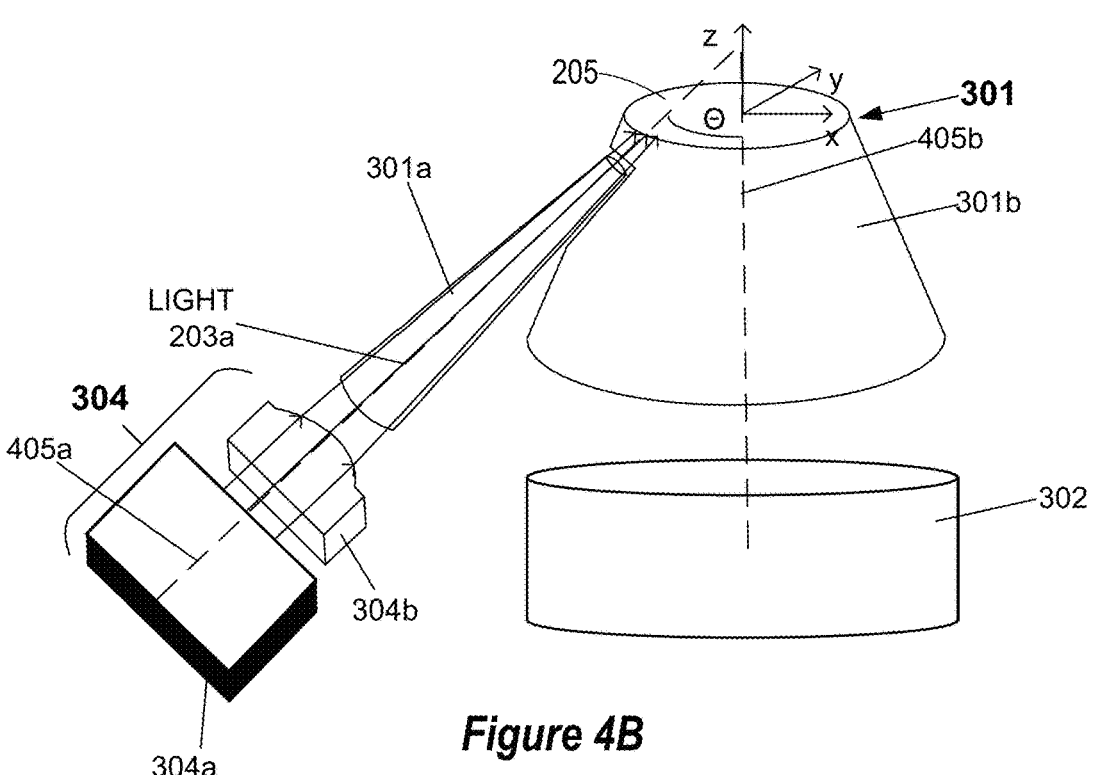
FIGS. 4B and 4C shows example components of an apparatus according to some additional disclosed implementations.
Figure 4C:
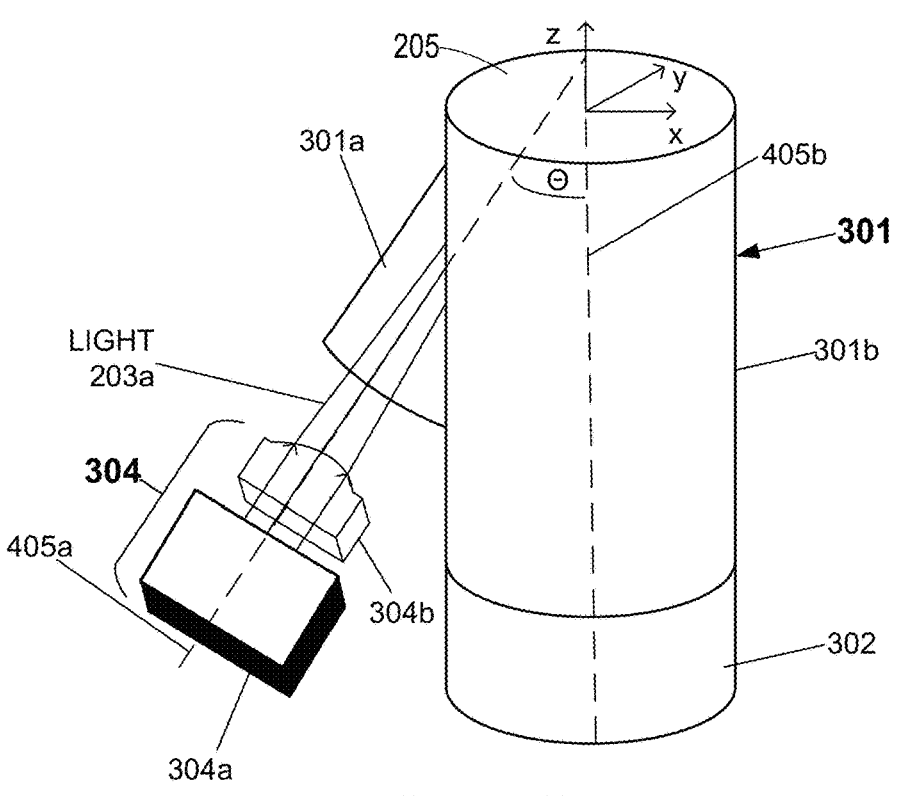

FIGS. 4B and 4C shows example components of an apparatus according to some additional disclosed implementations. As with other figures provided herein, the numbers, types and arrangements of elements shown in FIGS. 4B and 4C are merely presented by way of example. In these examples, the apparatuses 300 are instances of the apparatus 300 shown in FIG. 3. According to these examples, the apparatuses 300 include a platen 301, a receiver system 302 and a light source system 304. In these examples, as in FIG. 4A, the light source system 304 includes a light-emitting portion 304a and a lens 304b. Here, the lenses 304b are configured to focus the light 203a emitted by the light-emitting portions 304a into a relatively smaller cross-sectional area, which increases the intensity of the light 203a received by a target object (such as the finger 206) on the outer surface 205.

In these examples, the platen 301 includes platen portion 301a and platen portion 301b. According to these examples, the platen portion 301a is configured to direct the light 203a from the light source system 304 towards the outer surface 205. In these examples, the platen portion 301b is configured to direct acoustic waves, including photoacoustic waves, emitted by a target object on the outer surface 205 towards the receiver system 302. In the example shown in FIG. 4B, both the platen portion 301a and the platen portion 301b have conical shapes. In the example shown in FIG. 4C, both the platen portion 301b has a cylindrical shape.

According to these examples, the platen portions 301a and the light source system 304 are configured for transmitting light 203a from the light source system 304 to the outer surface 205 of the platen 301 along the axis 405a, or substantially along the axis 405a. In these examples, the platen portions 301b are configured for transmitting acoustic waves, including but not limited to ultrasonic waves, generated by a target object on the outer surface 205 towards the receiver system 302 along the axis 405b, or substantially along the axis 405b. In these examples, the axis 405a is separated from the axis 405b by an angle Θ. In the examples shown in FIGS. 4B and 4C, a Cartesian coordinate system is shown to be defined relative to the outer surface 205 of the platen 301.

In the implementations shown in FIGS. 4B and 4C, the platen portion 301b includes an acoustic waveguide. At least a part of each of the platen portions 301b is configured for transmitting ultrasonic waves generated by a target object on the outer surface 205 towards the receiver system 302, via the acoustic waveguide. The present inventors have determined that acoustic waveguides formed in platens having radial symmetry, such as those shown in FIGS. 4B and 4C, can increase the intensity of acoustic waves, including but not limited to ultrasonic energy, received by the receiver system 302.

According to some examples, the platen 301 may include one or more anti-reflective layers. In some examples, one or more anti-reflective layers may reside on, or proximate, the outer surface 205.

As noted elsewhere herein, in some examples the apparatus 300 may include a platen 301 that is configured to separate one or more received arterial ultrasonic waves (such as the arterial photoacoustic waves PA4 of FIG. 2C) from one or more other types of received acoustic and photoacoustic waves (such as one or more of the photoacoustic waves PA1, PA2, PA3, PA5 and PA6 of FIG. 2C, the acoustic waves A1 and A2 of FIG. 2C, or combinations thereof).

Figure 4D:
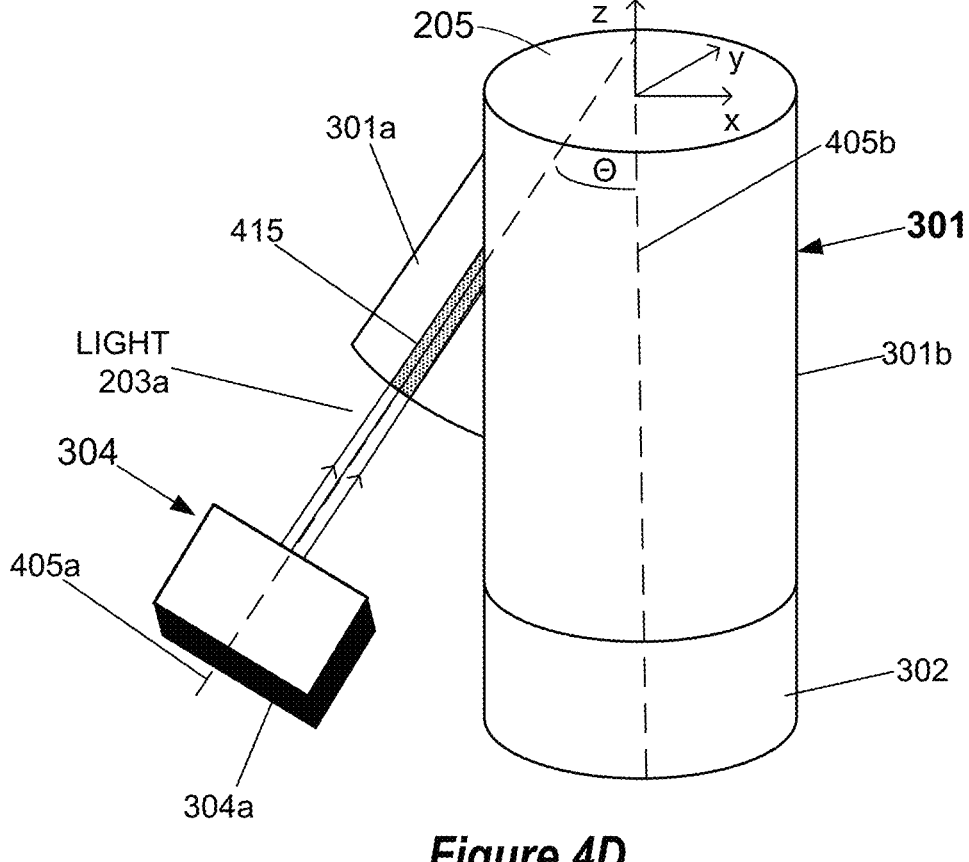
FIG. 4D shows example components of an apparatus according to an additional disclosed implementation.

FIG. 4D shows example components of an apparatus according to an additional disclosed implementation. As with other figures provided herein, the numbers, types and arrangements of elements shown in FIG. 4D are merely presented by way of example. In this example, the apparatus 300 is an instance of the apparatus 300 shown in FIG. 3. According to this example, the apparatus 300 includes a platen 301, a receiver system 302 and a light source system 304. In this example, the light source system 304 includes a light-emitting portion 304a but does not include a lens 304b. Some alternative implementations may include a lens 304b or another component that is configured to couple light from the light-emitting portion 304a into the platen portion 301a.

In this example, the platen portion 301a includes an optical waveguide 415. In some instances, a hole may be formed in the platen portion 301a and an optical waveguide, such as one or more optical fibers, may be inserted into the hole. According to some other examples, the platen portion 301a may be fabricated so as to include the optical waveguide 415. Although other disclosed examples of the apparatus 100 may not be shown as including an optical waveguide, including the examples shown in FIGS. 4A-4C, 5, 7, 8 and 11A-15B, some alternative examples of the apparatus 100 may nonetheless include one or more waveguides.

According to some examples, the platen 301 may include one or more anti-reflective layers. In some examples, one or more anti-reflective layers may reside on, or proximate, the outer surface 205.

Figure 5:
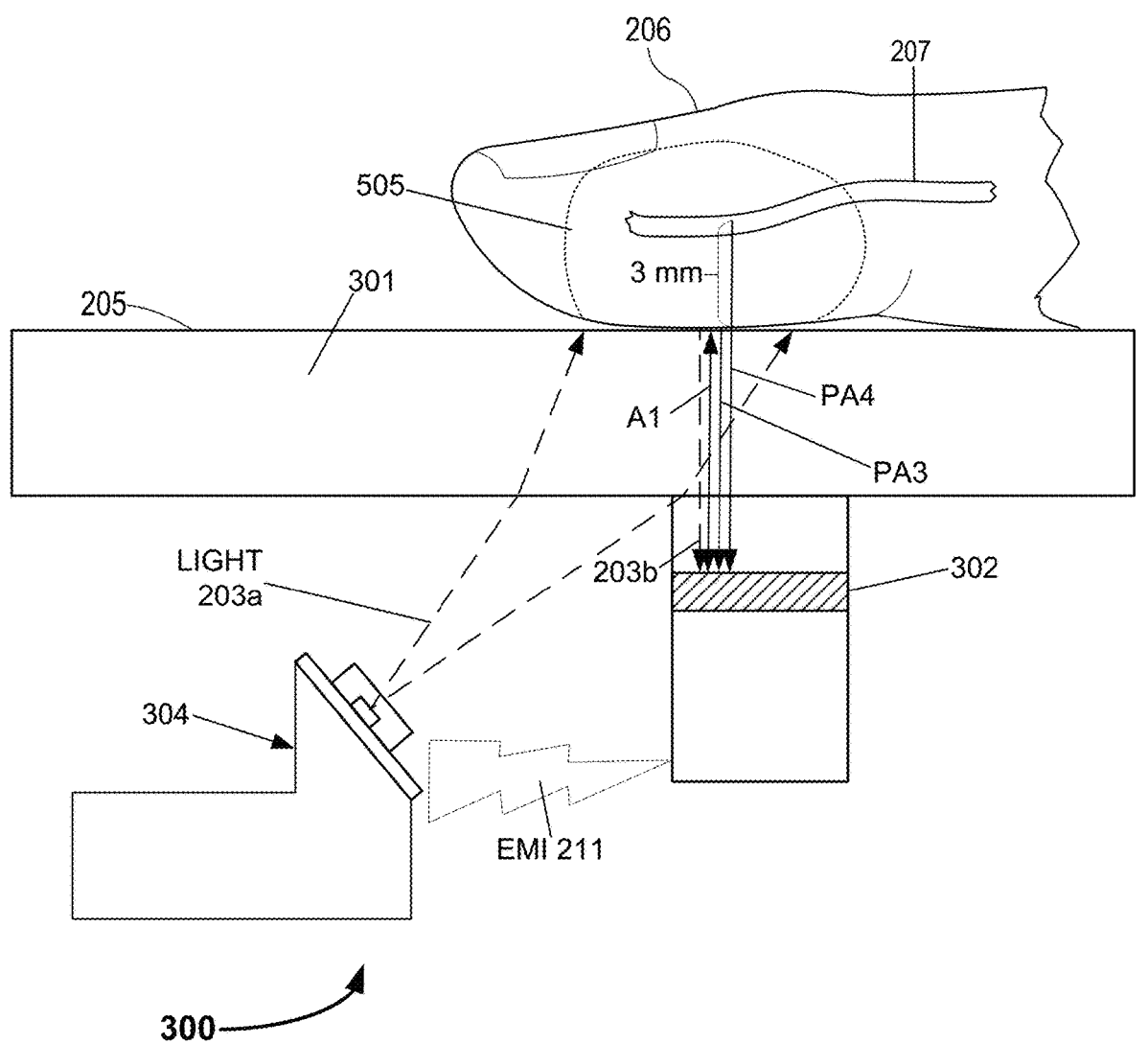
FIG. 5 shows example components of an apparatus according to some disclosed implementations.

FIG. 5 shows example components of an apparatus according to some disclosed implementations. As with other figures provided herein, the numbers, types and arrangements of elements shown in FIG. 5 are merely presented by way of example. In this example, the apparatus 300 is an instance of the apparatus 300 shown in FIG. 3. According to this example, the apparatus 300 includes a platen 301, a receiver system 302 and a light source system 304.

FIG. 5 shows an example of a platen 301 that is configured to separate one or more arterial ultrasonic waves from one or more other types of waves received by the receiver system 302. In this example, an outer surface 205 of the platen 301 is configured to receive a target object, such as the finger 206. According to this example, the light 203a from the light source system 304 is illuminating an outer surface of the finger 206 on, and proximate, the outer surface 205, as well as an area 505 within the finger 206.

In this example, light 203b is reflected from the outer surface of the finger 206 towards the receiver system 302. According to this example, the light 203a causes the finger 206 to produce photoacoustic waves PA3 from a surface of the finger 206 and causes the artery 207 to produce arterial photoacoustic waves PA4 from approximately 3 millimeters within the finger 206. Acoustic waves A1 are caused by reverberations of the photoacoustic waves PA3 between the receiver system 302 and the finger 206. In some examples, the EMI 211 may cause the receiver system 302 to produce acoustic waves that reverberate between the receiver system 302 and the finger 206, or between the receiver system 302 and the outer surface 205 of the platen 301. As may be determined by comparing FIG. 5 with FIG. 2C, FIG. 5 shows only a few examples of the noise sources and artifacts that may be present in an actual system.

Figure 6A:
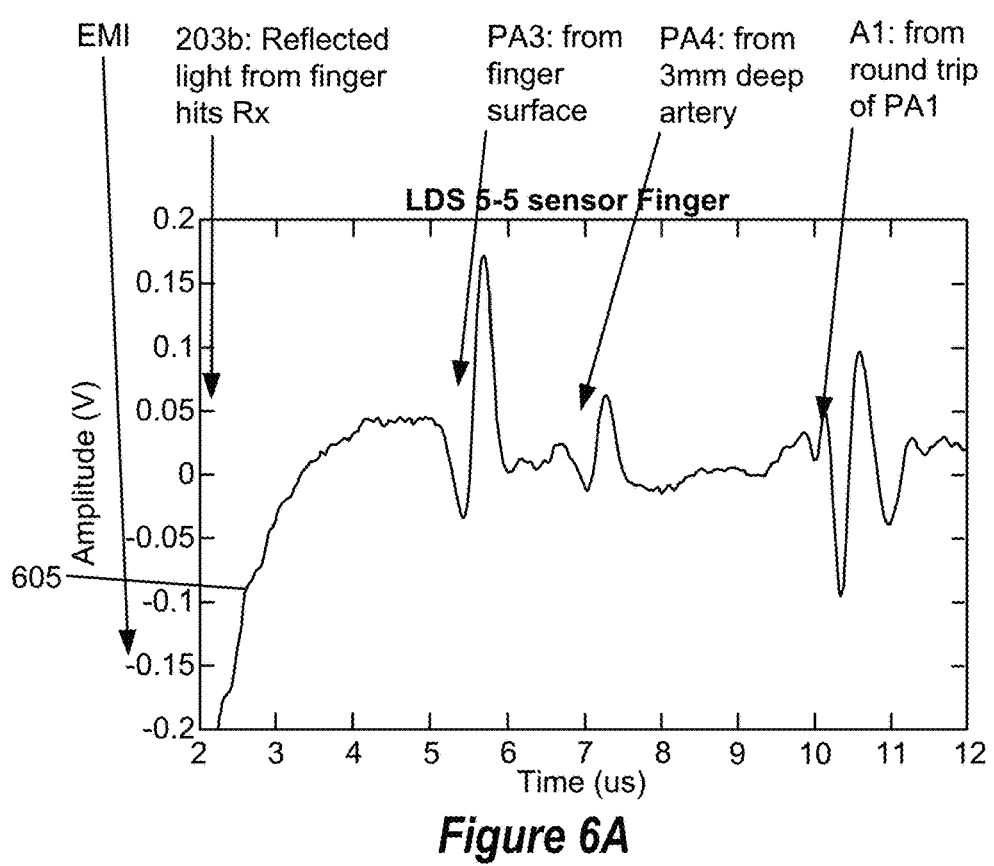
FIG. 6A is a graph that shows the response of a receiver system to the EMI, light and acoustic waves represented in FIG. 5.

FIG. 6A is a graph that shows the response of a receiver system to the EMI, light and acoustic waves represented in FIG. 5 according to one example. In this example, the horizontal axis represents time in microseconds and the vertical axis represent amplitude in volts. In this example, the EMI is received before the time represented by the amplitude curve 605. According to this example, the amplitude curve 605 shows amplitude spikes corresponding to the arrival of PA3, PA4 and A1 at the receiver system 302. It may be observed that the signal of interest, which corresponds to PA4, has a lower amplitude than that of PA3 and A1. However, in some examples PA4 may be selectively sampled by using the proper range gate delay (RGD) and range gate window (RGW), for example by using an RGD of approximately 7 microseconds and an RGW of approximately 0.5 microseconds.

Alternatively, or additionally, the thickness of a platen 301, such the platen 301 shown in FIG. 5, may be configured to separate one or more arterial acoustic waves, such as PA4, from one or more other types of waves received by the receiver system 302, such as PA3 and A1. The present inventors have determined that by making the thickness of the platen 301 at least a minimum thickness, acoustic waves from a target of interest, such as arterial acoustic waves, may be separated from other types of waves received by the receiver system 302. The minimum thickness depends on the speed of sound within the platen, the depth of the target(s) of interest, etc.

Figure 6B:
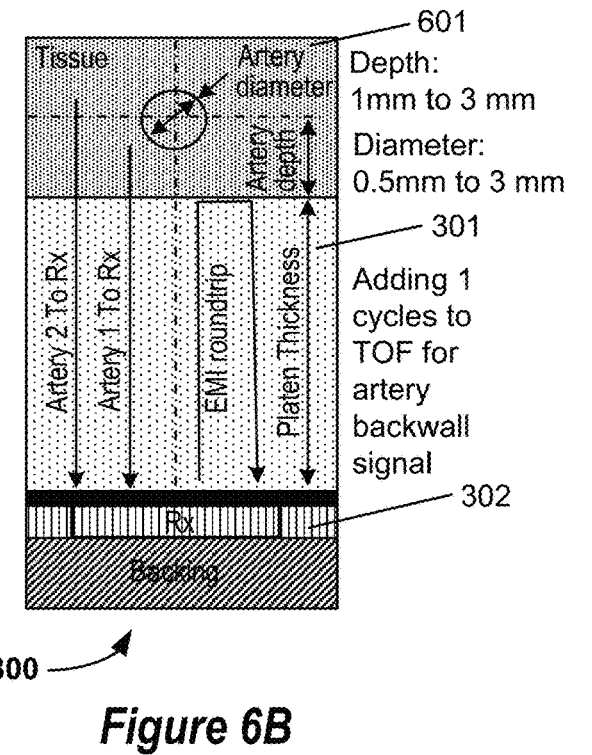
FIG. 6B shows example components of an apparatus according to some disclosed implementations.

FIG. 6B shows example components of an apparatus according to some disclosed implementations. As with other figures provided herein, the numbers, types and arrangements of elements shown in FIG. 6B are merely presented by way of example. In this example, the apparatus 300 is an instance of the apparatus 300 shown in FIG. 3. According to this example, the apparatus 300 includes a platen 301, a receiver system 302 and a light source system 304 (not shown). According to this example, the platen 301 is an acrylic platen. In this example, the receiver 302 is receiving photoacoustic waves from Artery 1 and Artery 2 within a target object 601, as well as acoustic waves caused by EMI signals that are reverberating within the platen 301: these acoustic waves are labeled "EMI round trip" in FIG. 6B. The target object 601 may, for example, be a portion of a finger or a wrist. As suggested by the artery depth ranges and artery diameters shown in FIG. 6B, the present inventors have simulated times of flight for acoustic waves from arteries at depths ranging from 1 to 3 millimeters, each artery having a range of diameters.

FIG. 6C is a graph that shows examples of times of flight for acoustic waves corresponding to each of the artery sizes and depths shown in FIG. 6B, for a range of platen thicknesses. The platen thicknesses, depths, diameters, etc., referenced in FIGS. 6B and 6C are merely made by way of example and in no way limit the scope of the present disclosure or any related applications. FIG. 6C also shows examples of times of flight for the "EMI round trip" acoustic waves represented in FIG. 6B, for the same range of platen thicknesses. In these examples, the platen thicknesses range from 1 mm to approximately 13 mm. In FIG. 6C, the crosses correspond to times of flight for Artery 1 and the circles correspond to times of flight for Artery 2. The smallest circle corresponds to an artery diameter of 1 mm for Artery 2, the largest circle corresponds to an artery diameter of 3 mm for Artery 2, and the intervening circles correspond to artery diameters of 1.5, 2.0 and 2.5 mm for Artery 2. Similarly, the smallest cross corresponds to the smallest diameter for Artery 1, which is 1.0 mm, and the largest cross corresponds to the largest diameter for Artery 1, which is 3.0 mm. In these examples, artery depth is measured from the center of the artery to the skin surface. It will be understood that the depth of an actual artery is always greater than the artery's diameter. The diamond shapes correspond to the "EMI round trip" acoustic waves represented in FIG. 6B.

The vertical line 605, which corresponds to an acrylic platen thickness of approximately 11 mm, corresponds to a platen thickness for which the "EMI round trip" acoustic waves arrive after photoacoustic waves from arteries that are 3 mm deep and 3 mm in diameter. Accordingly, FIG. 6C indicates that if the platen 301 is made of acrylic, the platen 301 should be made at least 11 mm thick, and preferably thicker than 11 mm (such as 12 mm or more), in order to differentiate the photoacoustic waves produced by an artery that is 3 mm deep from acoustic waves corresponding to reverberations caused by EMI.

Figure 7:
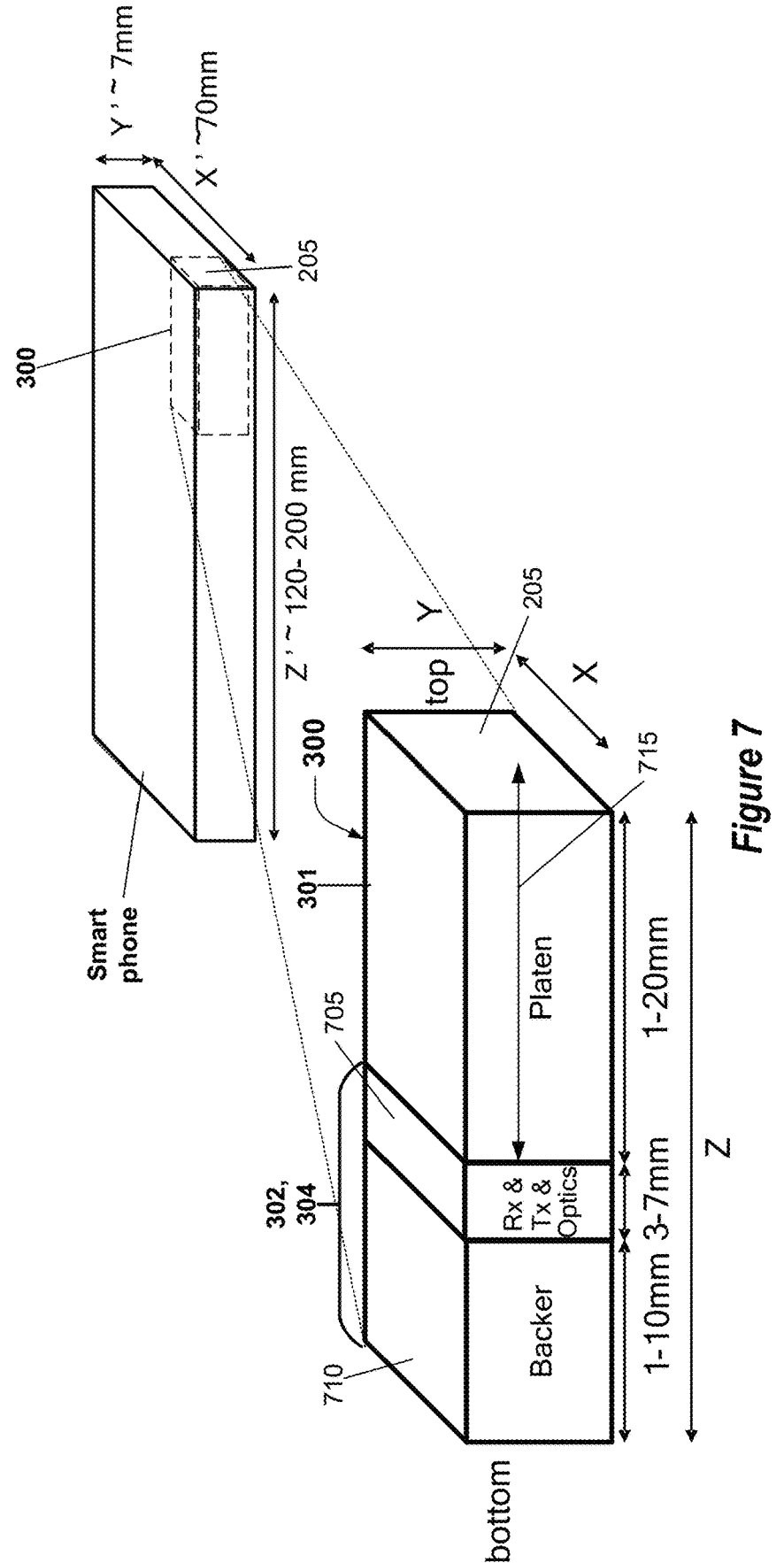
FIG. 7 shows an example of a photoacoustic apparatus that is configured to be a component of a smart phone.

FIG. 7 shows an example of a photoacoustic apparatus that is configured to be a component of a smart phone. As with other figures provided herein, the numbers, types and arrangements of elements shown in FIG. 7 are merely presented by way of example. In this example, the apparatus 300 is an instance of the apparatus 300 shown in FIG. 3.

In this example, the receiver system 302 and the light source system 304 are located in the apparatus segment 705, which resides between the platen 301 and a backer layer 710. According to this example, the apparatus 300 is configured to receive a target object on the outer surface 205. As suggested by the arrow 715, light emitted by the light source system 304 and photoacoustic waves from the target object may travel substantially along the Z axis of the apparatus 300. In this example, the Z axis of the apparatus 300 is configured to be aligned with the long axis Z' of the smart phone.

According to this example, the platen 301 may range in thickness from 1 mm to 20 mm, the apparatus segment 705 may range in thickness from 3 mm to 7 mm, and the backer 710 may range in thickness from 1 mm to 10 mm. In this example, the length of the smart phone along the Z' axis may range from 120-200 mm. However, these dimensional ranges are merely examples. As noted above with reference to FIGS. 5-6C, it can be advantageous for the platen 301 to be at least thick enough to separate signals of interest, such as signals caused by arterial photoacoustic waves, from other artifacts. This minimum platen thickness will depend on the speed of sound in the platen 301 and the depth to the target(s) of interest.

Figure 8:
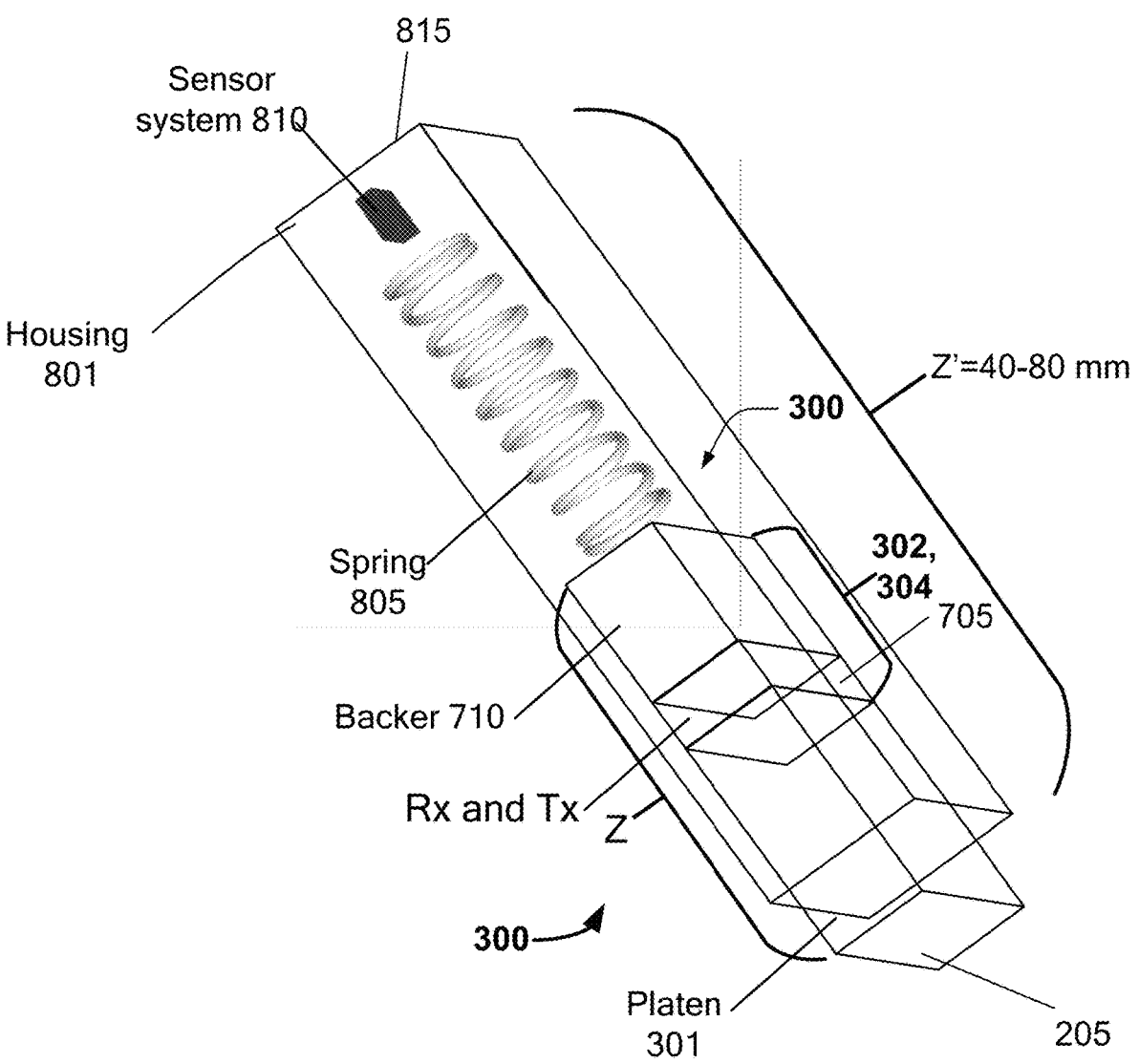
FIG. 8 shows an example of a photoacoustic apparatus that is configured for pen-type implementations.

FIG. 8 shows an example of a photoacoustic apparatus that is configured for pen-type implementations. As with other figures provided herein, the numbers, types and arrangements of elements shown in FIG. 8 are merely presented by way of example. In this example, the apparatus 300 is an instance of the apparatus 300 shown in FIG. 3.

In this example, the overall configuration of the receiver system 302, the light source system 304 and the platen 301 is similar to that shown in FIG. 7: the light source system 304 are located in the apparatus segment 705, which resides between the platen 301 and a backer layer 710. According to this example, the apparatus 300 is configured to receive a target object on the outer surface 205.

In this example, the spring 805 is configured to allow the backer layer 710, the apparatus segment 705 and the platen 301 to move as a unit inside the housing 801 while pressure is applied on the outer surface 205 against a target object, such as a wrist or a finger. According to this example, the sensor system 810 is configured to be in contact with the spring 805 and to provide sensor output signals corresponding to force, pressure, displacement, etc., caused by displacement of the backer layer 710, the apparatus segment 705 and the platen 301 within the housing 801. The sensor system 810 may include a motion sensor, a force sensor or a combination thereof. In some examples, the apparatus may include a display system having one or more displays. The display system may, for example, indicate information from the sensor system 810, information from the receiver system, information corresponding to data received from the receiver system (such as blood pressure or other cardiac data), etc. In some examples, the display system may include one or more displays residing in or on the housing 801, such as on the side 815 which is opposite the outer surface 205.

In some examples, the dimensions of the apparatus segment 705, the platen 301 and the backer layer 710 may be similar to, or the same as, those shown in FIG. 7: the platen 301 may range in thickness from 1 mm to 20 mm, the apparatus segment 705 may range in thickness from 3 mm to 7 mm, and the backer 710 may range in thickness from 1 mm to 10 mm. In this example, the length of the housing 801 along the Z' axis may range from 40-80 mm. However, these dimensional ranges are merely examples. As noted above with reference to FIGS. 5-6C, it can be advantageous for the platen 301 to be thick enough to separate signals of interest, such as arterial photoacoustic waves, from other artifacts.

FIGS. 9A, 9B and 9C show examples of ray tracing inside a target object and two different types of platen. In each example, the apparatus 300 includes a platen 301, a receiver system 302 and a light source system 304 (not shown). As with other figures provided herein, the numbers, dimensions, types and arrangements of elements shown in FIG. 9A-9C are merely presented by way of examples. In these examples, the apparatuses 300 are instances of the apparatus 300 shown in FIG. 3. According to these examples, rays corresponding to photoacoustic waves PA are emanating from a point source 905 within a target object 601, which may be a finger, a wrist, etc., responsive to light 203*a*. For ease of illustration and to avoid clutter, only examples of photoacoustic waves PA emitted downward, in the general direction of the receiver system 302, are shown in FIGS. 9A-9C.

In the example shown in FIG. 9A, the platen 301 does not include an acoustic waveguide. However, in the examples shown in FIGS. 9B and 9C, the platen 301 includes an acoustic waveguide 901. FIGS. 9A and 9B show the apparatuses 300 in the same orientation, with cross-sectional views in the x-z plane, whereas FIG. 9C shows a cross-sectional view in the y-z plane In all of these examples, the receiver system 302 receives only a small fraction of the photoacoustic waves PA emanating from the point source 905. This is true in part because of the relatively small area of the receiver system 302, as compared to the area of $2\pi$ steradians over which the photoacoustic waves PA are spread. Moreover, given typical speeds of sound in the target object 601 and the platen 301 (for example, approximately 1500 m/s for a finger and 2800 m/s for acrylic), the photoacoustic waves PA tend to be refracted away from the receiver system 302 at the target object/platen interface.

However, the receiver system 302 shown in FIGS. 9B and 9C, which includes the waveguide 901, receives a relatively greater portion of the photoacoustic waves PA emanating from the point source 905, as compared to the receiver system 302 shown in FIG. 9A.

FIGS. 10A, 10B, 10C and 10D show examples of two additional types of platen and corresponding ray tracing diagrams. In each example, the apparatus 300 includes a platen 301, a receiver system 302 (not shown in FIGS. 10A and 10C) and a light source system 304 (not shown in FIGS. 10A-10D). As with other figures provided herein, the numbers, dimensions, types and arrangements of elements shown in FIGS. 10A-10D are merely presented by way of examples. In these examples, the apparatuses 300 are instances of the apparatus 300 shown in FIG. 3.

FIGS. 10A and 10C show different examples of the apparatus 300 in the same orientation, with the x-z plane towards the viewer, whereas FIGS. 10B and 10D show cross-sectional views in the y-z plane. In these examples, the apparatus 300 shown in FIG. 10A is the same apparatus 300 that is shown in FIG. 10B. FIGS. 10C and 10D show a different implementation of the apparatus 300, as compared to that shown in FIGS. 10A and 10B.

FIGS. 10A-10D all show platens 301 that have the overall shape of rectangular prisms. However, FIGS. 10A and 10B include platens 301 in which the entire outer surface 205 is substantially planar, whereas FIGS. 10C and 10D include platens 301 having a cylindrical groove 1005 within an otherwise substantially planar outer surface 205. In the example shown in FIGS. 10C and 10D, the cylindrical groove functions as a cylindrical acoustic lens. In the example shown in FIG. 10D, the target object 601 is a finger that is pressed into the cylindrical groove 1005.

In some examples, dimension A, which represents depth, may be 3 mm, 4 mm, 5 mm, 6 mm, etc., whereas dimension B may be 5 mm, 10 mm, 15 mm, 20 mm, 25 mm, 30 mm, etc. In some alternative examples, an outer surface 205 of a platen 301 may include a spherical recess, which may function as a spherical acoustic lens. The present inventors have determined that such acoustic lenses can increase the intensity of photoacoustic waves received by the receiver system 302 by more than two-fold, as compared to the intensity of photoacoustic waves received by the receiver system 302 in the absence of such acoustic lenses.

Figures 11A, 11B:
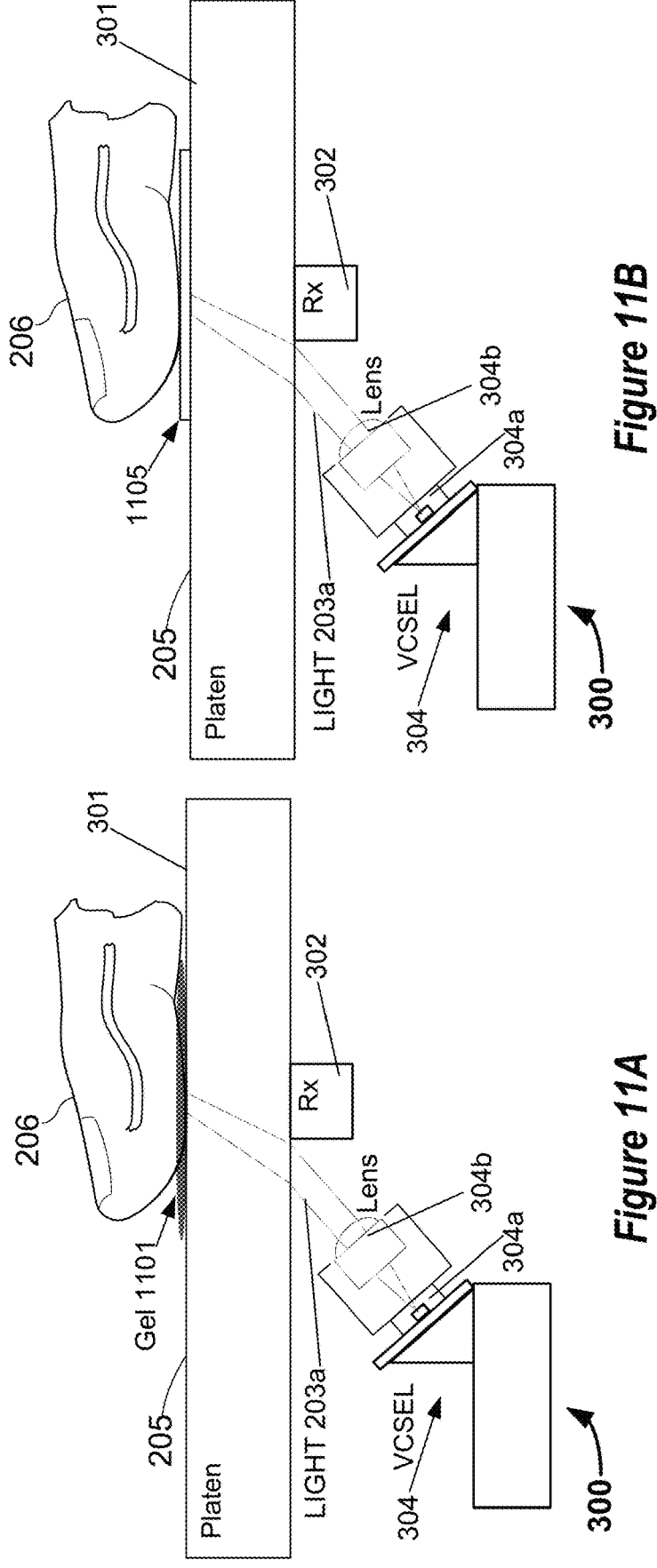
FIGS. 11A and 11B shows example components of an apparatus according to some additional disclosed implementations.

FIGS. 11A and 11B shows example components of an apparatus according to some additional disclosed implementations. As with other figures provided herein, the numbers, types and arrangements of elements shown in FIGS. 11A and 11B are merely presented by way of example. In these examples, the apparatuses 300 are instances of the apparatus 300 shown in FIG. 3. According to these examples, the apparatuses 300 include a platen 301, a receiver system 302 and a light source system 304. In these examples, the light source system 304 includes a light-emitting portion 304*a* and a lens 304*b*. Here, the lenses 304*b* are configured to focus the light 203*a* emitted by the light-emitting portions 304*a* into a relatively smaller cross-sectional area, which increases the intensity of the light 203*a* received by a target object (such as the finger 206) on the outer surface 205 of the platen 301.

In these examples, at least a portion of the outer surface of the platen 301, or a material residing on the platen 301, has an acoustic impedance that is configured to approximate an acoustic impedance of human skin. In the example shown in FIG. 11A, the gel 1101 on the surface of the platen 301 has an acoustic impedance that is configured to approximate an acoustic impedance of human skin. Although such a gel may be effective in coupling the acoustic waves produced in a finger or a wrist to the platen 301, some users may not wish to have such a gel in contact with their skin. Moreover, the present inventors have found that some coupling gels can cause background noise.

In the example shown in FIG. 11B, a solid outer layer 1105 of the platen 301 has an acoustic impedance that is configured to approximate an acoustic impedance of human skin. Such implementations can provide advantages, as compared to implementations that involve coupling gels. Such advantages may include broader end user acceptance and the avoidance of background noise that may be caused by some coupling gels.

A typical range of acoustic impedances for human skin is 1.53-1.680 MRayls. Accordingly, in some examples the gel 1101 or the outer layer 1105 may have an acoustic impedance that is in the range of 1.4-1.8 MRayls, or in the range of 1.5-1.7 MRayls.

According to some examples, the gel 1101 or the outer layer 1105 may have an acoustic impedance that is between the acoustic impedance of human skin and acoustic impedance of an inner portion of the platen 301. For example, if the inner portion of the platen 301 were made of acrylic, having an acoustic impedance that is in the range of 3.08-3.26 MRayls, the gel 1101 or the outer layer 1105 may have an acoustic impedance that is in the range of 1.7-3.08 MRayls. In another example, if the inner portion of the platen 301 were made of polycarbonate, having an acoustic impedance that is in the range of 2.69-2.7 MRayls, the gel 1101 or the outer layer 1105 may have an acoustic impedance that is in the range of 1.7-2.69 MRayls.

In some examples, the outer layer 1105 may include a polymer of the siloxane family, such as polydimethylsiloxane (PDMS), which is also known as dimethicone. According to some examples, the outer layer 1105 may include Aqualene™, a material provided by Innovation Polymers, Aqualink™ 100, Aqualink™ 200, or a similar material.

Alternatively, or additionally, in some examples the outer layer 1105 may be configured to conform to a surface of human skin. In some such examples, the outer layer 1105 may have material properties like those of putty or chewing gum. In some such examples, the outer layer 1105 may be configured for plastic deformation when subjected to a stress caused by a typical finger press, such as a finger press in the range of 50 to 500 gram-force.

As noted elsewhere herein, some disclosed examples of the apparatus 300 include a noise reduction system 305. In some examples, the noise reduction system 305 may include one or more noise reduction elements configured to at least partially decouple acoustic energy produced by the light source system 304, electrical energy produced by the light source system 304, light produced by the light source system 304, or combinations thereof, from the receiver system 302.

Figure 12:
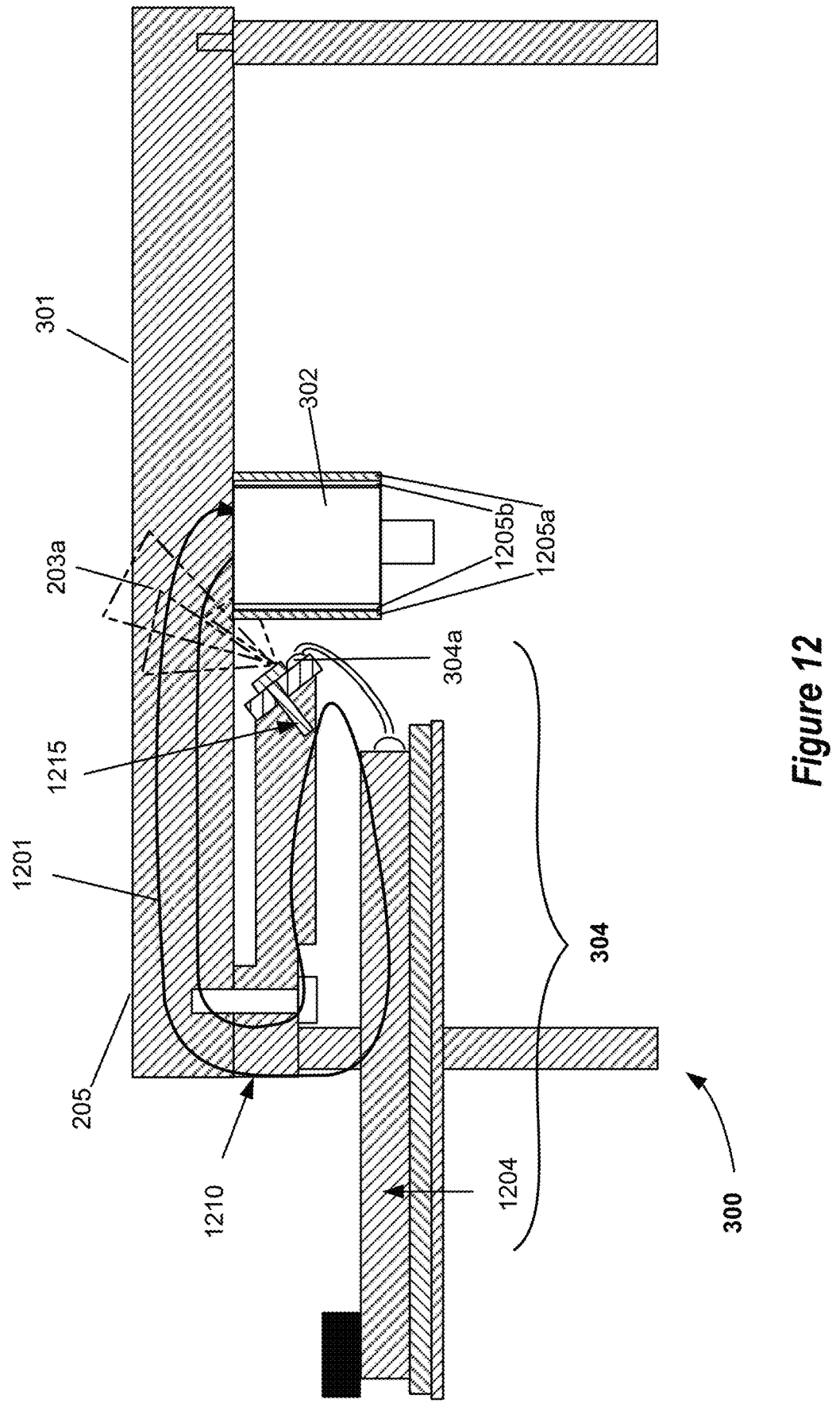
FIGS. 12, 13 and 14 show elements of devices that include noise reduction elements.
Figure 13:
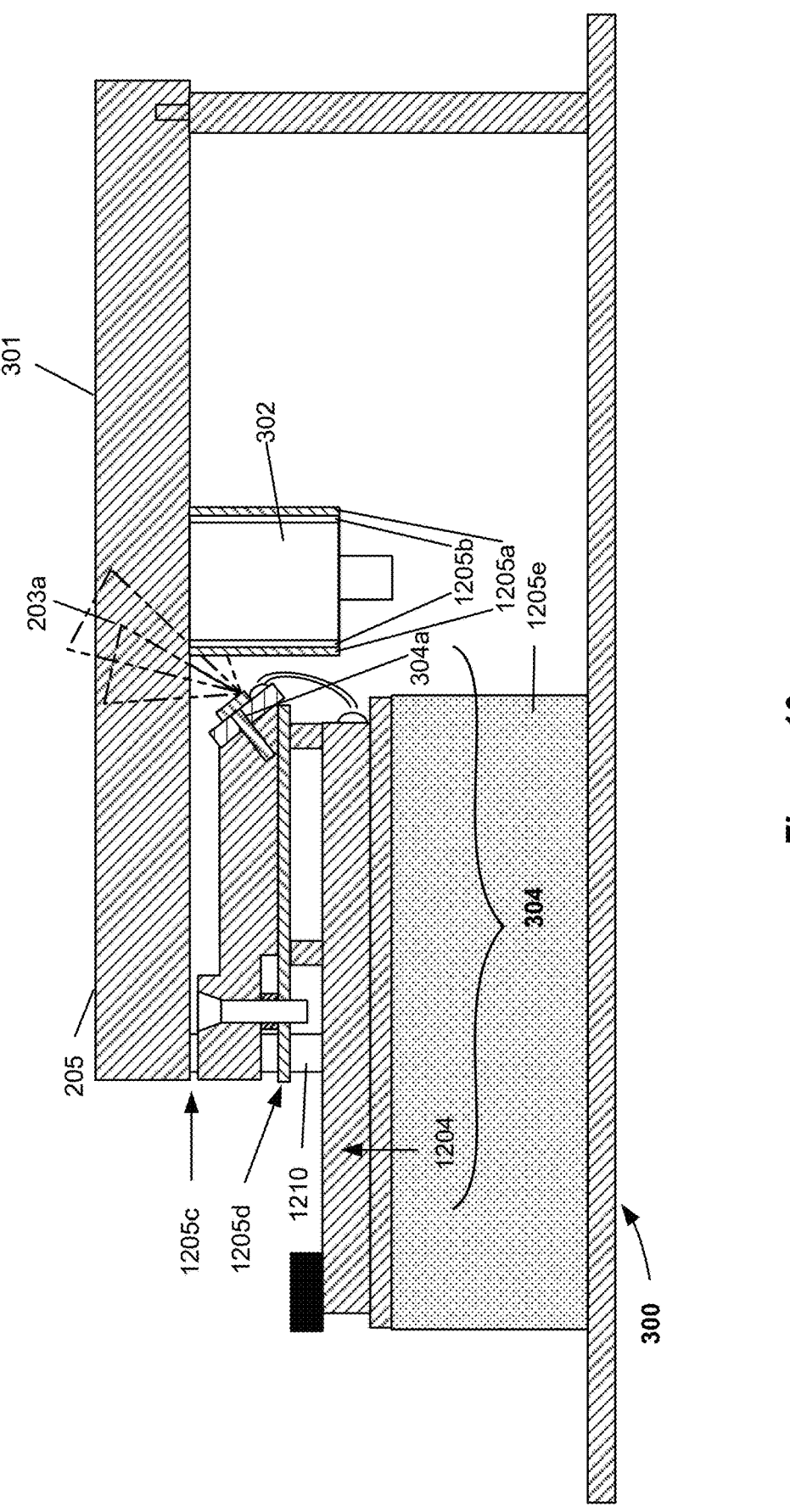
Figure 14:
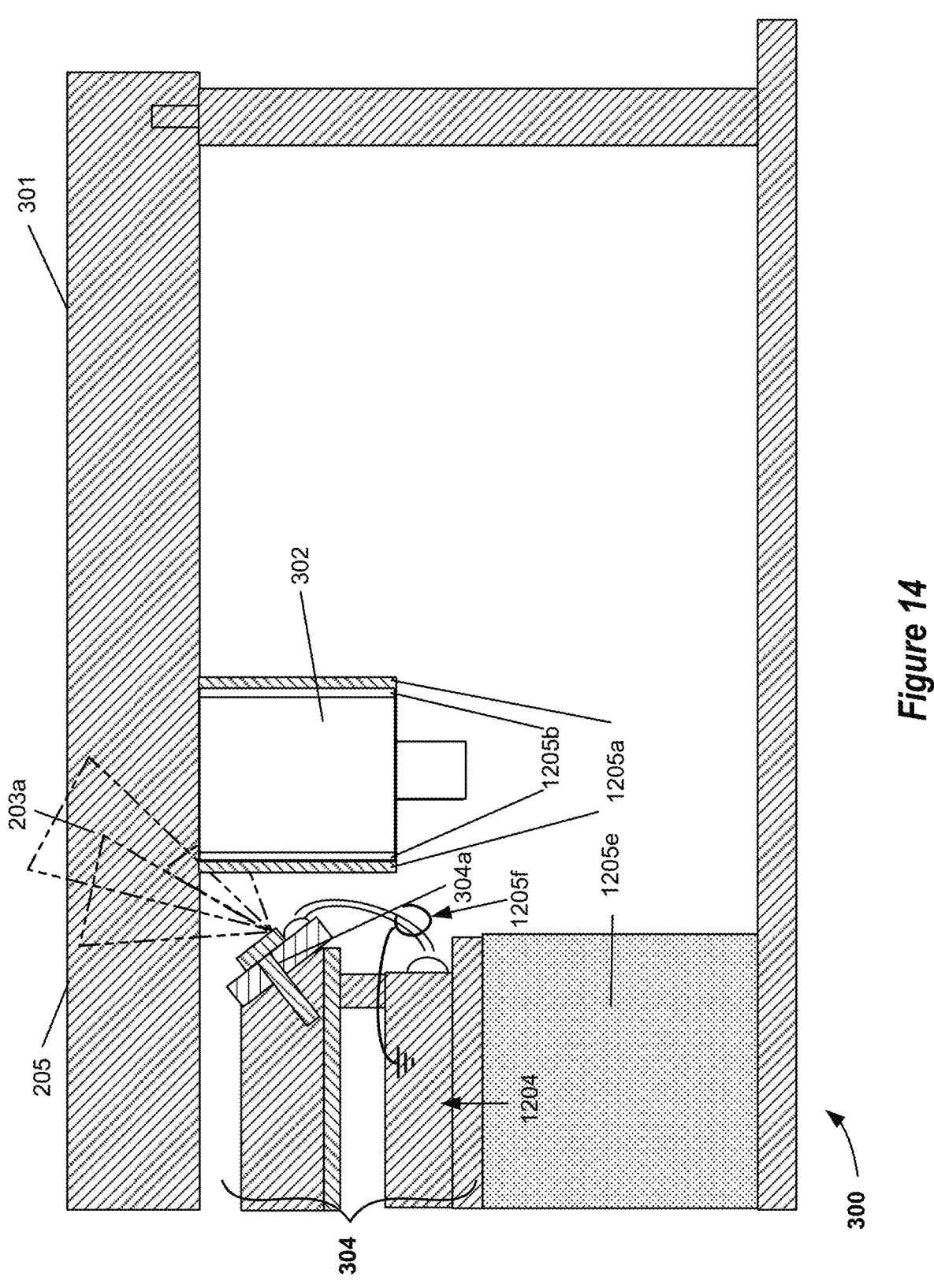

FIGS. 12, 13 and 14 show elements of devices that include noise reduction elements. In each example, the apparatus 300 also includes a platen 301, a receiver system 302 and a light source system 304. In these examples, the light source system 304 includes at least a light-emitting element 304a and drive circuitry 1204. As with other figures provided herein, the numbers, dimensions, types and arrangements of elements shown in FIGS. 12, 13 and 14 are merely presented by way of examples. In these examples, the apparatuses 300 are instances of the apparatus 300 shown in FIG. 3.

In FIG. 12, the apparatus includes noise reduction elements 1205a and 1205b. In this example, noise reduction element 1205a is a light shield that at least partially shields the receiver system 302 from the light 203a emitted by the light-emitting element 304a. According to this example, noise reduction element 1205b is configured for attenuating at least some of the acoustic waves that would otherwise be transmitted to the receiver system 302.

However, despite the presence of the noise reduction elements 1205a and 1205b, a significant amount of acoustic noise 1201 is still transferred from the drive circuitry 1204 to the receiver system 302. As suggested by the paths traversed by the arrows in FIG. 12 that represent the acoustic noise 1201, some of the acoustic noise 1201 is transmitted from the drive circuitry 1204 to the receiver system 302 via the support structure 1210, which connects the drive circuitry 1204 to the platen 301, whereas some of the acoustic noise 1201 is transmitted from the drive circuitry 1204 to the receiver system 302 via the support structure 1215, which connects the light-emitting element 304a to the platen 301.

In some examples, a significant amount of acoustic noise 1201 (for example, corresponding to an amplitude of approximately 1 volt) may still be transferred from the drive circuitry 1204 to the receiver system 302, despite the presence of the noise reduction elements 1205a and 1205b.

In the example shown in FIG. 13, the apparatus 300 includes noise reduction elements 1205c, 1205d and 1205e, as well as noise reduction elements 1205a and 1205b. In this example, noise reduction element 1205c is an air gap between the support structure 1210 and the platen 301. According to this example, noise reduction element 1205d is a plate that mounts the a structure supporting the light-emitting element 304a to the support structure 1210 below the noise reduction element 1205c. In this example, noise reduction element 1205e includes a foam that is configured for dampening at least some of the acoustic waves generated by the drive circuitry 1204 that would otherwise have been transmitted to the receiver system 302.

The present inventors have observed that the acoustic noise transferred from the drive circuitry 1204 to the receiver system 302 was significantly reduced by the presence of the noise reduction elements 1205c, 1205d and 1205e, as compared to the example shown in FIG. 12. In some examples, the amplitude of the acoustic noise may be reduced from approximately 1 volt to approximately 0.2 volts.

In the example shown in FIG. 14, the apparatus 300 includes a noise reduction element 1205f, as well as the noise reduction elements 1205a-1205e of FIG. 13. In this example, noise reduction element 1205f includes one or more electromagnetically shielded transmission wires that are configured to reduce electromagnetic interference from the light source system 304 that would otherwise be received by the receiver system 302. In this example, the one or more electromagnetically shielded transmission wires are included in a cable and include connections for both the positive and negative connections of the light-emitting element 304a. According to this example, each electromagnetically shielded transmission wire is grounded.

The present inventors have observed that the acoustic noise transferred from the drive circuitry 1204 to the receiver system 302 was further reduced by the presence of the noise reduction element 1205f, as compared to the example shown in FIG. 13. In some examples, the amplitude of the acoustic noise may be reduced from approximately 0.2 volts to approximately 0.1 volts.

Figures 15A, 15B:
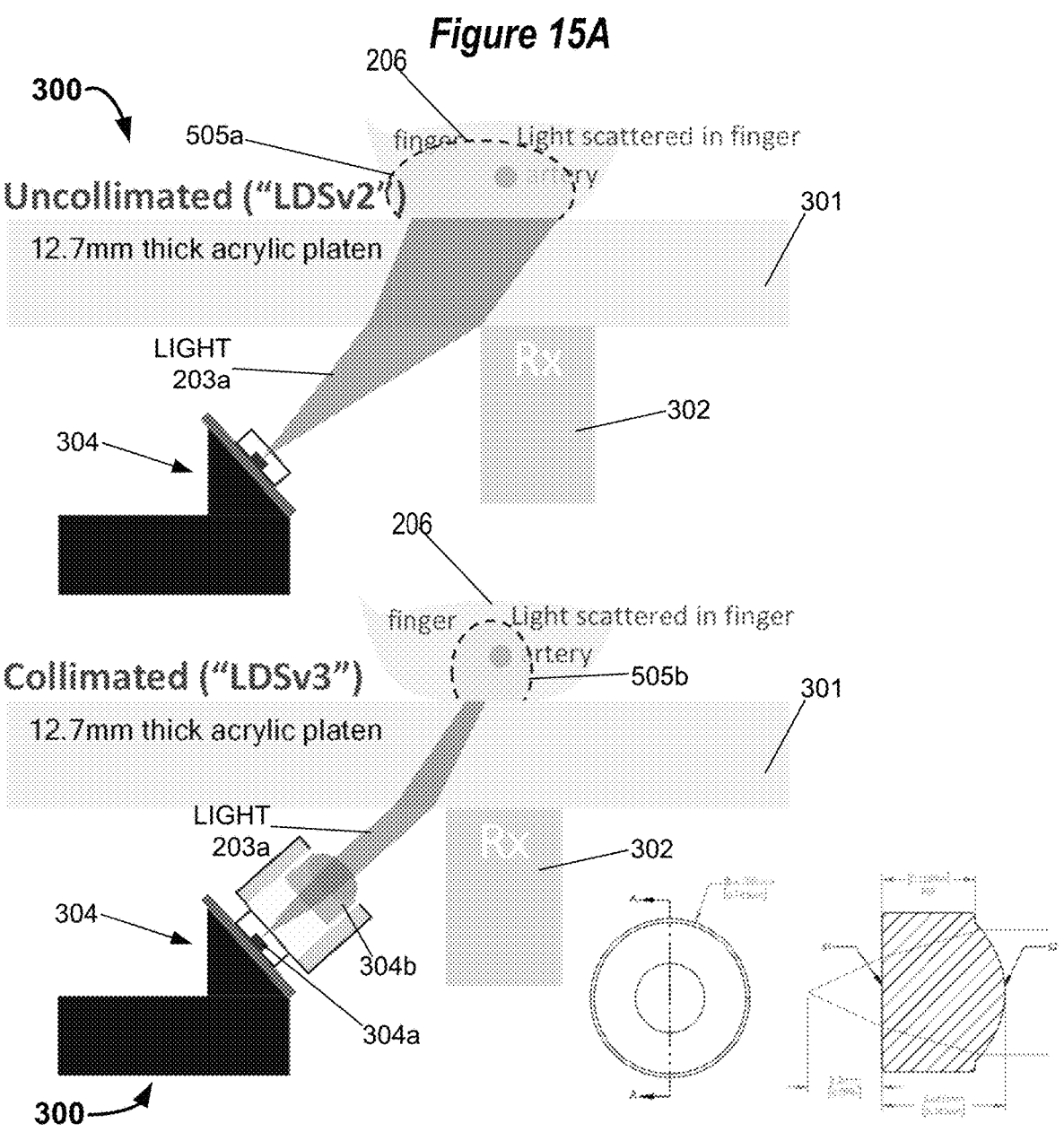
FIGS. 15A and 15B show examples of devices with different types of light source systems.

FIGS. 15A and 15B show examples of devices with different types of light source systems. As with other figures provided herein, the numbers, dimensions, types and arrangements of elements shown in FIGS. 15A and 15B are merely presented by way of examples. In these examples, the apparatuses 300 are instances of the apparatus 300 shown in FIG. 3.

In the example shown in FIG. 15A, the light source system 304 does not include a lens 304*b*, whereas in the example shown in FIG. 15B, the light source system 304 includes a lens 304*b*. In this example, the lens 304*b* is a collimating lens, such that the light 203*a* emerging from the lens 304*b* is collimated light. Accordingly, the light 203*a* shown in FIG. 15A is scattered throughout a relatively larger area 505*a* of the finger 206 and the light 203*a* shown in FIG. 15B is concentrated in a relatively smaller area 505*b* of the finger 206.

The present inventors have found that using a lens 304*b* that focuses the light 203*a* into a relatively smaller area of the target object increases the signal-to-noise ratio for desired signals, such as arterial signals. This is believed to be caused in part by the illumination of a relatively larger portion of the target feature(s), such as an artery, when illuminating the target object using a light source system without a lens 304*b*. The illumination of a relatively larger portion of the target feature, which may be at various depths below the skin, causes the resulting photoacoustic signals to be smeared in time. Moreover, when illuminating the target object using a light source system without a lens 304*b*, a relatively larger percentage of the incident light does not reach the target feature(s). In addition, the focusing of the light increases the fluence on the target feature.

Figures 16A, 16B:
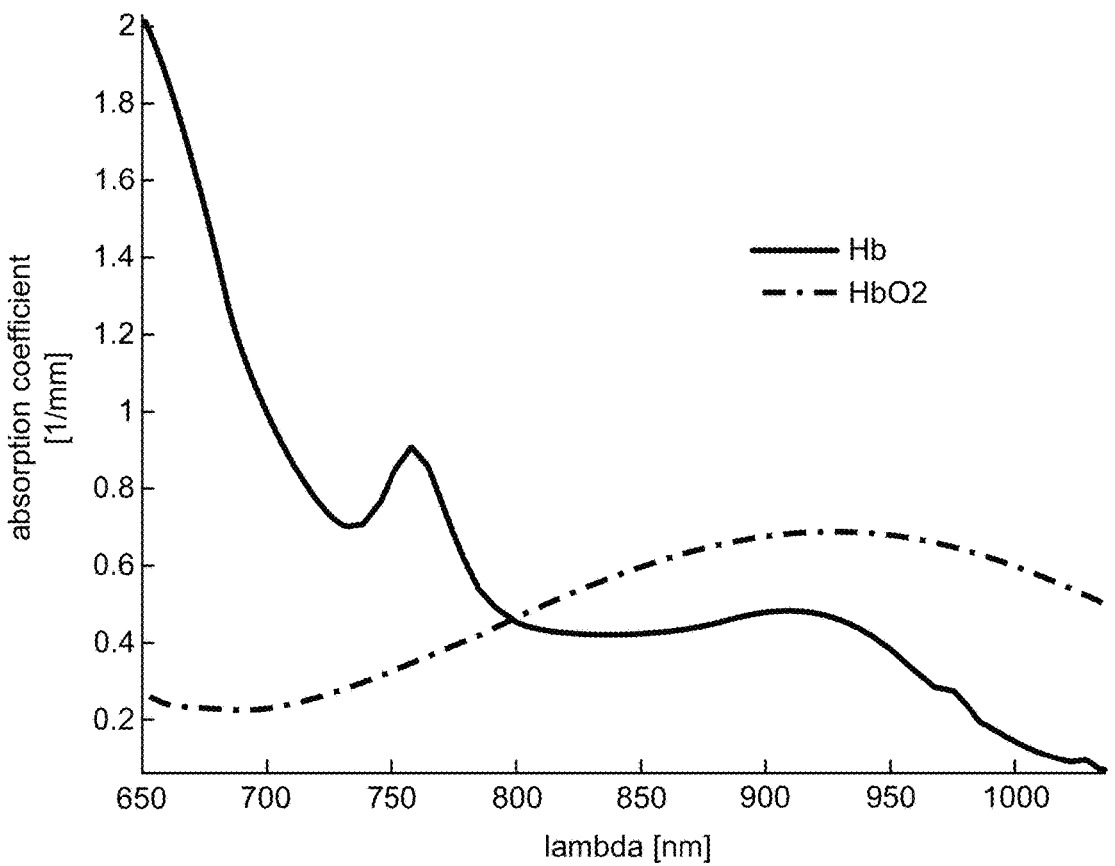
FIG. 16A shows graphs of blood optical absorption coefficient versus wavelength for hemoglobin (Hb) and oxygenated hemoglobin (HbO$_2$).
FIG. 16B shows a table that indicates the maximum permissible exposure (MPE) guidelines for wavelengths of 808 nm and 940 nm.

FIG. 16A shows graphs of blood optical absorption coefficient versus wavelength for hemoglobin (Hb) and oxygenated hemoglobin (HbO$_2$). It may be observed that Hb has an absorption peak at approximately 750 nm and even higher absorption levels between 650 and 700 nm. HbO$_2$ has an absorption peak at approximately 930 nm or 940 nm, with decreasing levels of absorption at shorter and longer wavelengths. Although the Hb absorption levels at approximately 930 nm or 940 nm are not peak values, they are nonetheless a significant fraction of the absorption levels for HbO$_2$ in the same wavelength range.

FIG. 16B shows a table that indicates the maximum permissible exposure (MPE) guidelines for wavelengths of 808 nm and 940 nm. One may observe that the MPE maxima of fluence per pulse and average power density at a wavelength of 808 nm are approximately half of those for 940 nm. Accordingly, a light source (for example a laser diode) that is configured to emit light at wavelengths between 900 and 950 nm may be desirable for PAPG applications, in view of the relatively higher MPE limits and the reasonably high absorption levels for both HbO$_2$ and Hb.

Figure 17A:
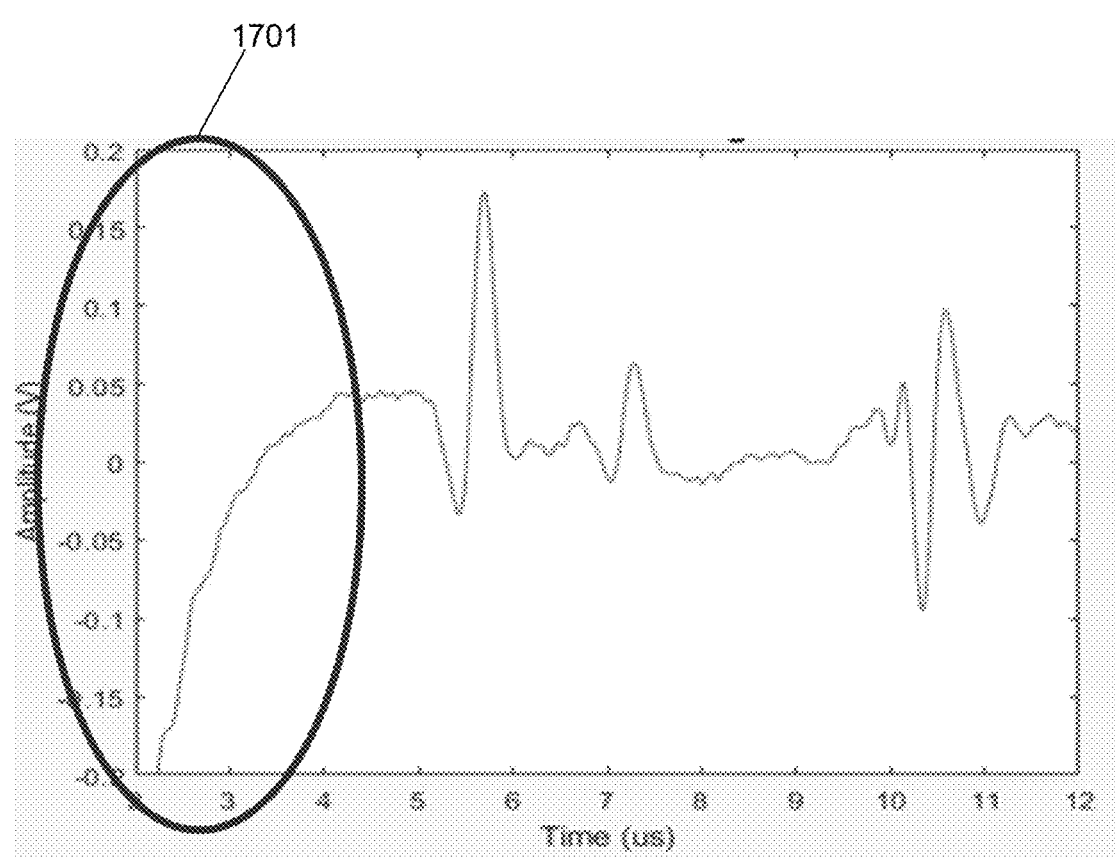
FIG. 17A shows a graph that provides an example of photoacoustic (PA) signals received by a receiver system.

FIG. 17A shows a graph that provides an example of photoacoustic (PA) signals received by a receiver system. During the first few microseconds of the graph, including the time indicated by the oval 1701 in FIG. 17A, large peaks may be observed that have the following contributions: cross-talk from the drive circuitry 1204 of the light source system 304 to the receiver system 302, such as described above with reference to FIGS. 12-14, and irradiation of the receiver system 302 by light from the light source system 304. The tails of these peaks, and the multipaths of these peaks, may in some instances overlay the desired PA signals, thereby reducing the signal-to-noise ratio (SNR) of desired PA signals. The cross-talk from the drive circuitry 1204 to the receiver system 302 tends to scale with the level of current in the drive circuitry 1204.

Figure 17B:
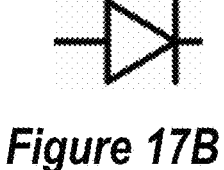
FIG. 17B shows an example of a single-junction laser diode implementation.
Figure 17C:
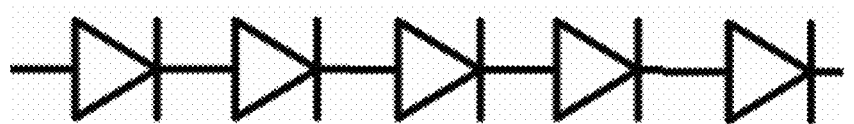
FIG. 17C shows an example of a multiple-junction laser diode implementation, which includes 5 junctions in this example.

FIG. 17B shows an example of a single-junction laser diode implementation. FIG. 17C shows an example of a multiple-junction laser diode implementation, which includes 5 junctions in this example. Other multiple-junction laser diode implementations may include more or fewer junctions, such as 2, 3, 4, 6, 7, 8, 9 or 10 junctions. The laser diode implementations may, for example, include VCSELs or edge-emitting lasers (EELs). Increasing the number of junctions increases the voltage, but decreases the current. Therefore, multiple-junction laser diode implementations can reduce the levels of cross-talk from the drive circuitry 1204 to the receiver system 302, thereby providing a higher SNR.

FIG. 18 is a flow diagram that shows examples of some disclosed operations. The blocks of FIG. 18 (and those of other flow diagrams provided herein) may, for example, be performed by the apparatus 300 of FIG. 3 or by a similar apparatus. As with other methods disclosed herein, the method outlined in FIG. 18 may include more or fewer blocks than indicated. Moreover, the blocks of methods disclosed herein are not necessarily performed in the order indicated. In some instances, one or more of the blocks shown in FIG. 18 may be performed concurrently.

In this example, block 1805 involves controlling, by a control system, a light source system to emit light towards a target object on, or proximate, an outer surface of a platen. The target object may be a finger, a wrist, etc., depending on the particular example. According to this example, block 1810 involves receiving, by the control system, signals from the ultrasonic receiver system corresponding to ultrasonic waves generated by the target object responsive to the light emitted by the light source system.

According to this example, block 1815 involves identifying, by the control system, arterial signals from the ultrasonic receiver system corresponding to ultrasonic waves generated by blood within an artery of the target object. The arterial signals may, for example, be identified implementing a RGD that corresponds with the expected depth to an artery.

In this example, block 1820 involves estimating, by the control system, one or more cardiac features based, at least in part, on the arterial signals. In some examples, block 1820 may involve estimating a blood pressure based, at least in part, on the arterial signals. According to some examples, block 1820, or another aspect of method 1800, may involve extracting and evaluating heart rate waveform (HRW) features.

Figure 19:
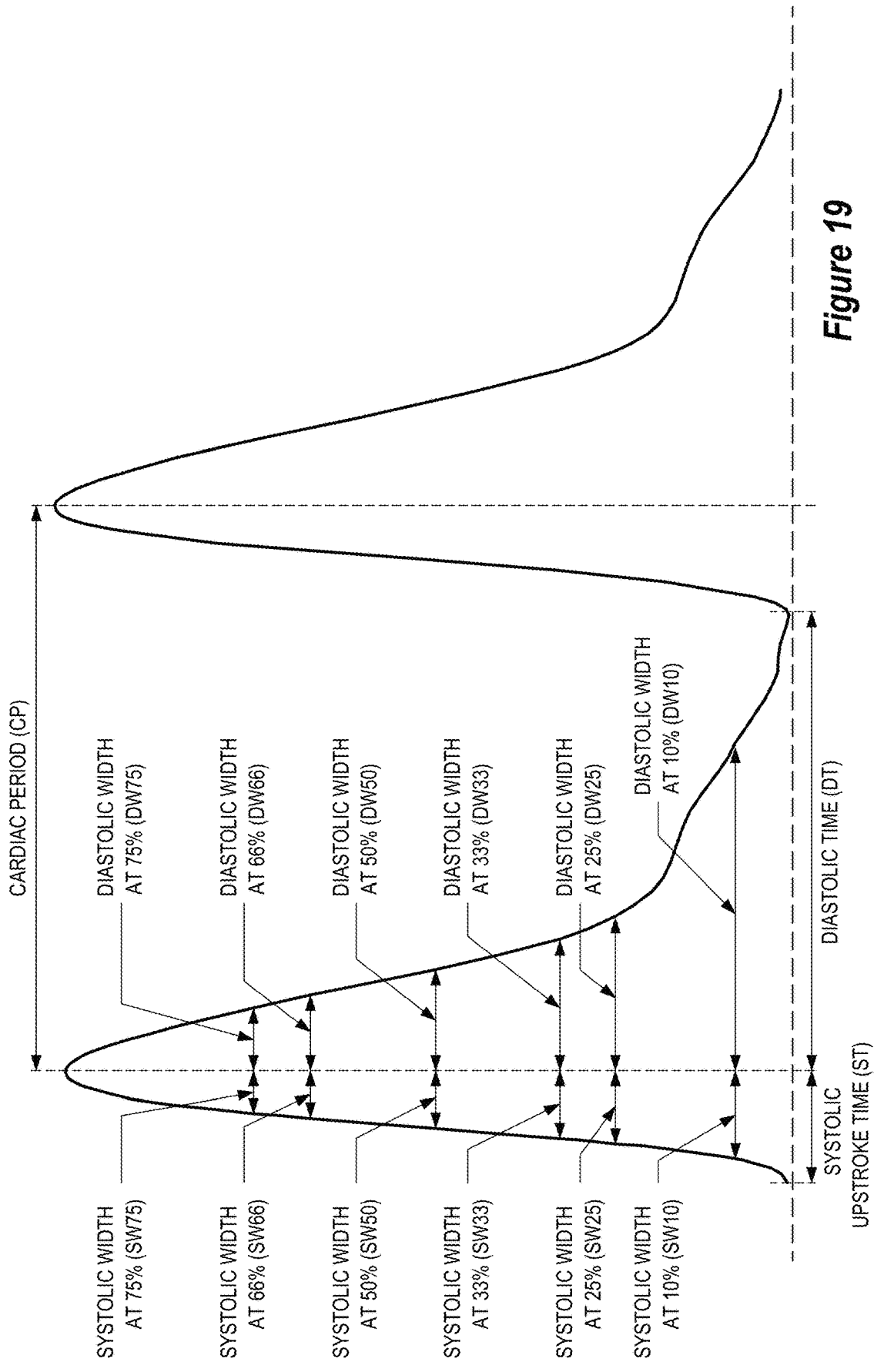
FIG. 19 shows examples of heart rate waveform (HRW) features that may be extracted according to some implementations.

FIG. 19 shows examples of heart rate waveform (HRW) features that may be extracted according to some implementations. The horizontal axis of FIG. 19 represents time and the vertical axis represents signal amplitude. The cardiac period is indicated by the time between adjacent peaks of the HRW. The systolic and diastolic time intervals are indicated below the horizontal axis. During the systolic phase of the cardiac cycle, as a pulse propagates through a particular location along an artery, the arterial walls expand according to the pulse waveform and the elastic properties of the arterial walls. Along with the expansion is a corresponding increase in the volume of blood at the particular location or region, and with the increase in volume of blood an associated change in one or more characteristics in the region. Conversely, during the diastolic phase of the cardiac cycle, the blood pressure in the arteries decreases and the arterial walls contract. Along with the contraction is a corresponding decrease in the volume of blood at the particular location, and with the decrease in volume of blood an associated change in the one or more characteristics in the region.

The HRW features that are illustrated in FIG. 19 pertain to the width of the systolic and/or diastolic portions of the HRW curve at various "heights," which are indicated by a percentage of the maximum amplitude. For example, the SW50 feature is the width of the systolic portion of the HRW curve at a "height" of 50% of the maximum amplitude. In some implementations, the HRW features used for blood pressure estimation may include some or all of the SW10, SW25, SW33, SW50, SW66, SW75, DW10, DW25, DW33, DW50, DW66 and DW75 HRW features. In other implementations, additional HRW features may be used for blood pressure estimation. Such additional HRW features may, in some instances, include the sum and ratio of the SW and DW at one or more "heights," e.g., (DW75+SW75), DW75/SW75, (DW66+SW66), DW66/SW66, (DW50+SW50), DW50/SW50, (DW33+SW33), DW33/SW33, (DW25+SW25), DW25/SW25 and/or (DW10+SW10), DW10/SW10. Other implementations may use yet other HRW features for blood pressure estimation. Such additional HRW features may, in some instances, include sums, differences, ratios and/or other operations based on more than one "height," such as (DW75+SW75)/(DW50+SW50), (DW50+SW50/(DW10+SW10), etc.

Figure 20:
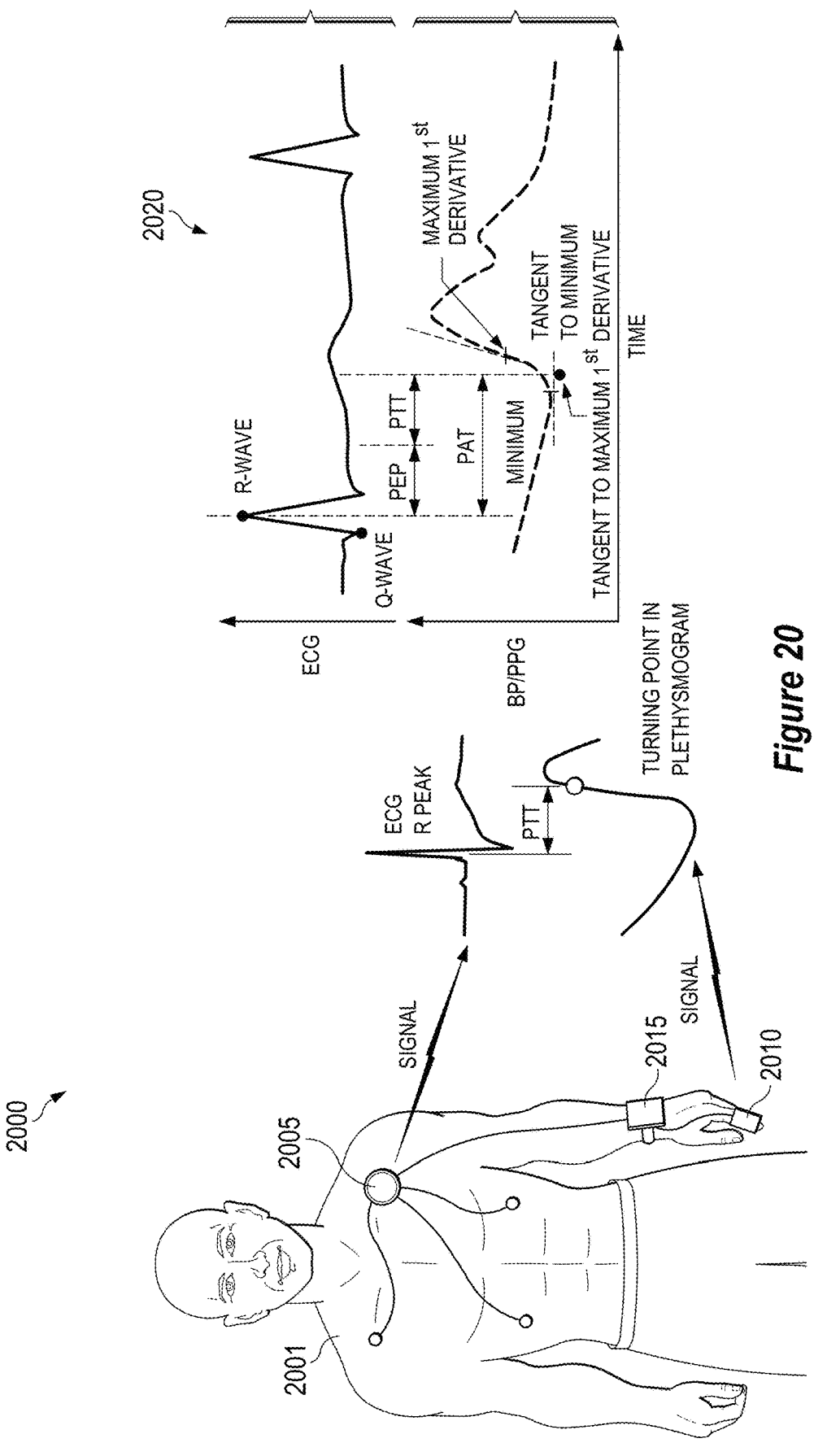
FIG. 20 shows examples of devices that may be used in a system for estimating blood pressure based, at least in part, on pulse transit time (PTT).

FIG. 20 shows examples of devices that may be used in a system for estimating blood pressure based, at least in part, on pulse transit time (PTT). As with other figures provided herein, the numbers, types and arrangements of elements are merely presented by way of example. According to this example, the system 2000 includes at least two sensors. In this example, the system 2000 includes at least an electrocardiogram sensor 2005 and a device 2010 that is configured to be mounted on a finger of the person 2001. In this example, the device 2010 is, or includes, an apparatus configured to perform at least some PAPG methods disclosed herein. For example, the device 2010 may be, or may include, the apparatus 200 of FIG. 2 or a similar apparatus.

As noted in the graph 2020, the PAT includes two components, the pre-ejection period (PEP, the time needed to convert the electrical signal into a mechanical pumping force and isovolumetric contraction to open the aortic valves) and the PTT. The starting time for the PAT can be estimated based on the QRS complex—an electrical signal characteristic of the electrical stimulation of the heart ventricles. As shown by the graph 2020, in this example the beginning of a pulse arrival time (PAT) may be calculated according to an R-Wave peak measured by the electrocardiogram sensor 2005 and the end of the PAT may be detected via analysis of signals provided by the device 2010. In this example, the end of the PAT is assumed to correspond with an intersection between a tangent to a local minimum value detected by the device 2010 and a tangent to a maximum slope/first derivative of the sensor signals after the time of the minimum value.

There are many known algorithms for blood pressure estimation based on the PTT and/or the PAT, some of which are summarized in Table 1 of Sharma, M., et al., *Cuff-Less and Continuous Blood Pressure Monitoring: a Methodological Review* ("Sharma"), in Multidisciplinary Digital Publishing Institute (MDPI) Technologies 2017, 5, 21, and which are described in the corresponding text on pages 5-10 of Sharma, both of which are hereby incorporated by reference.

Other implementations of the system 2000 may not include the electrocardiogram sensor 2005. In some such implementations, the device 2015, which is configured to be mounted on a wrist of the person 2001, may be, or may include, an apparatus configured to perform at least some PAPG methods disclosed herein. For example, the device 2015 may be, or may include, the apparatus 200 of FIG. 2 or a similar apparatus. According to some such examples, the device 2015 may include a light source system and two or more ultrasonic receivers. In some examples, the device 2015 may include at least one array of ultrasonic receivers.

Figure 21:
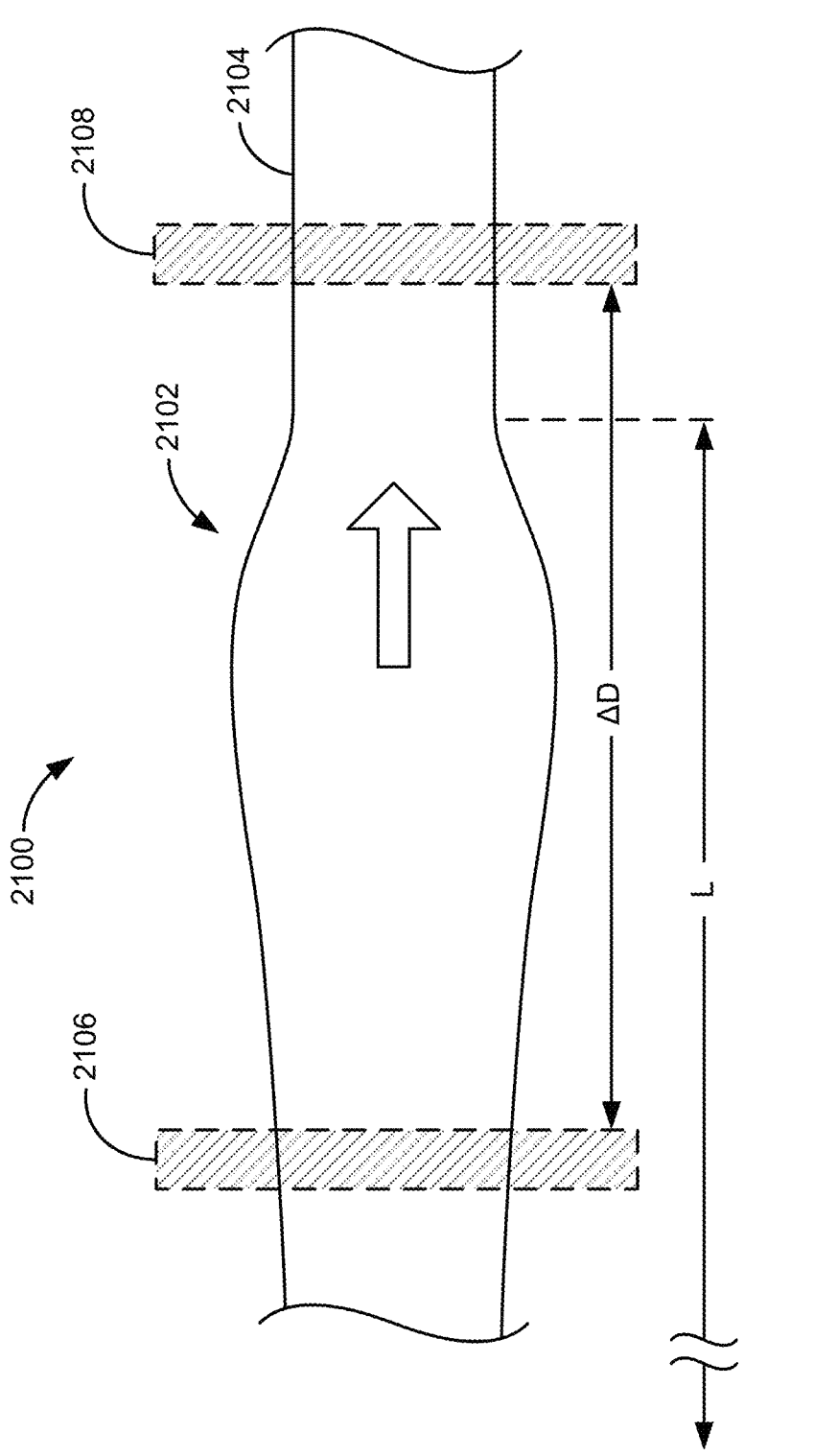
FIG. 21 shows a cross-sectional side view of a diagrammatic representation of a portion of an artery through which a pulse is propagating.

FIG. 21 shows a cross-sectional side view of a diagrammatic representation of a portion of an artery 2100 through which a pulse 2102 is propagating. The block arrow in FIG. 21 shows the direction of blood flow and pulse propagation. As diagrammatically shown, the propagating pulse 2102 causes strain in the arterial walls 2104, which is manifested in the form of an enlargement in the diameter (and consequently the cross-sectional area) of the arterial walls— referred to as "distension." The spatial length L of an actual propagating pulse along an artery (along the direction of blood flow) is typically comparable to the length of a limb, such as the distance from a subject's shoulder to the subject's wrist or finger, and is generally less than one meter (m). However, the length L of a propagating pulse can vary considerably from subject to subject, and for a given subject, can vary significantly over durations of time depending on various factors. The spatial length L of a pulse will generally decrease with increasing distance from the heart until the pulse reaches capillaries.

As described above, some particular implementations relate to devices, systems and methods for estimating blood pressure or other cardiovascular characteristics based on estimates of an arterial distension waveform. The terms "estimating," "measuring," "calculating," "inferring," "deducing," "evaluating," "determining" and "monitoring" may be used interchangeably herein where appropriate unless otherwise indicated. Similarly, derivations from the roots of these terms also are used interchangeably where appropriate; for example, the terms "estimate," "measurement," "calculation," "inference" and "determination" also are used interchangeably herein. In some implementations, the pulse wave velocity (PWV) of a propagating pulse may be estimated by measuring the pulse transit time (PTT) of the pulse as it propagates from a first physical location along an artery to another more distal second physical location along the artery. It will be appreciated that this PTT is different from the PTT that is described above with reference to FIG. 15. However, either version of the PTT may be used for the purpose of blood pressure estimation. Assuming that the physical distance $\Delta D$ between the first and the second physical locations is ascertainable, the PWV can be estimated as the quotient of the physical spatial distance $\Delta D$ traveled by the pulse divided by the time (PTT) the pulse takes in traversing the physical spatial distance $\Delta D$. Generally, a first sensor positioned at the first physical location is used to determine a starting time (also referred to herein as a "first temporal location") at which point the pulse arrives at or propagates through the first physical location. A second sensor at the second physical location is used to determine an ending time (also referred to herein as a "second temporal location") at which point the pulse arrives at or propagates through the second physical location and continues through the remainder of the arterial branch. In such examples, the PTT represents the temporal distance (or time difference) between the first and the second temporal locations (the starting and the ending times).

The fact that measurements of the arterial distension waveform are performed at two different physical locations implies that the estimated PWV inevitably represents an average over the entire path distance ΔD through which the pulse propagates between the first physical location and the second physical location. More specifically, the PWV generally depends on a number of factors including the density ρ of the blood ρ, the stiffness E of the arterial wall (or inversely the elasticity), the arterial diameter, the thickness of the arterial wall, and the blood pressure. Because both the arterial wall elasticity and baseline resting diameter (for example, the diameter at the end of the ventricular diastole period) vary significantly throughout the arterial system, PWV estimates obtained from PTT measurements are inherently average values (averaged over the entire path length ΔD between the two locations where the measurements are performed).

In traditional methods for obtaining PWV, the starting time of the pulse has been obtained at the heart using an electrocardiogram (ECG) sensor, which detects electrical signals from the heart. For example, the starting time can be estimated based on the QRS complex—an electrical signal characteristic of the electrical stimulation of the heart ventricles. In such approaches, the ending time of the pulse is typically obtained using a different sensor positioned at a second location (for example, a finger). As a person having ordinary skill in the art will appreciate, there are numerous arterial discontinuities, branches, and variations along the entire path length from the heart to the finger. The PWV can change by as much as or more than an order of magnitude along various stretches of the entire path length from the heart to the finger. As such, PWV estimates based on such long path lengths are unreliable.

In various implementations described herein, PTT estimates are obtained based on measurements (also referred to as "arterial distension data" or more generally as "sensor data") associated with an arterial distension signal obtained by each of a first arterial distension sensor 2106 and a second arterial distension sensor 2108 proximate first and second physical locations, respectively, along an artery of interest. In some particular implementations, the first arterial distension sensor 2106 and the second arterial distension sensor 2108 are advantageously positioned proximate first and second physical locations between which arterial properties of the artery of interest, such as wall elasticity and diameter, can be considered or assumed to be relatively constant. In this way, the PWV calculated based on the PTT estimate is more representative of the actual PWV along the particular segment of the artery. In turn, the blood pressure P estimated based on the PWV is more representative of the true blood pressure. In some implementations, the magnitude of the distance ΔD of separation between the first arterial distension sensor 2106 and the second arterial distension sensor 2108 (and consequently the distance between the first and the second locations along the artery) can be in the range of about 1 centimeter (cm) to tens of centimeters—long enough to distinguish the arrival of the pulse at the first physical location from the arrival of the pulse at the second physical location, but close enough to provide sufficient assurance of arterial consistency. In some specific implementations, the distance ΔD between the first and the second arterial distension sensors 2106 and 2108 can be in the range of about 1 cm to about 30 cm, and in some implementations, less than or equal to about 20 cm, and in some implementations, less than or equal to about 10 cm, and in some specific implementations less than or equal to about 5 cm. In some other implementations, the distance ΔD between the first and the second arterial distension sensors 2106 and 2108 can be less than or equal to 1 cm, for example, about 0.1 cm, about 0.25 cm, about 0.5 cm or about 0.75 cm. By way of reference, a typical PWV can be about 15 meters per second (m/s). Using an ambulatory monitoring device in which the first and the second arterial distension sensors 2106 and 2108 are separated by a distance of about 5 cm, and assuming a PWV of about 15 m/s implies a PTT of approximately 3.3 milliseconds (ms).

The value of the magnitude of the distance ΔD between the first and the second arterial distension sensors 2106 and 2108, respectively, can be preprogrammed into a memory within a monitoring device that incorporates the sensors (for example, such as a memory of, or a memory configured for communication with, the control system 206 that is described above with reference to FIG. 2). As will be appreciated by a person of ordinary skill in the art, the spatial length L of a pulse can be greater than the distance ΔD from the first arterial distension sensor 2106 to the second arterial distension sensor 2108 in such implementations. As such, although the diagrammatic pulse 2102 shown in FIG. 21 is shown as having a spatial length L comparable to the distance between the first arterial distension sensor 2106 and the second arterial distension sensor 2108, in actuality each pulse can typically have a spatial length L that is greater and even much greater than (for example, about an order of magnitude or more than) the distance ΔD between the first and the second arterial distension sensors 2106 and 2108.

Implementation examples are described in the following numbered clauses:

1. An apparatus, comprising: a platen; a light source system configured for providing light to a target object on an outer surface of the platen; an ultrasonic receiver system configured to receive ultrasonic waves generated by the target object, responsive to the light from the light source system; and a mirror layer residing between the ultrasonic receiver system and the platen, the mirror layer configured to reflect light from the light source system.

2. The apparatus of clause 1, wherein the platen is configured to increase an intensity of ultrasonic energy received by at least a portion of the ultrasonic receiver system.

3. The apparatus of clause 1 or clause 2, wherein the platen includes an acoustic waveguide.

4. The apparatus of any one of clauses 1-3, wherein the platen includes an acoustic lens.

5. The apparatus of clause 4, wherein the acoustic lens resides on, or proximate, the outer surface of the platen.

6. The apparatus of clause 4 or clause 5, wherein the acoustic lens comprises a spherical lens or a cylindrical lens.

7. The apparatus of any one of clauses 1-6, wherein the platen, the light source system, or a combination thereof, is configured for transmitting light from the light source system to the outer surface of the platen along a first axis, or substantially along the first axis.

8. The apparatus of clause 7, wherein the platen is configured for transmitting the ultrasonic waves generated by the target object along a second axis, or substantially along the second axis, the second axis being different from the first axis.

9. The apparatus of clause 7, wherein the platen is configured for transmitting the ultrasonic waves generated by the target object along a second axis, or substantially along the second axis, the second axis being parallel to the first axis.

10. The apparatus of any one of clauses 1-9, wherein at least one surface of the platen comprises an anti-reflective layer.

11. The apparatus of any one of clauses 1-10, wherein the ultrasonic receiver system comprises two or more receiver elements adjacent to a region of the platen through which light from the light source is transmitted towards the target object.

12. The apparatus of any one of clauses 1-11, wherein the platen, the light source system, or a combination thereof, is configured for transmitting light in the near infrared range.

13. The apparatus of any one of clauses 1-12, wherein the apparatus is, or includes, a mobile device and wherein the outer surface of the platen corresponds with, or is proximate, an outer surface of the mobile device.

14. The apparatus of clause 13, wherein the mobile device comprises a cellular telephone.

15. The apparatus of clause 13, wherein the mobile device comprises a pen or a stylus.

16. The apparatus of clause 15, wherein the pen or the stylus includes a force sensor, a motion sensor, a spring, or combinations thereof.

17. The apparatus of any one of clauses 1-16, wherein a thickness of the platen, an acoustic velocity of the platen, or a combination thereof, are configured to separate ultrasonic waves generated by blood in an artery from other ultrasonic waves.

18. The apparatus of any one of clauses 1-17, wherein the platen provides an acoustic attenuation of the ultrasonic waves in a range from 0.3-3.0 decibels per centimeter per megahertz.

19. The apparatus of any one of clauses 1-18, wherein at least an outer surface of the platen has an acoustic imped-ance that is configured to approximate an acoustic imped-ance of human skin.

20. The apparatus of any one of clauses 1-19, wherein at least an outer surface of the platen is configured to conform to a surface of human skin.

21. The apparatus of any one of clauses 1-20, wherein a speed of sound in the platen is in a range from 800-3000 meters per second.

22. The apparatus of any one of clauses 1-21, further comprising a control system configured to: control the light source system to emit light; receive signals from the ultra-sonic receiver system corresponding to the ultrasonic waves generated by the target object; identify arterial blood signals from the ultrasonic receiver system corresponding to ultra-sonic waves generated by blood within an artery of the target object; and estimate one or more cardiac features based, at least in part, on the arterial blood signals.

23. The apparatus of any one of clauses 1-21, further comprising a control system configured to: control the light source system to emit light; receive signals from the ultra-sonic receiver system corresponding to the ultrasonic waves generated by the target object; identify one or more arterial wall signals from the ultrasonic receiver system correspond-ing to ultrasonic waves generated by one or more arterial walls of the target object; and estimate one or more cardiac features based, at least in part, on the one or more arterial wall signals.

24. The apparatus of any one of clauses 1-23, further comprising one or more optical waveguides.

25. The apparatus of clause 24, wherein at least a portion of one of the one or more optical waveguides resides in a portion of the platen.

26. An apparatus, comprising: a platen; light source means for providing light to a target object on, or proximate, an outer surface of the platen; an ultrasonic receiver system configured to receive ultrasonic waves generated by the target object, responsive to the light from the light source means; and a mirror layer residing between the ultrasonic receiver system and the platen, the mirror layer configured to reflect light from the light source means.

27. The apparatus of clause 26, wherein the platen is configured to increase an intensity of ultrasonic energy received by at least a portion of the ultrasonic receiver system.

28. The apparatus of clause 26 or clause 27, wherein the platen includes an acoustic waveguide.

29. The apparatus of any one of clauses 26-28, wherein the platen includes an acoustic lens.

30. A method, comprising: controlling, by a control sys-tem, a light source system to emit light to a target object on an outer surface of a platen; receiving, by the control system, signals from an ultrasonic receiver system corresponding to the ultrasonic waves generated by a target object; identify-ing, by the control system, arterial signals from the ultra-sonic receiver system corresponding to ultrasonic waves generated by blood within an artery of the target object, generated by one or more arterial walls of the target object, or a combination thereof; and estimating, by the control system, one or more cardiac features based, at least in part, on the arterial blood signals.

31. The method of clause 30, wherein controlling the light source system to emit light involves controlling the light source system to emit laser pulses.

32. An apparatus, comprising: a platen; a light source system configured for providing light to a target object on an outer surface of the platen, the light source system including one or more laser diodes and a drive circuit; an ultrasonic receiver system configured to receive ultrasonic waves gen-erated by the target object, responsive to the light from the light source system; and a noise reduction system including one or more noise reduction elements configured to at least partially decouple acoustic energy produced by the light source system, electrical energy produced by the light source system, light produced by the light source system, or com-binations thereof, from the ultrasonic receiver system.

33. The apparatus of clause 32, wherein the noise reduc-tion system includes one or more electromagnetically shielded transmission wires of the light source system.

34. The apparatus of clause 33, wherein the one or more electromagnetically shielded transmission wires are config-ured to reduce electromagnetic interference from the light source system that is received by the ultrasonic receiver system.

35. The apparatus of any one of clauses 32-34, wherein the noise reduction system includes one or more air gaps between the light source system and the ultrasonic receiver system.

36. The apparatus of any one of clauses 32-35, wherein the noise reduction system includes one or more sound-absorbing layers configured to reduce the acoustic energy produced by the light source system that is received by the ultrasonic receiver system.

37. The apparatus of clause 36, wherein at least one of the one or more sound-absorbing layers resides in, or proximate, the ultrasonic receiver system.

38. The apparatus of clause 36 or clause 37, wherein at least one of the one or more sound-absorbing layers resides in, or proximate, the light source system.

39. The apparatus of any one of clauses 32-38, wherein the noise reduction system includes one or more light-absorbing layers configured to reduce an amount of light produced by the light source system that is received by the ultrasonic receiver system.

40. The apparatus of clause 39, wherein at least one of the one or more light-absorbing layers resides in, or proximate, the ultrasonic receiver system.

41. The apparatus of any one of clauses 32-40, wherein the noise reduction system includes one or more reflective layers configured to reduce an amount of light produced by the light source system that is received by the ultrasonic receiver system.

42. The apparatus of clause 41, wherein at least one of the one or more reflective layers resides between the platen and at least a portion of the ultrasonic receiver system.

43. The apparatus of any one of clauses 32-42, wherein the light source system includes at least one multi-junction laser diode.

44. The apparatus of any one of clauses 32-43, wherein the light source system includes a lens configured to collimate light produced by the light source system.

45. The apparatus of any one of clauses 32-44, wherein the platen, the light source system, or a combination thereof, is configured for transmitting light from the light source system to the outer surface of the platen along a first axis, or substantially along the first axis.

46. The apparatus of clause 45, wherein the platen is configured for transmitting the ultrasonic waves generated by the target object along a second axis, or substantially along the second axis, the second axis being different from the first axis.

47. The apparatus of clause 45, wherein the platen is configured for transmitting the ultrasonic waves generated by the target object along a second axis, or substantially along the second axis, the second axis being parallel to the first axis.

48. The apparatus of clause 47, wherein the ultrasonic receiver system comprises two or more receiver elements adjacent to a region of the platen through which light from the light source system is transmitted towards the target object.

49. The apparatus of any one of clauses 32-48, further comprising a control system configured to: control the light source system to emit light; receive signals from the ultrasonic receiver system corresponding to the ultrasonic waves generated by the target object; identify one or more arterial wall signals from the ultrasonic receiver system corresponding to ultrasonic waves generated by one or more arterial walls of the target object; and estimate one or more cardiac features based, at least in part, on the one or more arterial wall signals.

50. The apparatus of any one of clauses 32-49, wherein the light source system is configured for transmitting light in a wavelength range of 800 to 900 nanometers.

51. The apparatus of any one of clauses 32-50, wherein the light source system is configured for transmitting light in a wavelength range of 500 to 600 nanometers.

52. The apparatus of any one of clauses 32-51, wherein the light source system includes one or more light-emitting diodes, one or more vertical cavity surface-emitting lasers, one or more edge emitting lasers, or combinations thereof.

53. The apparatus of any one of clauses 32-52, wherein the drive circuit is configured to cause the light source system to emit pulses of light at pulse widths in a range from 3 nanoseconds to 1000 nanoseconds.

54. The apparatus of any one of clauses 32-53, wherein the drive circuit is configured to cause the light source system to emit pulses of light at pulse repetition frequencies in a range from 1 kilohertz to 100 kilohertz.

55. The apparatus of any one of clauses 32-54, wherein the apparatus is, or includes, a mobile device and wherein the outer surface of the platen corresponds with, or is proximate, an outer surface of the mobile device.

56. The apparatus of clause 55, wherein the mobile device comprises a cellular telephone.

57. The apparatus of clause 55, wherein the mobile device comprises a pen or a stylus.

58. The apparatus of clause 57, wherein the pen or the stylus includes a force sensor, a motion sensor, a spring, or combinations thereof.

59. The apparatus of any one of clauses 32-58, further comprising a control system configured to: control the light source system to emit light; receive signals from the ultrasonic receiver system corresponding to the ultrasonic waves generated by the target object; identify one or more arterial signals from the ultrasonic receiver system corresponding to ultrasonic waves generated by blood within an artery of the target object, generated by one or more arterial walls, or combinations thereof; and estimate one or more cardiac features based, at least in part, on the one or more arterial signals.

60. The apparatus of any one of clauses 32-59, further comprising one or more optical waveguides.

61. The apparatus of clause 60, wherein at least a portion of one of the one or more optical waveguides resides in a portion of the platen.

62. An apparatus, comprising: a platen; light source means for providing light to a target object on an outer surface of the platen, the light source means including one or more laser diodes and a drive circuit; an ultrasonic receiver system configured to receive ultrasonic waves generated by the target object, responsive to the light from the light source means; and a noise reduction system including one or more noise reduction elements configured to at least partially decouple acoustic energy produced by the light source means, electrical energy produced by the light source means, light produced by the light source means, or combinations thereof, from the ultrasonic receiver system.

63. The apparatus of clause 62, wherein the noise reduction system includes one or more electromagnetically shielded transmission wires of the light source means.

64. The apparatus of clause 63, wherein the one or more electromagnetically shielded transmission wires are configured to reduce electromagnetic interference from the light source means that is received by the ultrasonic receiver system.

65. A method, comprising: controlling, by a control system, a light source system to emit light to a target object on an outer surface of a platen; receiving, by the control system, signals from an ultrasonic receiver system corresponding to the ultrasonic waves generated by a target object; identifying, by the control system, arterial signals from the ultrasonic receiver system corresponding to ultrasonic waves generated by blood within an artery of the target object, generated by one or more arterial walls of the target object, or a combination thereof; and estimating, by the control system, one or more cardiac features based, at least in part, on the arterial blood signals.

66. The method of clause 65, wherein controlling the light source system to emit light involves controlling the light source system to emit laser pulses.

67. An apparatus, comprising: a platen; a light source system configured for providing light to a target object on an outer surface of the platen, the light source system including one or more laser diodes and a drive circuit, the one or more laser diodes including at least one multi-junction laser diode; and an ultrasonic receiver system configured to receive ultrasonic waves generated by the target object, responsive to the light from the light source system.

68. The apparatus of clause 67, further comprising a noise reduction system including one or more noise reduction elements configured to at least partially decouple acoustic energy produced by the light source system, electrical energy produced by the light source system, light produced by the light source system, or combinations thereof, from the ultrasonic receiver system.

69. The apparatus of clause 68, wherein the noise reduction system includes one or more electromagnetically shielded transmission wires of the light source system.

70. The apparatus of clause 69, wherein the one or more electromagnetically shielded transmission wires are configured to reduce electromagnetic interference from the light source system that is received by the ultrasonic receiver system.

71. The apparatus of any one of clauses 68-70, wherein the noise reduction system includes one or more air gaps between the light source system and the ultrasonic receiver system.

72. The apparatus of any one of clauses 68-71, wherein the noise reduction system includes one or more sound-absorbing layers configured to reduce the acoustic energy produced by the light source system that is received by the ultrasonic receiver system.

73. The apparatus of clause 72, wherein at least one of the one or more sound-absorbing layers resides in, or proximate, the ultrasonic receiver system.

74. The apparatus of clause 72 or clause 73, wherein at least one of the one or more sound-absorbing layers resides in, or proximate, the light source system.

75. The apparatus of any one of clauses 68-74, wherein the noise reduction system includes one or more light-absorbing layers configured to reduce an amount of light produced by the light source system that is received by the ultrasonic receiver system.

76. The apparatus of clause 75, wherein at least one of the one or more light-absorbing layers resides in, or proximate, the ultrasonic receiver system.

77. The apparatus of any one of clauses 68-76, wherein the noise reduction system includes one or more reflective layers configured to reduce an amount of light produced by the light source system that is received by the ultrasonic receiver system.

78. The apparatus of clause 77, wherein at least one of the one or more reflective layers resides between the platen and at least a portion of the ultrasonic receiver system.

79. The apparatus of any one of clauses 67-78, wherein the light source system includes a lens configured to collimate light produced by the light source system.

80. The apparatus of any one of clauses 67-79, wherein the platen, the light source system, or a combination thereof, is configured for transmitting light from the light source system to the outer surface of the platen along a first axis, or substantially along the first axis.

81. The apparatus of clause 80, wherein the platen is configured for transmitting the ultrasonic waves generated by the target object along a second axis, or substantially along the second axis, the second axis being different from the first axis.

82. The apparatus of clause 80, wherein the platen is configured for transmitting the ultrasonic waves generated by the target object along a second axis, or substantially along the second axis, the second axis being parallel to the first axis.

83. The apparatus of any one of clauses 67-82, further comprising a control system configured to: control the light source system to emit light; receive signals from the ultrasonic receiver system corresponding to the ultrasonic waves generated by the target object; identify one or more arterial wall signals from the ultrasonic receiver system corresponding to ultrasonic waves generated by one or more arterial walls of the target object; and estimate one or more cardiac features based, at least in part, on the one or more arterial wall signals.

84. The apparatus of any one of clauses 67-83, wherein the ultrasonic receiver system comprises two or more receiver elements adjacent to a region of the platen through which light from the light source system is transmitted towards the target object.

85. The apparatus of any one of clauses 67-84, wherein the light source system is configured for transmitting light in a wavelength range of 800 to 950 nanometers.

86. The apparatus of any one of clauses 67-85, wherein the light source system is configured for transmitting light in a wavelength range of 500 to 600 nanometers.

87. The apparatus of any one of clauses 67-86, wherein the light source system includes one or more light-emitting diodes, one or more vertical cavity surface-emitting lasers, one or more edge emitting lasers, or combinations thereof.

88. The apparatus of any one of clauses 67-87, wherein the drive circuit is configured to cause the light source system to emit pulses of light at pulse widths in a range from 3 nanoseconds to 1000 nanoseconds.

89. The apparatus of any one of clauses 67-88, wherein the drive circuit is configured to cause the light source system to emit pulses of light at pulse repetition frequencies in a range from 1 kilohertz to 100 kilohertz.

90. The apparatus of any one of clauses 67-89, wherein the apparatus is, or includes, a mobile device and wherein the outer surface of the platen corresponds with, or is proximate, an outer surface of the mobile device.

91. The apparatus of clause 90, wherein the mobile device comprises a cellular telephone.

92. The apparatus of clause 90, wherein the mobile device comprises a pen or a stylus.

93. The apparatus of clause 92, wherein the pen or the stylus includes a force sensor, a motion sensor, a spring, or combinations thereof.

94. The apparatus of any one of clauses 67-93, further comprising a control system configured to: control the light source system to emit light; receive signals from the ultrasonic receiver system corresponding to the ultrasonic waves generated by the target object; identify one or more arterial blood signals from the ultrasonic receiver system corresponding to ultrasonic waves generated by blood within an artery of the target object; and estimate one or more cardiac features based, at least in part, on the one or more arterial blood signals.

95. The apparatus of any one of clauses 67-94, further comprising one or more optical waveguides.

96. The apparatus of clause 95, wherein at least a portion of one of the one or more optical waveguides resides in a portion of the platen.

97. An apparatus, comprising: a platen; light source means for providing light to a target object on an outer surface of the platen, the light source means including one or more laser diodes and a drive circuit, the one or more laser diodes including at least one multi-junction laser diode; and an ultrasonic receiver system configured to receive ultrasonic waves generated by the target object, responsive to the light from the light source means.

98. The apparatus of clause 97, further comprising a noise reduction system including one or more noise reduction elements configured to at least partially decouple acoustic energy produced by the light source means, electrical energy produced by the light source means, light produced by the light source means, or combinations thereof, from the ultrasonic receiver system.

99. The apparatus of clause 98, wherein the noise reduction system includes one or more electromagnetically shielded transmission wires of the light source means.

100. A method, comprising: controlling, by a control system, a light source system to emit light to a target object on an outer surface of a platen; receiving, by the control system, signals from an ultrasonic receiver system corresponding to the ultrasonic waves generated by a target object; identifying, by the control system, arterial signals from the ultrasonic receiver system corresponding to ultrasonic waves generated by blood within an artery of the target object, generated by one or more arterial walls of the target object, or a combination thereof; and estimating, by the control system, one or more cardiac features based, at least in part, on the arterial blood signals.

101. The method of clause 100, wherein controlling the light source system to emit light involves controlling the light source system to emit laser pulses.

102. An apparatus, comprising: a platen; a light source system configured for providing light to a target object on an outer surface of the platen; and an ultrasonic receiver configured to receive ultrasonic waves generated by the target object, responsive to the light from the light source system, wherein one or more platen characteristics that include a thickness of the platen, an acoustic velocity of the platen, or a combination thereof, are configured to separate received one or more arterial ultrasonic waves generated by blood in an artery, by an arterial wall, or by a combination thereof, from one or more other types of received ultrasonic waves.

103. The apparatus of clause 102, wherein the one or more other types of received ultrasonic waves include reflected ultrasonic waves emitted by the ultrasonic receiver that have reflected from the target object.

104. The apparatus of clause 103, wherein the one or more platen characteristics cause the reflected ultrasonic waves emitted by the ultrasonic receiver to be received by the ultrasonic receiver after the one or more arterial ultrasonic waves.

105. The apparatus of any one of clauses 102-104, wherein a speed of sound in the platen is in a range from 800-3000 meters per second.

106. The apparatus of any one of clauses 102-105, wherein the thickness of the platen is in a range from 5-40 millimeters.

107. The apparatus of any one of clauses 102-106, wherein the platen is configured to increase an intensity of ultrasonic energy received by at least a portion of the ultrasonic receiver.

108. The apparatus of any one of clauses 102-107, wherein the platen includes an acoustic waveguide.

109. The apparatus of any one of clauses 102-108, wherein the platen includes an acoustic lens.

110. The apparatus of clause 109, wherein the acoustic lens resides on, or proximate, the outer surface of the platen.

111. The apparatus of clause 109 or clause 110, wherein the acoustic lens comprises a spherical lens or a cylindrical lens.

112. The apparatus of any one of clauses 102-111, wherein the platen, the light source system, or a combination thereof, is configured for transmitting light from the light source system to the outer surface of the platen along a first axis, or substantially along the first axis.

113. The apparatus of clause 112, wherein the platen is configured for transmitting the ultrasonic waves generated by the target object along a second axis, or substantially along the second axis, the second axis being different from the first axis.

114. The apparatus of clause 112, wherein the platen is configured for transmitting the ultrasonic waves generated by the target object along a second axis, or substantially along the second axis, the second axis being parallel to the first axis.

115. The apparatus of any one of clauses 102-114, further comprising a control system configured to: control the light source system to emit light; receive signals from the ultrasonic receiver system corresponding to the ultrasonic waves generated by the target object; identify one or more arterial wall signals from the ultrasonic receiver system corresponding to ultrasonic waves generated by one or more arterial walls of the target object; and estimate one or more cardiac features based, at least in part, on the one or more arterial wall signals.

116. The apparatus of any one of clauses 102-115, wherein the ultrasonic receiver comprises two or more receiver elements adjacent to a region of the platen through which light from the light source is transmitted towards the target object.

117. The apparatus of any one of clauses 102-116, wherein the platen, the light source system, or a combination thereof, is configured for transmitting light in the near infrared range.

118. The apparatus of any one of clauses 102-117, wherein the apparatus is, or includes, a mobile device and wherein the outer surface of the platen corresponds with, or is proximate, an outer surface of the mobile device.

119. The apparatus of clause 118, wherein the mobile device comprises a cellular telephone.

120. The apparatus of clause 118, wherein the mobile device comprises a pen or a stylus.

121. The apparatus of clause 120, wherein the pen or the stylus includes a force sensor, a motion sensor, a spring, or combinations thereof.

122. The apparatus of any one of clauses 102-121, wherein the platen provides an acoustic attenuation of the ultrasonic waves in a range from 0.3-6.0 decibels per centimeter per megahertz.

123. The apparatus of any one of clauses 102-122, wherein the ultrasonic waves received by the ultrasonic receiver are in a range from 0.5 MHz to 1.5 MHz and wherein the platen provides an acoustic attenuation of the ultrasonic waves in a range from 0.3-12.0 decibels per centimeter per megahertz.

124. The apparatus of clause 123, wherein a portion of the platen residing between the outer surface and the ultrasonic receiver has a thickness in a range from 0.25 cm to 0.75 cm.

125. The apparatus of any one of clauses 102-124, wherein the ultrasonic waves received by the ultrasonic receiver are in a range from 1.5 MHz to 3.0 MHz and wherein the platen provides an acoustic attenuation of the ultrasonic waves in a range from 0.3-3.0 decibels per centimeter per megahertz.

126. The apparatus of clause 125, wherein a portion of the platen residing between the outer surface and the ultrasonic receiver has a thickness in a range from 0.5 cm to 2.0 cm.

127. The apparatus of any one of clauses 102-126, wherein the ultrasonic waves received by the ultrasonic receiver are in a range from 3.0 MHz to 7.0 MHz and wherein the platen provides an acoustic attenuation of the ultrasonic waves in a range from 0.3-3.0 decibels per centimeter per megahertz.

128. The apparatus of any one of clauses 102-127, wherein a portion of the platen residing between the outer surface and the ultrasonic receiver has a thickness in a range from 2.0 cm to 6.0 cm.

129. The apparatus of any one of clauses 102-128, wherein the ultrasonic waves received by the ultrasonic receiver are in a range from 7.0 MHz to 13.0 MHz and wherein the platen provides an acoustic attenuation of the ultrasonic waves of less than 0.15 decibels per centimeter per megahertz.

130. The apparatus of clause 129, wherein a portion of the platen residing between the outer surface and the ultrasonic receiver has a thickness in a range from 2.0 cm to 6.0 cm.

131. The apparatus of any one of clauses 102-130, wherein at least an outer surface of the platen has an acoustic impedance that is configured to approximate an acoustic impedance of human skin.

132. The apparatus of any one of clauses 102-131, wherein at least an outer surface of the platen is configured to conform to a surface of human skin.

133. The apparatus of any one of clauses 102-132, wherein at least one surface of the platen comprises an anti-reflective layer.

134. The apparatus of any one of clauses 102-133, further comprising a control system configured to: control the light source system to emit light; receive signals from the ultrasonic receiver corresponding to the ultrasonic waves generated by the target object; identify arterial blood signals from the ultrasonic receiver corresponding to ultrasonic waves generated by blood within an artery of the target object; and estimate one or more cardiac features based, at least in part, on the arterial blood signals.

135. The apparatus of any one of clauses 102-134, further comprising one or more optical waveguides.

136. The apparatus of clause 135, wherein at least a portion of one of the one or more optical waveguides resides in a portion of the platen.

137. A method, comprising: controlling, by a control system, a light source system to emit light to a target object on an outer surface of a platen; receiving, by the control system, signals from an ultrasonic receiver system corresponding to the ultrasonic waves generated by a target object; identifying, by the control system, arterial signals from the ultrasonic receiver system corresponding to ultrasonic waves generated by blood within an artery of the target object, generated by one or more arterial walls of the target object, or a combination thereof; and estimating, by the control system, one or more cardiac features based, at least in part, on the arterial blood signals.

138. The method of clause 137, wherein controlling the light source system to emit light involves controlling the light source system to emit laser pulses.

139. An apparatus, comprising: a platen; light source means for providing light to a target object on an outer surface of the platen; and an ultrasonic receiver configured to receive ultrasonic waves generated by the target object, responsive to the light from the light source means, wherein one or more platen characteristics that include a thickness of the platen, an acoustic velocity of the platen, or a combination thereof, are configured to separate received one or more arterial ultrasonic waves generated by blood in an artery, by an arterial wall, or by a combination thereof, from one or more other types of received ultrasonic waves.

140. The apparatus of clause 139, wherein the one or more other types of received ultrasonic waves include reflected ultrasonic waves emitted by the ultrasonic receiver that have reflected from the target object.

141. The apparatus of clause 140, wherein the one or more platen characteristics cause the reflected ultrasonic waves emitted by the ultrasonic receiver to be received by the ultrasonic receiver after the one or more arterial ultrasonic waves.

142. An apparatus, comprising: a platen having an outer surface with an acoustic impedance that is configured to approximate the acoustic impedance of human skin, the outer surface being configured to conform to a surface of the human skin; a light source system configured for providing light to a target object on, or proximate, an outer surface of the platen; and an ultrasonic receiver configured to receive ultrasonic waves generated by the target object, responsive to the light from the light source system.

143. The apparatus of clause 142, wherein the acoustic impedance of the outer surface is within a range of plus or minus 5% of the acoustic impedance of human skin.

144. The apparatus of clause 142, wherein the acoustic impedance of the outer surface is within a range of plus or minus 10% of the acoustic impedance of human skin.

145. The apparatus of any one of clauses 142-144, wherein the acoustic impedance of the outer surface is within a range of 1.4 MRayl-1.7 MRayl.

146. The apparatus of any one of clauses 142-145, wherein the outer surface is configured to conform to ridges and valleys of a finger pad.

147. The apparatus of any one of clauses 142-146, wherein the outer surface is configured to releasably adhere to the surface of the human skin.

148. The apparatus of any one of clauses 142-147, wherein the platen is configured to increase an intensity of ultrasonic energy received by at least a portion of the ultrasonic receiver.

149. The apparatus of any one of clauses 142-148, wherein the platen includes an acoustic waveguide.

150. The apparatus of any one of clauses 142-149, wherein the platen includes an acoustic lens.

151. The apparatus of clause 150, wherein the acoustic lens resides on, or proximate, the outer surface of the platen.

152. The apparatus of clause 150 or clause 151, wherein the acoustic lens comprises a spherical lens or a cylindrical lens.

153. The apparatus of any one of clauses 142-152, wherein the platen, the light source system, or a combination thereof, is configured for transmitting light from the light source system to the outer surface of the platen along a first axis, or substantially along the first axis.

154. The apparatus of clause 153, wherein the platen is configured for transmitting the ultrasonic waves generated by the target object along a second axis, or substantially along the second axis, the second axis being different from the first axis.

155. The apparatus of clause 153, wherein the platen is configured for transmitting the ultrasonic waves generated by the target object along a second axis, or substantially along the second axis, the second axis being parallel to the first axis.

156. The apparatus of any one of clauses 142-155, further comprising a control system configured to: control the light source system to emit light; receive signals from the ultrasonic receiver system corresponding to the ultrasonic waves generated by the target object; identify one or more arterial wall signals from the ultrasonic receiver system corresponding to ultrasonic waves generated by one or more arterial walls of the target object; and estimate one or more cardiac features based, at least in part, on the one or more arterial wall signals.

157. The apparatus of any one of clauses 142-156, wherein the ultrasonic receiver comprises two or more receiver elements adjacent to a region of the platen through which light from the light source is transmitted towards the target object.

158. The apparatus of any one of clauses 142-157, wherein the platen, the light source system, or a combination thereof, is configured for transmitting light in the near infrared range.

159. The apparatus of any one of clauses 142-158, wherein the apparatus is, or includes, a mobile device and wherein the outer surface of the platen corresponds with, or is proximate, an outer surface of the mobile device.

160. The apparatus of clause 159, wherein the mobile device comprises a cellular telephone.

161. The apparatus of clause 159, wherein the mobile device comprises a pen or a stylus.

162. The apparatus of clause 161, wherein the pen or the stylus includes a force sensor, a motion sensor, a spring, or combinations thereof.

163. The apparatus of any one of clauses 142-162, wherein a thickness of the platen, an acoustic velocity of the platen, or a combination thereof, are configured to separate ultrasonic waves generated by blood in an artery from other ultrasonic waves.

164. The apparatus of any one of clauses 142-163, wherein the platen provides an acoustic attenuation of the ultrasonic waves in a range from 0.3-3.0 decibels per centimeter per megahertz.

165. The apparatus of any one of clauses 142-164, wherein a speed of sound in the platen is in a range from 800-3000 meters per second.

166. The apparatus of any one of clauses 142-165, wherein at least one surface of the platen comprises an anti-reflective layer.

167. The apparatus of any one of clauses 142-166, further comprising a control system configured to: control the light source system to emit light; receive signals from the ultrasonic receiver corresponding to the ultrasonic waves generated by the target object; identify arterial blood signals from the ultrasonic receiver corresponding to ultrasonic waves generated by blood within an artery of the target object; and estimate one or more cardiac features based, at least in part, on the blood arterial signals.

168. The apparatus of any one of clauses 142-167, further comprising one or more optical waveguides.

169. The apparatus of clause 168, wherein at least a portion of one of the one or more optical waveguides resides in a portion of the platen.

170. An apparatus, comprising: a platen having an outer surface with an acoustic impedance that is configured to approximate the acoustic impedance of human skin, the outer surface being configured to conform to a surface of the human skin; light source means for providing light to a target object on, or proximate, an outer surface of the platen; and an ultrasonic receiver configured to receive ultrasonic waves generated by the target object, responsive to the light from the light source means.

171. The apparatus of clause 170, wherein the acoustic impedance of the outer surface is within a range of plus or minus 5% of the acoustic impedance of human skin.

172. The apparatus of clause 170, wherein the acoustic impedance of the outer surface is within a range of plus or minus 10% of the acoustic impedance of human skin.

173. A method, comprising: controlling, by a control system, a light source system to emit light to a target object on an outer surface of a platen; receiving, by the control system, signals from an ultrasonic receiver system corresponding to the ultrasonic waves generated by a target object; identifying, by the control system, arterial signals from the ultrasonic receiver system corresponding to ultrasonic waves generated by blood within an artery of the target object, generated by one or more arterial walls of the target object, or a combination thereof; and estimating, by the control system, one or more cardiac features based, at least in part, on the arterial blood signals.

174. The method of clause 173, wherein controlling the light source system to emit light involves controlling the light source system to emit laser pulses.

As used herein, a phrase referring to "at least one of" a list of items refers to any combination of those items, including single members. As an example, "at least one of: a, b, or c" is intended to cover: a, b, c, a-b, a-c, b-c, and a-b-c.

The various illustrative logics, logical blocks, modules, circuits and algorithm processes described in connection with the implementations disclosed herein may be implemented as electronic hardware, computer software, or combinations of both. The interchangeability of hardware and software has been described generally, in terms of functionality, and illustrated in the various illustrative components, blocks, modules, circuits and processes described above. Whether such functionality is implemented in hardware or software depends upon the particular application and design constraints imposed on the overall system.

The hardware and data processing apparatus used to implement the various illustrative logics, logical blocks, modules and circuits described in connection with the aspects disclosed herein may be implemented or performed with a general purpose single- or multi-chip processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, or, any conventional processor, controller, microcontroller, or state machine. A processor also may be implemented as a combination of computing devices, e.g., a combination of a DSP and a microprocessor, a plurality of microprocessors, one or more microprocessors in conjunction with a DSP core, or any other such configuration. In some implementations, particular processes and methods may be performed by circuitry that is specific to a given function.

In one or more aspects, the functions described may be implemented in hardware, digital electronic circuitry, computer software, firmware, including the structures disclosed in this specification and their structural equivalents thereof, or in any combination thereof. Implementations of the subject matter described in this specification also may be implemented as one or more computer programs, i.e., one or more modules of computer program instructions, encoded on a computer storage media for execution by, or to control the operation of, data processing apparatus.

If implemented in software, the functions may be stored on or transmitted over as one or more instructions or code on a computer-readable medium, such as a non-transitory medium. The processes of a method or algorithm disclosed herein may be implemented in a processor-executable software module which may reside on a computer-readable medium. Computer-readable media include both computer storage media and communication media including any medium that may be enabled to transfer a computer program from one place to another. Storage media may be any available media that may be accessed by a computer. By way of example, and not limitation, non-transitory media may include RAM, ROM, EEPROM, CD-ROM or other optical disk storage, magnetic disk storage or other magnetic storage devices, or any other medium that may be used to store desired program code in the form of instructions or data structures and that may be accessed by a computer. Also, any connection may be properly termed a computer-readable medium. Disk and disc, as used herein, includes compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and instructions on a machine readable medium and computer-readable medium, which may be incorporated into a computer program product.

Various modifications to the implementations described in this disclosure may be readily apparent to those having ordinary skill in the art, and the generic principles defined herein may be applied to other implementations without departing from the spirit or scope of this disclosure. Thus, the disclosure is not intended to be limited to the implementations shown herein, but is to be accorded the widest scope consistent with the claims, the principles and the novel features disclosed herein. The word "exemplary" is used exclusively herein, if at all, to mean "serving as an example, instance, or illustration." Any implementation described herein as "exemplary" is not necessarily to be construed as preferred or advantageous over other implementations.

Certain features that are described in this specification in the context of separate implementations also may be implemented in combination in a single implementation. Conversely, various features that are described in the context of a single implementation also may be implemented in multiple implementations separately or in any suitable subcombination. Moreover, although features may be described above as acting in certain combinations and even initially claimed as such, one or more features from a claimed combination may in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems may generally be integrated together in a single software product or packaged into multiple software products. Additionally, other implementations are within the scope of the following claims. In some cases, the actions recited in the claims may be performed in a different order and still achieve desirable results.

It will be understood that unless features in any of the particular described implementations are expressly identified as incompatible with one another or the surrounding context implies that they are mutually exclusive and not readily combinable in a complementary and/or supportive sense, the totality of this disclosure contemplates and envisions that specific features of those complementary implementations may be selectively combined to provide one or more comprehensive, but slightly different, technical solutions. It will therefore be further appreciated that the above description has been given by way of example only and that modifications in detail may be made within the scope of this disclosure.

Various modifications to the implementations described in this disclosure may be readily apparent to those skilled in the art, and the generic principles defined herein may be applied to other implementations without departing from the spirit or scope of this disclosure. Thus, the following claims are not intended to be limited to the implementations shown herein, but are to be accorded the widest scope consistent with this disclosure, the principles and the novel features disclosed herein.

Additionally, certain features that are described in this specification in the context of separate implementations also can be implemented in combination in a single implementation. Conversely, various features that are described in the context of a single implementation also can be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Further, the drawings may schematically depict one more example processes in the form of a flow diagram. However, other operations that are not depicted can be incorporated in the example processes that are schematically illustrated. For example, one or more additional operations can be performed before, after, simultaneously, or between any of the illustrated operations. Moreover, various ones of the described and illustrated operations can itself include and collectively refer to a number of sub-operations. For example, each of the operations described above can itself involve the execution of a process or algorithm. Furthermore, various ones of the described and illustrated operations can be combined or performed in parallel in some implementations. Similarly, the separation of various system components in the implementations described above should not be understood as requiring such separation in all implementations. As such, other implementations are within the scope of the following claims. In some cases, the actions recited in the claims can be performed in a different order and still achieve desirable results.

What is claimed is:

1. An apparatus, comprising:
a platen;
a light source system configured for providing light to a target object on an outer surface of the platen; and
an ultrasonic receiver system configured to receive ultrasonic waves generated by the target object, responsive to the light from the light source system provided to the target object, wherein the platen includes a first cone-shaped platen portion configured for transmitting the light from the light source system to the outer surface of the platen along a first axis corresponding with the first platen portion and a second cone-shaped platen portion configured for transmitting the ultrasonic waves generated by the target object along a second axis corresponding with the second platen portion, the first platen portion being connected to the second platen portion, a first surface of first platen portion being proximate the light source system, the first surface of first platen portion being offset from a second surface of the second platen portion proximate the ultrasonic receiver system by an angle between the first axis and the second axis.

2. The apparatus of claim 1, wherein the platen is configured to increase an intensity of ultrasonic energy received by at least a portion of the ultrasonic receiver system.

3. The apparatus of claim 1, wherein the platen includes an acoustic waveguide.

4. The apparatus of claim 1, wherein the platen includes an acoustic lens.

5. The apparatus of claim 4, wherein the acoustic lens resides on, or proximate, the outer surface of the platen.

6. The apparatus of claim 4, wherein the acoustic lens comprises a spherical lens or a cylindrical lens.

7. The apparatus of claim 1, wherein the second platen portion has a cylindrical shape.

8. The apparatus of claim 1, wherein at least one surface of the platen comprises an anti-reflective layer.

9. The apparatus of claim 7, wherein the ultrasonic receiver system comprises two or more receiver elements adjacent to a region of the platen through which light from the light source is transmitted towards the target object.

10. The apparatus of claim 1, wherein the platen, the light source system, or a combination thereof, is configured for transmitting light in the near infrared range.

11. The apparatus of claim 1, wherein the apparatus is, or includes, a mobile device and wherein the outer surface of the platen corresponds with, or is proximate, an outer surface of the mobile device.

12. The apparatus of claim 11, wherein the mobile device comprises a cellular telephone.

13. The apparatus of claim 11, wherein the mobile device comprises a pen or a stylus.

14. The apparatus of claim 13, wherein the pen or the stylus includes a force sensor, a motion sensor, a spring, or combinations thereof.

15. The apparatus of claim 1, wherein a thickness of the platen, an acoustic velocity of the platen, or a combination thereof, are configured to separate ultrasonic waves generated by blood in an artery from other ultrasonic waves.

16. The apparatus of claim 1, wherein the platen provides an acoustic attenuation of the ultrasonic waves in a range from 0.3-3.0 decibels per centimeter per megahertz.

17. The apparatus of claim 1, wherein at least an outer surface of the platen has an acoustic impedance that is configured to approximate an acoustic impedance of human skin.

18. The apparatus of claim 1, wherein at least an outer surface of the platen is configured to conform to a surface of human skin.

19. The apparatus of claim 1, wherein a speed of sound in the platen is in a range from 800-3000 meters per second.

20. The apparatus of claim 1, further comprising a control system configured to:
  control the light source system to emit light;
  receive signals from the ultrasonic receiver system corresponding to the ultrasonic waves generated by the target object;
  identify arterial blood signals from the ultrasonic receiver system corresponding to ultrasonic waves generated by blood within an artery of the target object; and
  estimate one or more cardiac features based, at least in part, on the arterial blood signals.

21. The apparatus of claim 1, further comprising a control system configured to:
  control the light source system to emit light;
  receive signals from the ultrasonic receiver system corresponding to the ultrasonic waves generated by the target object;
  identify one or more arterial wall signals from the ultrasonic receiver system corresponding to ultrasonic waves generated by one or more arterial walls of the target object; and
  estimate one or more cardiac features based, at least in part, on the one or more arterial wall signals.

22. The apparatus of claim 1, further comprising one or more optical waveguides.

23. The apparatus of claim 22, wherein at least a portion of one of the one or more optical waveguides resides in a portion of the platen.

24. An apparatus, comprising:
  a platen;
  light source means for providing light to a target object on, or proximate, an outer surface of the platen; and
  an ultrasonic receiver system configured to receive ultrasonic waves generated by the target object, responsive to the light from the light source means provided to the target object, wherein the platen includes a first cone-shaped platen portion configured for transmitting the light from the light source system to the outer surface of the platen along a first axis corresponding with the first platen portion and a second cone-shaped platen portion configured for transmitting the ultrasonic waves generated by the target object along a second axis corresponding with the second platen portion.

25. The apparatus of claim 24, wherein the platen is configured to increase an intensity of ultrasonic energy received by at least a portion of the ultrasonic receiver system.

26. The apparatus of claim 24, wherein the platen includes an acoustic waveguide.

27. The apparatus of claim 24, wherein the platen includes an acoustic lens.

* * * * *